(12) United States Patent
Weidanz et al.

(10) Patent No.: US 6,534,633 B1
(45) Date of Patent: Mar. 18, 2003

(54) POLYSPECIFIC BINDING MOLECULES AND USES THEREOF

(75) Inventors: Jon A. Weidanz, Miami, FL (US); Kimberlyn F. Card, Pembroke Pines, FL (US); Linda A. Sherman, La Jolla, CA (US); Norman R. Klinman, La Jolla, CA (US); Hing C. Wong, Weston, FL (US)

(73) Assignee: Altor Bioscience Corporation, Miramar, FL (US)

( * ) Notice: Subject to any disclaimer, the term of this patent is extended or adjusted under 35 U.S.C. 154(b) by 0 days.

(21) Appl. No.: 09/422,375

(22) Filed: Oct. 21, 1999

Related U.S. Application Data
(60) Provisional application No. 60/105,164, filed on Oct. 21, 1998.

(51) Int. Cl.[7] .............................................. C07K 16/93
(52) U.S. Cl. ............................... 530/387.3; 530/387.1; 424/136.1
(58) Field of Search ............................. 530/350, 387.1, 530/387.3, 391.3, 391.7; 424/134.1, 135.1, 136.1

(56) References Cited

U.S. PATENT DOCUMENTS

| | | | |
|---|---|---|---|
| 5,616,472 A | | 4/1997 | Choi et al. |
| 5,637,481 A | | 6/1997 | Ledbetter et al. |
| 5,723,309 A | | 3/1998 | Bonneville |
| 6,015,884 A | * | 1/2000 | Schneck et al. |

FOREIGN PATENT DOCUMENTS

| | | | |
|---|---|---|---|
| WO | WO 88/09344 | * | 12/1988 |
| WO | WO/93/22332 | | 11/1993 |
| WO | WO 96/18105 | * | 6/1996 |

OTHER PUBLICATIONS

S. Wu, et al., *Journal of Immunology*, vol. 150, No. 5, Mar. 15, 1993, pp. 2211–2221.
N. Jacobs, et al., *Cancer Immunol Immunother*, 44: (1997), pp. 257–264.
A. I. Chapoval, et al., *Journal of Hematotherapy*, 4: (1995), pp. 571–577.
M. Theobald, et al., *Proc. Natl. Acad. Sci. USA*, vol. 92, Dec. 1995 Immunology, pp. 11993–11997.
S. Riedle, et al., *Int. J. Cancer*, 75, (1998), pp. 908–918.
L. Porter, et al., *Cancer Immunol Immunother* , 45: (1997), pp. 180–183.
H. Lindhofer, et al., *Blood*, vol. 88, No. 12, Dec. 15, 1996, pp. 4651–4658.
C. R. Jost, et al., *Molecular Immunology*, vol. 33, No. 2, pp. 211–219, 1996.
M. Mack, et al., *The American Association of Immunologists*, (1997). pp. 3965–3970.
C. R. Jost, et al., *The Journal of Biological Chemistry*, vol. 269, No. 42, Oct. 21, 1994, pp. 26267–26273.

* cited by examiner

*Primary Examiner*—Sheela Huff
*Assistant Examiner*—Larry R. Helms
(74) *Attorney, Agent, or Firm*—Robert L. Buchanan; Peter F. Corless; Edward & Angell, LLP

(57) ABSTRACT

The present invention relates to polyspecific binding molecules and particularly single-chain polyspecific binding molecules that include at least one single-chain T-cell receptor (sc-TCR) covalently linked through a peptide linker sequence to at least one single-chain antibody (sc-Ab). Further disclosed are methods and compositions for testing and using the molecules.

31 Claims, 24 Drawing Sheets

DO11.10 scTCR: | Vα13.1 | (G4S)4 | Vβ8.2 Cβ |

FIG. 1A p149 scTCR: | Vα2 + 7AA Cα | (G4S)4 | Vβ11 Cβ |

FIG. 1B 145-2C11 scFv: | V light | (G4S)3 | V heavy |

FIG. 1C

F23.1 scFv: | V heavy | G4SG4APG4S | V light |

FIG. 1D

| BISP/DO11.10 | DO11.10 scTCR | linker | 145-2c11 scFv | EE |
|---|---|---|---|---|
| BISP/149 | p149 scTCR | linker | 145-2c11 scFv | EE |

FIG. 6

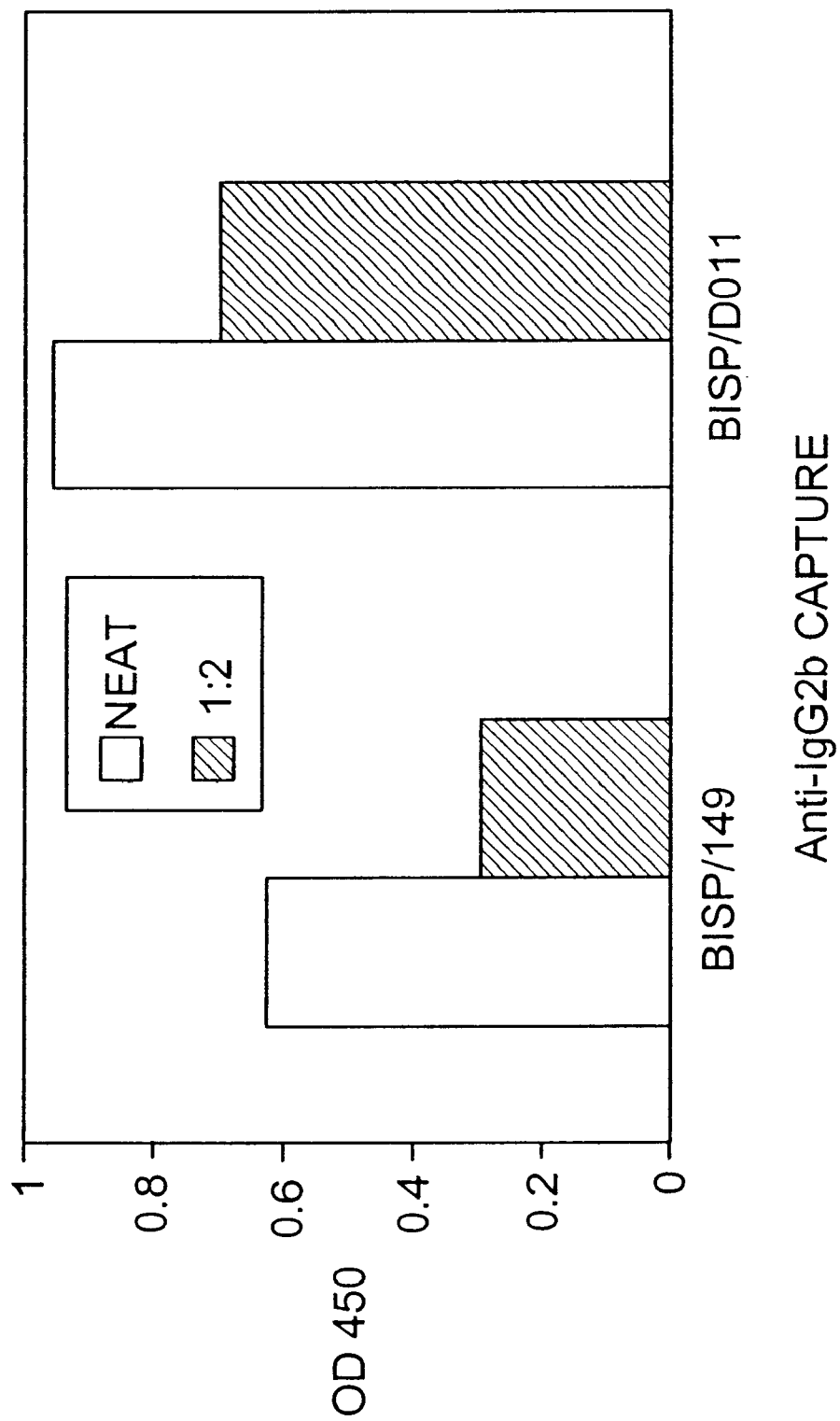

| FIG. 21A-1 |
| FIG. 21A-2 |
| FIG. 21A-3 |

FIG. 21A

KC169    GAG GTG ACC GGT GAG GAG CAG GTG GAG CAG CTT CC  (SEQ ID NO. 16).

KC171    GAG GTG GAG GCC CAG CAG CCG GCC ATG GCC CAG CAG GTG AGA CAA  AG
         (SEQ ID NO. 17).

KC 172   GAG GTG GAG CTC GAG CAA TGC TGG TGT CAT CCA AAC
         (SEQ ID NO. 18).

KC 174   GAG GTG GAG ACT AGT AGC TTC TGG GTT CTG (SEQ ID NO. 19).

KC 176   GAG GTG GAG CCC GGG GTC TGC TCG GCC CCA GGC
         (SEQ ID NO. 20)

FIG. 21A-1

| | | |
|---|---|---|
| 15 | KC203 | GAG GTG ACC GGT CAG CAG GTG AGA CAA AGT CC (SEQ ID NO. 21). |
| | KC208 | GTG GAG ATC GAT AAG TGT ACT TAC GTT TTC ATT ATC GCG ATC CGG AGT TAACGT CTG CTC GGC CCC AG (SEQ ID NO. 22). |
| | KC209 | AAC GCA AAG ACA ACC GCC CCT TCA GTA TAT CCA CTA GCG CCC GTT T (SEQ ID NO. 23). |
| 20 | KC210 | CCG GAA ACG GGC GCT AGT GGA TAT ACT GAA GGG GCG GTT GTC GCG TT (SEQ ID NO. 24). |
| 25 | KC237 | CGA GAG GAA GAG TAC ATG CCG ATG GAA TAA TGA AAA CGT AAG TAC ACT TAT (SEQ ID NO. 25). |

FIG. 21A-2

KC238    CGA TAA GTG TAC TTA CGT m CAT TAT TCC ATC GGC ATG TCT TCT TCC TCT CG (SEQ ID NO. 26).

KC239    CGA AAA CGT AAG TAC ACT TAT (SEQ ID NO. 27).

| FIG. 21B-1 |
| FIG. 21B-2 |
| FIG. 21B-3 |

FIG. 21B

KC240   CGA TAA GTG TAC TTA CGT TTT CG (SEQ ID NO. 28).

KC 243  GAG GTG GCC CAG CCG GCC ATG GCC GAC ATC CAG ATG ACC (SEQ ID NO. 29).

KC244   GAG GT0 ACT AGT TTT GAT TTC CAG CTT GGT G (SEQ ID NO. 30).

KC245   CTA GTG GAG GTG GCG GAT CAG GAG GCG GAG GTT CTG GCG GAG GTG GGAGTC (SEQ ID NO. 31).

KC246   TCG AGA CTC CCA CCT CCG CCA GAA CCT CCG CCT CCT GAT CCG CCA CCT CCA (SEQ ID NO. 32).

FIG. 21B-1

| | | |
|---|---|---|
| | KC247 | GAG GTG CTC GAG GAG GTG CAG CTG GTG G (SEQ ID NO. 33). |
| 15 | KC250 | GAG GTG TCC GGA GAC ATC CAG ATG ACC (SEQ ID NO. 34). |
| | KC251 | GAG GTG TCG CGA TGA GGA GAC GGT GAC C (SEQ ID NO. 35). |
| 20 | KC253 | GAG GTG GAA TTC TCA TTA CCC GGG TGA GGA GAC GGT GAC CAT G (SEQ ID NO. 36). |
| | KC268 | GTG GAG GAA TTC GTC TGC TCG GCC CCA G (SEQ ID NO. 37). |
| 25 | KC275 | GAG GTG TCG CGA CAG CTA CCG GTG TCC ACT CCG AGC AGG TGG AGC AGC TTC C (SEQ ID NO. 38). |
| | KC276 | GAG GTG TCG CGA CAG CTA CCG GTG TCC ACT CCC AGC AGG TGA GAC AAA GTC C (SEQ ID NO. 39). |

FIG. 21B-2

KC293  CAA GCA GCC TCA GGA ACT CTG GAA ATA CGC TC (SEQ ID NO. 40).

KC294  GAG CGT ATT TCC AGA GTT CCT GAG GCT GCT TG [SEQ ID NO. 41].

KC295  AAC GGT GGA GGG GGC TCA T (SEQ ID NO. 42).

KC296  CCG GAT GAG CCC CCT CCA CCG TT (SEQ ID NO. 43).

FIG. 21B-3

POLYSPECIFIC BINDING MOLECULES AND USES THEREOF

CROSS-REFERENCE TO RELATED APPLICATIONS

The present application claims priority to U.S. Provisional Application No. 60/105,164 filed on Oct. 21, 1998, the disclosure of which is hereby incorporated by reference.

FIELD OF THE INVENTION

The present invention relates to polyspecific binding molecules, as well as methods of making and using such molecules. In one aspect, the invention features single-chain polyspecific binding molecules that can damage or destroy target cells. The invention is useful for a variety of applications including use in associating cells that express a T-cell receptor or an antibody binding domain.

BACKGROUND

There has been recognition that immune system cells and particularly cytotoxic T lymphocytes (CTLs) can be used to detect tumor associated antigens (TAAs). For example, CTLs derived from melanomas have been used to identify a variety of melanoma-specific antigens. See e.g., Bruggen et al., *Science*, (1991), 254:1643; Bakker et al., *J. Exp. Med.*, (1994), 179: 1005; and Yanuck et al., *Cancer Research*, (1993), 53, 3257.

Several anti-tumor therapies have attempted to use CTLs to treat diseases such as cancer. In one approach, anti-tumor CTLs are taken from a patient, expanded in vitro, and then given back to the patient to treat the cancer. However, this approach suffers from significant drawbacks. For example, it is not always straightforward to isolate sufficient quantities of the CTLs from the patient. In addition, at least some of the CTLs may have specificities that have survived self-tolerance that could lead to additional complications. See, e.g., Browning et al., *Curr. Opin. Immunol.*, (1992) 4, 613; Mizoguchi et al., *Science*, (1992), 258:1795, and George et al., *J. Immunol.*, (1994), 152, 1802.

There have been attempts to mitigate these and other shortcomings by making and using recombinant immune molecules such as those resembling antibodies. An antibody has a recognized structure that includes an immunoglobulin heavy and light chain. The heavy and light chains include an N-terminal variable region (V) and a C-terminal constant region (C). The heavy chain variable region is often referred to as "$V_H$" and the light chain variable region is referred to as "$V_L$". The $V_H$ and $V_L$ chains form a binding pocket that has been referred to as F(v). See generally Davis *Ann. Rev. of Immunology* (1985), 3: 537; and *Fundamental Immunology* 3rd Ed., W. Paul Ed. Raven Press LTD. New York (1993).

Recombinant antibody molecules have been disclosed. For example, several recombinant bispecific antibody (bsFv) molecules have been reported. Most of the bsFv molecules include a F(v) formatted as a single-chain (sc-Fv). More particular sc-Fv molecules include a $V_H$ linked to a $V_L$ through a peptide linker sequence. See e.g., Huston et al. *PNAS (USA)*, (1988), 85:5879; Bird et al., *Science*, (1988), 242: 423; WO 94/29350; and U.S. Pat. No. 5,455,030.

Additional bsFv molecules have been disclosed. For example, some bsFv molecules have been reported to bind a T-cell protein termed "CD3" and a TAA. There is recognition that binding of the bsFv may facilitate an immune system response. See e.g., Jost, C. R. (1996) *Mol. Immunol.* 33: 211; Lindhofer, H. et al. (1996) *Blood*, 88: 465 1; Chapoval, A. I. et al. (1995) *J. of Hematotherapy*, 4: 571.

There have been attempts to develop straightforward methods of making bispecific antibody molecules. However, many of these attempts have been associated with problems. For example, many of the molecules are reported to be insoluble especially in bacterial expression systems. See e.g., Wels et al., (1992), *Biotechnology*, 10:1128.

Attempts to make other recombinant immune molecules have been reported. For example, there have been specific attempts to manipulate T-cell receptors (TCRs). The TCR is a membrane bound heterodimer consisting of an α and β chain that resembles an immunoglobulin variable (V) and constant (C) region. The TCR α chain includes a covalently linked V-α and C-αchain. The TCR β chain includes a Vβ chain covalently linked to a C-βchain. See generally Davis, supra.

There have been specific efforts to manipulate the TCR by recombinant DNA techniques. For example, in one approach, the TCR has been formatted as a single-chain fusion protein comprising the TCR V regions (sc-TCR). The sc-TCR molecule has been reported to have several important uses. See e.g., Soo Hoo, W. F. et al. *PNAS (USA)* 89, 4759 (1992); Wülfing, C. and Plückthun, A., *J. Mol. Biol.* 242, 655 (1994); Kurucz, I. et al. *PNAS (USA)* 90 3830 (1993); PCT WO 96/13593; PCT WO 96/18105; and Schlueter, C. J. et al. *J. Mol. Biol.* 256, 859 (1996).

The prior recombinant immune molecules are believed to be associated with significant shortcomings.

For example, there has been recognition that many tumor antigens are "shed" from cells, thereby providing sites for non-specific immune molecule binding. In particular, it has been proposed that many bsFv molecules inadvertently interact with the shed antigens, thereby reducing tumor cell killing efficiency.

The prior immune molecules suffer from additional drawbacks. For example, there has been recognition that many bsFv molecules cannot bind potential target antigens such as certain peptides on the surface of tumor cells. As an illustration, the tumor related protein p53 is usually not expressed on tumor cells as an intact protein. Instead, p53 has been reported to be processed and presented as a peptide in the context of a cell surface class I or class II molecule. Thus, in settings in which binding to specific cell surface peptides is needed, it has been difficult or impossible for bsFv molecules.

Further, it has been difficult to isolate some bsFv molecules without significant isolation and/or re-folding steps. See e.g., Jost, C. R. et al. supra and references cited therein.

Preparation and use of many sc-TCRs has also been associated with problems. For example, several prior methods for making the sc-TCRs have yielded insoluble and improperly folded molecules. Several strategies have been developed in an attempt to improve sc-TCR yields. However, the sc-TCRs produced by these methods often require time-consuming manipulations to obtain even modest amounts of protein. See e.g., Ward, E. S. et al. supra; Schlueter, C. J. supra; and published PCT applications WO 96/18105 and WO 96/13593.

There is a need therefore for recombinant immune molecules and particularly single-chain polyspecific binding molecules that can damage or eliminate (kill) target cells in vitro and in vivo. It would be desirable to have methods for making the polyspecific binding molecules with a minimum of difficult preparative steps.

SUMMARY OF THE INVENTION

The present invention relates to novel immune molecules and particularly to single-chain polyspecific binding proteins that damage or eliminate (kill) desired target cells. The single-chain polyspecific binding proteins include at least one receptor domain capable of specifically binding a peptide bound (loaded) to a major histocompatibility complex (MHC) or a human-leukocyte-associated antigen (HLA); and at least one antibody domain capable of binding an antigen. The present single-chain polyspecific binding molecules are fully soluble and can be isolated in significant quantities with a minimum of difficult preparative steps. Also provided are methods and compositions for screening the single-chain polyspecific binding proteins for capacity to bind desired cells.

We have made novel polyspecific binding molecules that feature a wide variety of useful activities. For example, the single-chain polyspecific binding proteins can associate cells expressing the peptide bound (loaded) MHC (HLA) to cells expressing the antigen. In most instances, the MHC (HLA) and the antigen will be on separate cells. Association of the cells in accord with the invention preferably facilitates an immune response that can damage or kill the cells expressing the peptide bound (loaded) MHC (HLA) complexes. The present invention has a wide spectrum of useful applications including use in the treatment of certain cancers and viral infections.

More particularly, the present invention features single-chain polyspecific binding proteins that include at least one single-chain T-cell receptor (sc-TCR) or functional fragment thereof sufficient to bind a particular peptide bound (loaded) to the MHC (HLA). A cell expressing the peptide bound (loaded) MHC or HLA will often be referred to herein as a "target cell" or similar term. The polyspecific binding proteins further include at least one antibody binding domain and particularly a single-chain antibody or functional fragment thereof, which antibody binding domain is sufficient to bind the antigen. In most embodiments, the antigen bound by the antibody binding domain will be expressed on a cell surface, usually on the surface of an immune cell. In particular embodiments, the antigen will be selective for the immune cells. More preferred single-chain polyspecific binding molecules of this invention are capable of forming a specific binding complex ("bridge") between the peptide bound (loaded) MHC or HLA on the target cell and the antigen on the immune cell. Without wishing to be bound to theory, it is believed that formation of the bridge in accord with the invention facilitates an immune response that can damage or kill the target cells.

Preferred polyspecific binding molecules of this invention specifically bind MHC or HLA complexes. Unless otherwise specified, the term MHC and HLA as used herein means a complex to which a particular peptide is bound (loaded). In some instances, the MHC (HLA) complexes will be referenced as "pMHC", "pHLA" or like term to denote the peptide binding (loading). The polyspecific binding molecules are thus useful for binding the MHC and HLA complexes and for bridging those complexes to an immune cell expressing a desired antigen. In some instances, the immune cell antigen bound by a particular polyspecific binding molecule will be referred to as an "activation" molecule or marker to denote preferred activation of the immune cell following binding by the polyspecific molecule.

Accordingly, in one aspect, the present invention features single-chain polyspecific binding proteins that include at least one sc-TCR covalently linked (i.e. fused) to at least one single-chain antibody (sc-Ab). In embodiments in which the single-chain polyspecific molecule include one sc-TCR and one sc-Ab, the sc-TCR and the sc-Ab molecules may be directly fused together although it is generally preferred to separate the sc-TCR and sc-Ab from each other through a suitable (first) peptide linker sequence. Alternatively, functional fragments of the sc-TCR and/or sc-Ab molecules may be employed in the proteins. In preferred embodiments, the polyspecific binding proteins will include the sc-TCR linked to the sc-Ab through the first peptide linker sequence.

More particularly, the sc-TCR is preferably a single-chain V chain. The V chain will typically include a V$\alpha$,$\beta$ sequence in which a V-$\alpha$ chain is fused to a V-$\beta$ chain. In a specific embodiment, the fusion is achieved by covalently linking the molecules through a (second) peptide linker sequence. The fusion product may be further covalently linked through the V-$\alpha$ or V-$\beta$ chain to an immunoglobulin constant chain (Ig-$C_L$) or fragment thereof if desired.

In a more specific embodiment, the C-terminus of the sc-TCR V-$\alpha$ chain is covalently linked by the second peptide linker sequence to the N-terminus of V-$\beta$ chain. Alternatively, the C-terminus of the sc-TCR V-$\beta$ chain can be covalently linked by the second peptide linker sequence to the N-terminus of the V-$\alpha$ chain.

In another embodiment, a TCR C-$\beta$ chain or fragment thereof is covalently linked between the C-terminus of the sc-TCR V-$\beta$ chain and the N-terminus of the first peptide linker sequence. Alternatively, the TCR C-$\beta$ chain or the fragment may be covalently linked between the C-terminus of the sc-TCR V-$\alpha$ chain and the N-terminus of the first peptide linker sequence.

In another embodiment, a TCR C-$\alpha$ chain or fragment thereof is covalently linked between the C-terminus of the sc-TCR V-$\alpha$ chain and the N-terminus of the second peptide linker sequence fused to the V-$\beta$ sequence. Alternatively, the C-$\alpha$ chain or fragment can be covalently linked between the C-terminus of the V-$\beta$ chain and the N-terminus of the second peptide linker sequence fused to the V-$\alpha$ sequence.

In a particular embodiment, the sc-TCR includes the TCR C-$\alpha$ chain or fragment covalently linked between the C-terminus of the sc-TCR V-$\alpha$ chain and the N-terminus of the second peptide linker sequence fused to the sc-TCR V-$\beta$ sequence. Further, the TCR C-$\beta$ chain or fragment is covalently linked between the C-terminus of the V-$\beta$ chain and the N-terminus of the first peptide linker sequence.

As discussed, the polyspecific binding molecules of this invention include at least one sc-Ab. In a particular embodiment the antibody binding domain includes at least one sc-Fv. More preferred single-chain polyspecific binding proteins include one sc-Fv or a functional fragment thereof. An illustrative sc-Fv includes at least two immunoglobulin chains and especially two immunoglobulin variable chains, e.g., a light chain ($V_L$) fused to a heavy chain ($V_H$). In this embodiment, the $V_L$ and $V_H$ chains may be fused together although it is generally preferred to covalently link the chains through a (third) peptide linker sequence.

In a particular embodiment, the C-terminus of the $V_L$ chain is covalently linked by the third peptide linker sequence to the N-terminus of $V_H$ chain. In another embodiment, the C-terminus of the $V_H$ chain is covalently linked by the third peptide linker sequence to the N-terminus of the $V_L$ chain.

In a more particular embodiment, the C-terminus of the sc-TCR V$\beta$ chain is covalently linked to the third polypeptide linker sequence which sequence is further linked to the N-terminus of the $V_H$ chain. Alternatively, the C-terminus of the sc-TCR V-$\beta$ is covalently linked to the third polypeptide linker sequence as discussed except that the polypeptide sequence is further linked to the N-terminus of the $V_L$ chain.

In another embodiment, the C-terminus of the sc-TCR V-β chain is covalently linked to a C-β chain which chain is covalently linked to the third polypeptide linker sequence which sequence is linked to the N-terminus of the $V_H$ chain. Alternatively, the C-terminus of the sc-TCR V-β chain is covalently linked to a C-β chain which chain is covalently linked to the third polypeptide linker sequence which sequence is linked to the N-terminus of the $V_L$ chain.

In a preferred embodiment, the present invention provides single-chain "bispecific" binding proteins that include at least one sc-TCR (or fragment thereof), and at least one sc-Fv (or fragment thereof) covalently linked together through a suitable peptide linker sequence. In instances in which more than one sc-TCR and/or sc-Fv are used the sc-TCRs and sc-Fvs are preferably the same. The single-chain bispecific binding protein will sometimes be referred to herein as a "bispecific hybrid molecule" or "sc-TCR/scFv hybrid molecule" or similar phrase. The bispecific hybrid molecules of this invention may include additional amino acid sequences such as protein tags. More preferred bispecific binding proteins are discussed as follows.

For example, in one embodiment, the bispecific binding molecules include covalently linked in sequence: 1) a sc-TCR or functional fragment thereof of interest, 2) a suitable peptide linker sequence, and 3) a sc-Fv or functional fragment thereof. In a more particular embodiment, the sc-TCR further includes covalently linked in sequence: 4) the V-α chain, 5) a suitable peptide linker sequence, 6) a V-β chain, and 7) an optional C-β chain fragment. Alternatively, the sc-TCR can include covalently linked in sequence: 4) the V-β chain, 5) the linker sequence, 6) the V-α chain, and 7) an optional C-β chain or fragment thereof. In another particular embodiment, the sc-TCR further includes a C-α chain or fragment thereof covalently linked between the V-α chain and the peptide linker sequence fused to V-β chain.

In another particular embodiment, the bispecific binding molecules include a sc-Fv that which includes covalently linked in sequence: 8) the $V_H$ chain, 9) a suitable polypeptide linker sequence, and 10) the $V_L$ chain. In another embodiment, the sc-Fv includes covalently linked in sequence: 8) the $V_L$ chain, 9) the polypeptide linker sequence, and 10) the $V_H$ chain.

The single-chain polyspecific binding proteins of this invention may further include at least one protein tag covalently linked thereto, preferably from between about 1 to 3 of such tags. Preferably, the protein tag is fused to the C-terminus of a desired binding molecule although for some applications fusion to the N-terminus may be more preferred.

In a more specific embodiment, the single-chain polyspecific binding protein includes covalently linked in sequence: 1) the TCR V-α chain, 2) a peptide linker sequence, 3) the TCR V-β chain covalently linked to a C-β chain fragment, 4) a peptide linker sequence, 5) the $V_L$ chain, 5) a peptide linker sequence, and 6) the $V_H$ chain. In another embodiment, the single-chain polyspecific binding protein includes covalently linked in sequence: 1) the TCR V-α chain, 2) a peptide linker sequence, 3) the TCR V-β chain covalently linked to a C-β chain fragment, 4) a peptide linker sequence, 5) the $V_H$ chain, 5) a polypeptide linker sequence, and the 6) $V_L$ chain.

Significantly, the present invention is flexible. That is, the invention features polyspecific binding molecules that can include a variety of sc-TCR and sv-FV components. As will be appreciated, the order in which the components are made or assembled is usually not important so long as desired binding and activation characteristics are achieved.

In another embodiment, the present invention features multi-chain polyspecific binding proteins that include at least one sc-TCR (functional fragment thereof) and at least one antibody binding domain which can be, e.g., an F(v) or sc-Fv. The binding molecules more specifically include at least one "joining molecule" to link the sc-TCR and antibody binding domain. As will be more fully discussed below, the joining molecule may be covalently or non-covalently linked to the sc-TCR, the antibody binding domain, or both. For example, in one preferred embodiment, two compatible joining molecules are each independently fused to the sc-TCR and the sc-Fv.

The term "joining molecule" means an amino acid sequence that is capable of specifically binding, either covalently or non-covalently, to a second amino acid sequence. Sometimes the second amino acid sequence is referred to as a "cognate" sequence to denote capacity to form a specific binding pair. The second sequence may also be sometimes referred to herein as a second joining molecule, which second joining molecule can be the same as, or different from, the (first) joining molecule. More particular joining molecules include immunoglobulin chains and particularly constant chains (H or L) or suitable fragments thereof, coiled-coil motifs and helix-turn-helix motifs. More specific examples of joining molecules are disclosed below.

It will be apparent from the discussion which follows that in some instances a joining molecule may also serve as a protein tag.

A more particular multi-chain polyspecific binding molecule includes more than one joining molecule and preferably about 2 of such joining molecules. In a more specific embodiment, one sc-TCR is fused to the first joining molecule. The first joining molecule can be either covalently or non-covalently linked to the second joining molecule which is further linked to the antibody binding domain. However in some embodiments such as when the first and second joining molecules are suitable immunoglobulin chains, a combination of covalent and non-covalent bonds may be employed to link the sc-TCR and the antibody binding domain through the first and second joining molecules.

As an illustration, a particular multi-chain polyspecific binding protein includes covalently linked to at least one sc-TCR, preferably one sc-TCR, an immunoglobulin heavy chain (Ig-$C_H$) or functional fragment. Sometimes this construct will be referred to herein as a "sc-TCR/Ig fusion protein", "sc-TCR/Ig" or similar phrase. It will be appreciated that the immunoglobulin heavy chain portion of the sc-TCR/Ig fusion protein is representative of one type of joining molecule as defined above and in the discussion following. In a more specific embodiment, the binding molecule further includes a second joining molecule, which is preferably a suitable immunoglobulin heavy chain capable of forming a binding complex. The isotype of the immunoglobulin chains may be different but are preferably the same to facilitate binding. The second joining molecule is bound to the antibody binding domain which is preferably an F(v) and particularly an sc-Fv. In other embodiments, the sc-TCR may be further bound covalently or non-covalently to an immunoglobulin variable chain and preferably a variable light chain.

The single- and multi-chain polyspecific binding proteins disclosed herein preferably include TCR V-α and the V-β chains that are at least 90% identical to T-cell receptor V chains present on a cytotoxic T cell. Preferably, at the least the sc-TCR portion of the protein has been humanized and more preferably the entire binding protein has been humanized to enhance patient compatibility. In such embodiments it may be desirable to include at least one protein tag which can be, e.g., a detectably-labeled molecule suitable for diagnostic or imaging studies.

As will be described below, the present polyspecific binding molecules can be unmodified, or if desired, can be covalently linked to a desired molecule, e.g., drugs, toxins, enzymes or radioactive substances through a linked peptide linker sequence.

The polyspecific binding molecules of the present invention provide several significant advantages.

For example, preferred, polyspecific binding proteins are capable of associating an MHC-expressing target cell and an immune cell. That is, the present binding proteins preferably form a bridge that joins the immune cell to the MHC- or HLA-expressing cell. As noted, that association is believed to enhance recognition and facilitate damage to or killing of the target cell. In contrast, most prior immune system molecules and particularly bsFv molecules are not optimized to bind pMHC or pHLA complexes. Accordingly, the present molecules provide an effective means for killing target cells that express a pMHC or pHLA molecule.

Additionally, use of the present polyspecific binding proteins is believed to be associated with fewer adverse activities when compared to many prior immune molecules. As an illustration, many prior bsFv molecules have been reported to bind to shed TAAs. In contrast, preferred polyspecific binding molecules of this invention specifically bind TAAs in the context of MHC or HLA molecules, thereby substantially reducing or totally eliminating non-specific binding to the shed debris. Significantly, there has been much less concern in the field regarding any MHC and HLA shedding.

Further, the polyspecific binding molecules disclosed herein can bind a significantly wider spectrum of molecules than most prior recombinant immune molecules. In particular, there has been understanding that targetable antigens are often hidden inside cells making recognition and binding difficult. It is an object of the present invention to provide binding molecules that specifically bind these hidden antigens. For example, the polyspecific binding molecules include at least one sc-TCR (or functional fragment) that can bind antigens in the context of an MHC or HLA. Thus, the present binding molecules are capable of binding a large variety of antigens that are usually hidden inside cells. In contrast, most prior recombinant immune system molecules are not able to bind MHC- or HLA-presented antigens effectively.

The present invention provides still further advantages. For example, prior practice generally required extensive manipulation of TCR-related proteins (e.g., TCR receptors, TCR heterodimers, sc-TCRs), before significant amounts of protein could be obtained. In contrast, the polyspecific binding molecules of the present invention are fully soluble and can be isolated in significant quantities. Additionally, a wide variety of the polyspecific binding molecules can be presented for interaction with various immune system components such as superantigens or APCs.

Additionally, the single- and multi-chain polyspecific binding molecules include immunoglobulin chains that are readily isolated by standard immunological methods. Presence of these chains can usually facilitate detection, analysis and isolation of the binding molecules as discussed below.

In another aspect, the invention pertains to polynucleotides (RNA, mRNA, cDNA, genomic DNA, or chimeras thereof that include or consist of a sequence that encodes a single- or multi-chain polyspecific binding protein. In one embodiment, the polynucleotide includes sequence that encodes essentially all of the binding protein, e.g., as when the binding protein is a single-chain construct.

In another embodiment, the polynucleotides include a sequence that encodes a portion of the polyspecific binding protein and particularly part of certain multi-chain binding proteins discussed below. For example, a particular polynucleotide of this invention may encode an sc-TCR fused to an immunoglobulin heavy chain or suitable fragment thereof (e.g., an sc-TCR/Ig molecule). In this embodiment, the remaining part of the polyspecific binding protein can be provided in several ways. For example, it can be provided by a cell or extract thereof capable of synthesizing antibody molecules such as an antibody binding domain. The antibody or antibody-binding domain may be encoded by the cell genome or it may be encoded by an introduced DNA segment. Preferably, the cell will be an antibody-producing cell such as a hybridoma cell. Alternatively, the remaining part of the binding protein is provided by a second polynucleotide sequence that includes the DNA segment. In this embodiment, the binding protein is preferably constructed by contacting the encoded protein portions together under conditions conducive to forming the desired binding protein. As will be discussed below, the polyspecific binding proteins of this invention can be joined by one or a combination of strategies including cellular, genetic and chemical methods.

Particularly contemplated are DNA vectors that include or consist of the polynucleotides of this invention. Illustrative DNA vectors include those compatible with conventional prokaryotic or eukaryotic protein expression system. More specific examples of polynucleotides and DNA vectors.

The polynucleotides of the present advantage provide important advantages. For example, as will become apparent from the disclosure which follows, preferred polynucleotides of this invention include DNA segments that encode covalently linked scTCR and sc-Ab molecules. The DNA segments are preferably configured in a "cassette" format so that a segment encoding a sc-TCR or sc-Ab can be switched, as desired, with another segment encoding another scTCR or sc-Ab.

In another aspect, the present invention provides compositions and methods for selecting polyspecific binding proteins. More particularly, the compositions and methods can be employed to select sc-TCR and sc-Ab molecules with desired characteristics, thereby facilitating manufacture and use of polyspecific binding proteins that include these molecules.

In one embodiment, the invention provides recombinant bacteriophages that include at least one sc-TCR (or functional fragment) and at least one sc-Fv (or functional fragment) as fusion proteins. As will be discussed, the bacteriophages can be employed, e.g., to select sc-TCR and sc-Fv molecules for desired binding characteristics. Preferred are bispecific bacteriophages. The recombinant bacteriophages may sometimes be referred to herein as "polyfunctional" or "polyspecific" to denote binding by the sc-TCR and the sc-Fv fusion proteins. The recombinant bacteriophages can be derived from well-known filamentous "fd" phages although related phages may be used in some cases.

More particularly, the recombinant bacteriophages of this invention include a plurality of fusion proteins that each include: 1) at least one sc-TCR or functional fragment thereof fused to a first bacteriophage coat protein, or 2) at least one sc-Ab or functional fragment thereof fused to a second bacteriophage coat protein the same or different from the first bacteriophage coat protein. Preferred bacteriophage coat proteins are essentially full-length or may be fragments thereof provided that the fragment is sufficient to display the fused molecule. By "display" is meant that the protein fusion is part of the bacteriophage coat and is readily detectable on the bacteriophage by standard screening techniques such as those disclosed below.

In a related aspect, the invention provides a recombinant bacteriophage library that includes a plurality of recombinant bacteriophages in which each bacteriophage comprises a plurality of single-chain polyspecific binding proteins each covalently linked to a bacteriophage coat protein as a protein fusion, wherein each single-chain binding protein comprises: 1) one sc-TCR or functional fragment thereof fused to a first bacteriophage coat protein or fragment, or 2) one sc-Ab or functional fragment thereof fused to a second bacteriophage coat protein or fragment. More preferred recombinant bacteriophage libraries include bacteriophages that display bispecific binding proteins.

The recombinant bacteriophage libraries can be formatted to include a variety of TCR V chains and/or immunoglobulin variable chains. Accordingly, libraries can be used to select recombinant bacteriophages that display desired sc-TCR and sc-Ab molecules.

The recombinant bacteriophages of this invention can be isolated by a variety of conventional techniques. In one embodiment, there is provided a method for isolating the recombinant bacteriophages in which the methods include at least one and preferably all of the following steps:

a) introducing into host cells a first polynucleotide comprising a sequence encoding a first fusion protein comprising an sc-TCR covalently linked to a first bacteriophage coat protein or fragment, b) introducing into the host cells a second polynucleotide comprising
a sequence encoding a second fusion protein comprising a sc-Fv covalently linked to a second bacteriophage coat protein or fragment.

c) culturing the host cells in medium under conditions permitting propagation of bacteriophages and display of the fusion proteins; and d) isolating the recombinant bacteriophages from the host cell or the medium.

In a particular embodiment, the method further includes contacting an extract of the host cell or the cultured medium with a synthetic matrix capable of specifically binding one of the fusion proteins, and purifying the recombinant bacteriophage from the synthetic matrix to isolate the bacteriophage. In a more particular embodiment, the synthetic matrix includes an antibody fragment that is capable of specifically binding the recombinant bacteriophage. More specific bacteriophage isolation techniques are discussed below.

Additionally provided by the invention is a kit comprising the present recombinant bacteriophages which kit may also include suitable prokaryotic cells for propagating the bacteriophage and directions for using the kit. Also provided is a kit that includes the bacteriophage library discussed above.

The recombinant bacteriophages of this invention have additional uses and advantages. For example, the bacteriophages can be used in accord with standard screening techniques to facilitate analysis of a desired polyspecific binding molecule in vitro. More particularly, the recombinant bacteriophages can be used to assess whether a specific sc-TCR or sc-Ab such as a sc-Fv has capacity to recognize, bind and/or kill target cells of interest. Additional advantages include a relatively fast and straightforward procedure for making and testing bispecific sc-TCR/sc-Ab molecules; a short and simple purification process; and an accelerated method for testing large numbers of different hybrid molecules for efficacy in damaging or killing target cells (e.g., tumor killing).

The single- and multi-chain polyspecific binding proteins of this invention can be made as fully functional and soluble proteins by one or a combination of methods. In general, the methods involve cellular, recombinant DNA and chemical techniques, or combinations thereof.

For example, in one embodiment, there is provided a method for making a single-chain polyspecific binding protein comprising at least one sc-TCR or functional fragment thereof and at least one sc-Ab and particularly a sc-Fv or functional fragment thereof. The method includes at least one and preferably all of the following steps:

a) introducing into a host cell a DNA vector encoding a single-chain polyspecific binding protein of interest, b) culturing the host cell in media under conditions sufficient to express the single-chain polyspecific binding protein in the cell or the media; and c) isolating the single-chain polyspecific binding protein from the cell or media.

Additionally provided are methods for making a multi-chain polyspecific binding protein comprising at least one sc-TCR or functional fragment thereof and an antibody binding domain or functional fragment. In one embodiment of the method, the antibody-binding domain is a F(v). In particular, a cell or cell extract is used to form at least part of the multi-chain binding protein. More particularly, an antibody producing cell such as a hybridoma is employed. In one embodiment, the method includes at least one and preferably all of the following steps:

a) introducing into a hybridoma cell a DNA vector encoding at least one sc-TCR, preferably one sc-TCR (or functional fragment) covalently linked to an immunoglobulin constant heavy chain or fragment thereof, b) culturing the hybridoma cell in media under conditions conducive to forming a specific binding complex between the immunoglobulin constant heavy chain or fragment encoded by the DNA vector and immunoglobulin chains produced by the hybridoma; and c) purifying the multi-chain polyspecific binding protein from the hybridoma cells or media.

In a more specific embodiment, the method provides for a multi-chain polyspecific binding protein that includes an immunoglobulin variable light chain covalently linked to the sc-TCR, i.e., a bispecific binding protein.

The present invention provides additional methods for making the multi-chain polyspecific binding proteins. For example, in one embodiment, each chain of a desired binding protein is made independently, e.g., by recombinant DNA or chemical methods. Preferably, the binding protein further includes at least one joining molecule, preferably two joining molecules the same or different. In a particular embodiment, the method includes at least one and preferably all of the following steps:

a) providing a first sequence that includes at least one sc-TCR or functional fragment thereof covalently linked to a first joining molecule, b) contacting the first sequence with a second sequence that includes at least one sc-Fv or functional fragment thereof linked to a second joining molecule, wherein the contacting is under conditions sufficient to form a specific binding complex between the first and second joining molecules; and c) forming the multi-chain polyspecific binding protein. Preferably, the multi-chain polyspecific binding protein is bispecific.

More specific recombinant DNA and chemical methods for making the multi-chain polyspecific binding proteins are disclosed below.

As discussed, the present polyspecific binding proteins also have significant uses in vivo. For example, the binding proteins can be used to redirect the specificity of certain immune cells, e.g., to eliminate target cells such as virally-infected or tumor cells. In some instances, the tumor cells may also be virally-infected. As discussed, preferred use of the present binding molecules can increase damage or elimination of the target cells. Accordingly, the present invention can be used in vivo to kill target cells by enhancing immune system activation against those target cells. Preferred in vivo use of the present polyspecific binding molecules includes use in a mammal such as a rodent, primate or domesticated animal, and especially a human patient.

Thus, in one aspect, the invention provides methods for damaging or preferably killing a target cell comprising an MHC or HLA of interest. In one embodiment, the method includes at least one and preferably all of the following steps:

a) contacting a plurality of cells with a polyspecific binding protein, wherein the plurality of cells comprises immune cells comprising an antigen and target cells comprising the MHC or HLA, b) forming a specific binding complex (bridge) between the MHC or HLA on the target cells and the antigen on the immune cells sufficient to activate the immune cells; and c) killing the target cells with the activated immune cells. It will be appreciated that by the term "activated" is meant that the immune cells are capable of damaging or killing the target cell as determined, e.g., by cytokine and cytotoxicity assays described below.

If desired, the above-described method may be conducted in vitro such as in a cell culture dish.

The single- and multi-chain polyspecific binding proteins of this invention have additional uses in vitro and in vivo.

For example, preferred polyspecific binding molecules of this invention can be used in vitro or in vivo to detect and preferably form a bridge between target cells and immune cells. Formation of the bridge can be used to isolate cells expressing desired MHC, HLA or antigen markers.

The present polyspecific binding proteins also find use in the detection and analysis of MHC or HLA molecules and cell surface antigens. The present binding proteins can also be used for diagnostic purposes such as for the detection of immune system cells and especially T-cells with pathogenic properties. The present binding molecules can additionally be employed in functional, cellular and molecular assays, and in structural analysis, including X-ray crystallography, nuclear magnetic resonance imaging, computational techniques such as computer graphic display.

In another aspect, the present invention further provides treatment methods for reducing or eliminating presence of the target cells in a mammal. In particular, the methods include administering a polyspecific binding protein of this invention in a pharmaceutically acceptable formulation. If desired, the sc-TCR or sc-Ab portion of particular polyspecific binding molecule can be removed prior to or during the administration to facilitate a specific treatment method.

In a more particular embodiment, the treatment methods are employed to treat cancer and a viral infection. In particular, the methods include administering a therapeutically effective amount of at least one polyspecific binding protein of this invention to a mammal and especially a human patient. Preferably the amount is sufficient to treat the cancer and/or the viral infection. The methods may be used to treat an existing condition or may be used prophylactically as needed. The present treatment methods may be used alone or in combination with other therapies if desired.

Preferred treatment methods of the invention reduce or eliminate presence of specific target cells in a mammal, particularly a rodent or a primate such as a human. In one embodiment, the treatment methods include obtaining an sc-TCR or sc-Ab from the polyspecific binding molecule (e.g., by protease treatment). The sc-TCR or sc-Ab so obtained may be administered to the mammal instead of or in conjunction with the polyspecific binding molecule. For most applications involving animal use, it will be preferred to minimize undesired immune responses against the present binding molecules, e.g., by using immunoglobulin chains of a haplotype compatible with the animal being used.

BRIEF DESCRIPTION OF THE DRAWINGS

FIGS. 1A–1D are drawings showing single-chain T-cell receptor (sc-TCR) and single-chain Fv (sc-Fv) DNA constructs. (1A) DO11.10 sc-TCR construct, (1B) p149 sc-TCR construct, (1C) 145-2C11 sc-Fv, (1D) F23.1 scFv DNA construct.

FIG. 6 is a drawing showing preferred bispecific hybrid molecules pBISP/DO11.10 and pBISP/149.

FIG. 11 is a graph showing results of ELISA assays used to detect chimeric bispecific molecules. Capture Ab is goat anti-mouse-IgG2b (x-axis). Probe Ab is goat anti-hamster IgG.

FIGS. 21A–21B are drawings showing specific oligo-nucleotide primers (SEQ ID NOs: 16–43).

DETAILED DESCRIPTION OF THE INVENTION

Figure 2A:
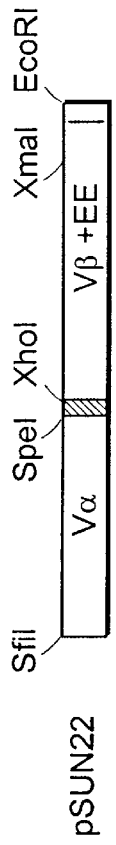
FIGS. 2A–2E are drawings showing sc-TCR inserts of various vectors: (2A) pSun22; (2B) pSun23; (2C) pSun21; (2D) pSun19; and (2E) pSun20.
Figure 2B:
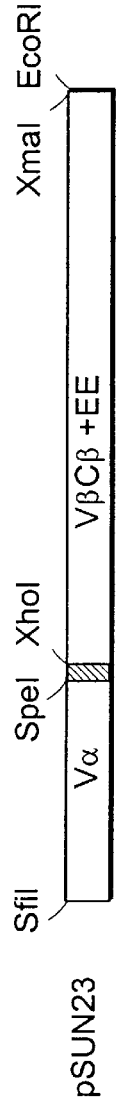
Figure 2C:
Figure 2D:
Figure 2E:
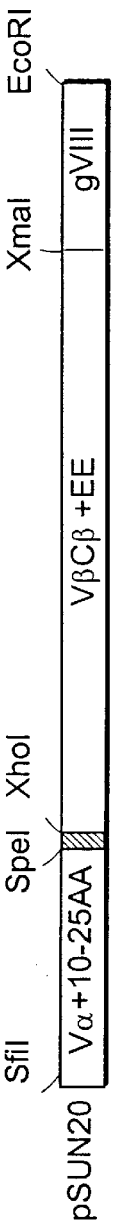

As summarized above, the present invention features, in one aspect, single-chain polyspecific binding proteins and methods for making and using the proteins. Preferred use of the present binding molecules includes damaging or eliminating (killing) MHC-expressing target cells in vitro or in vivo. Further provided are highly useful recombinant bacteriophages and methods of using same that can be used to select for desired binding molecules.

As used herein, the term "polyspecific binding protein" or similar phrase means a single-chain or multi-chain molecule that preferably includes 1) a binding domain capable of binding an MHC or HLA complex, preferably a cell target expressing an pMHC or pHLA (or portion thereof and 2) an antibody binding domain capable of binding an antigen target, preferably an antigen or epitope portion thereof expressed on the surface of an immune cell. Preferably the pMHC or pHLA portion is capable of being specifically bound by a TCR and the antigen portion is capable of being specifically bound by an antibody. In preferred embodiments, the antigen is a cell surface antigen that is indicative of the immune cell. In additionally preferred embodiments, each of the binding domains is sufficient to bind the pMHC or pHLA, and antigen targets at alternate times or at the same time. As discussed herein, the binding domains may be present on the same chain (i.e. on a single-chain) or the binding domains may be present on more than one chain (i.e. on a multi-chain and particularly from between about 2 to 4 chains with 2 chains being preferred.)

By the term "antibody binding domain" is meant an antibody binding site comprising at least one and preferably two immunoglobulin variable chains that are capable of specifically binding the antigen or epitope thereof For example, in a preferred embodiment, the antibody binding domain is a single-chain construct (sc-Ab) and includes a single immunoglobulin variable region ($V_L$ or $V_H$); two or more variable regions ($V_L+V_H$; $V_L+V_L$; or $V_H+V_H$); or the complementary determining regions thereof. A more particular example of a suitable sc-Ab antibody binding domain is a sc-Fv molecule. In another embodiment, the antibody binding domain further includes an immunoglobulin constant light chain (Ig-$C_L$) and/or an immunoglobulin heavy chain (Ig-$C_H$). Preferred examples include, but are not limited to, Fab, F(v), Fab' and F(ab')2 molecules. More specific antibody binding domains are discussed below.

In a more particular embodiment, the polyspecific binding protein is a single-chain construct that includes at least one sc-TCR (or functional fragment) and at least one sc-Ab and especially a sc-Fv (or functional fragment). The single-chain polyspecific binding protein can include from between about 1 to 5 sc-TCR molecules and/or from between about 1 to 5 sc-Fv molecules with one sc-TCR and one sc-Fv being generally preferred for most applications. In embodiments in which the binding protein includes at least one sc-TCR or sc-Fv, the molecules may be linked in tandem and are preferably separated from each other by suitable peptide linker sequences.

More particular polyspecific binding molecules of this invention are bispecific binding molecules and include one sc-TCR and one sc-Ab and particularly one sc-Fv molecule. In this embodiment, the sc-TCR and the sc-Fv are separated by a suitable peptide linker sequence.

In general, the present polyspecific binding proteins include pre-determined binding specificities. That is, choice of a particular sc-TCR or antibody binding domain will be guided by recognized parameters such as intended use and the target cells and immune cells of interest. In most instances, the binding specificities will be different as determined by specific binding assays described below. However, in some embodiments, it will be useful to select binding domains with the same or closely related binding specificities. Methods for selecting desired binding domains and for choosing appropriate sc-TCR and sc-Ab molecules are described below.

As discussed, in one embodiment, the present polyspecific binding proteins include an scTCR or functional fragment thereof that binds pMHC- or pHLA-expressing target cells. In a more particular embodiment, the scTCR is chosen to specifically bind a class I or class II pMHC molecule (or an pHLA antigen) on the target cell. More specific disclosure relating to sc-TCR molecules including methods for making and using same have been disclosed in the pending U.S. application Ser. No. 08/813,781, filed on Mar. 7, 1997 and Ser. No. 08/943,086, filed on Oct. 2, 1997. The pending U.S. application Ser. Nos. 08/813,781 and 08/943,086 are incorporated herein by reference.

As used herein, the term sc-TCR "functional fragment" means a portion of a full-length sc-TCR (i.e., comprising full-length V chains) that is capable of specifically binding at least about 70% and preferably at least about 80%, 90%, 95% up to 100% or more of an MHC or HLA when compared to a full-length sc-TCR. A full-length sc-TCR is defined as molecule with a full-length V-α and V-β chain. Assays for detecting specific binding are discussed and include flow cytometry and Bizarre.

As mentioned previously, the sc-TCR includes TCR V-α and V-β chains covalently linked through a suitable peptide linker sequence. For example, the V-α chain can be covalently linked to the V-β chain through a suitable peptide linker sequence fused to the C-terminus of the V-α chain and the N-terminus of the V-β chain. The V-α and V-β chains of the sc-TCR fusion protein are encoded by nucleic acids generally about 200 to 400 nucleates in length, preferably about 300 to 350 nucleotides in length, and will be at least 90% indentical, and preferably 100% indentical to the V-α and V-β chains of a naturally-occuring TCR. By the term "indentical" is meant that the amino acids of the V-α or V-β chain are 100% homologous to the corresponding naturally-occurring TCR V-β or V-α chains. See Examples 1–3 below and the pending U.S. application Ser. Nos. 08/813,781 and 08/943,086 for more specific disclosure relating to sc-TCR V chains.

As mentioned previously, the V-α chain of the sc-TCR molecule can further include a TCR C-β chain or fragment thereof fused to the C-terminus of the V-β chain. Further, the V-α chain can include a TCR C-V-α chain or fragment thereof fused to the C-terminus of the V-α chain and the N-terminus of the peptide linker sequence. Generally, in those sc-TCR fusion proteins including a C-β chain fragment, the fragment will have a length of approximately 50 to 126 amino acids and will usually not include the last cysteine residue at position 127. For those fusion proteins comprising a C-α chain, the length can vary between approximately 1 to 90 amino acids (i.e. the C-α chain up to but not including the final cysteine). For example, in one embodiment, the fusion protein includes a C-α chain fragment between about 1 to 72 amino acids starting from amino acid 1 to 72. In another embodiment, the C-α chain fragment is between about 1 to 22 amino acids starting from the first amino acid to 22 (leucine). The C-α chain fragment typically does not include any cysteine resides except the $C_{4\,90}$ variant which includes two cys residues. In most cases, choice of Cα and Cβ chain length will be guided by several parameters including the particular V chains selected and intended use of the particular polyspecific binding protein. See the following discussion and examples 1–2 below for more specific disclosure relating to sc-TCR C-β and C-α chains. See also the pending U.S. application Ser. Nos. 08/813,781 and 08/943,086.

As disclosed in the pending U.S. application Ser. No. 08/943,086, it is possible to facilitate expression of fully soluble and functional sc-TCR fusion proteins by adding an Ig-$C_L$ chain or suitable Ig-$C_L$ fragment thereof. More specifically, Ig-$C_L$ chain or chain fragment is covalently linked to the sc-TCR molecule, e.g., to the C-terminus of the V-β chain or C-β fragment. Although typically not preferred, it is possible to covalently link the Ig-$C_L$ or fragment thereof to the N-terminus of the V-α chain. If desired, the Ig-$C_L$ chain can be removed prior to incorporation into a polyspecific binding molecule.

As discussed above, the sc-TCR of a polyspecific binding protein may be provided in a variety of suitable formats. For example, the sc-TCR may be provided with e.g., two peptide linker sequences, where the first peptide linker sequence is fused between the C-terminus of the V-α chain and the N-terminus of the V-β chain. The C-terminus of the V-β chain can be fused to the N-terminus of a C-β chain fragment if desired. The second peptide linker is then fused to the C-terminus of the V-β chain or C-β chain fragment and the N-terminus of, e.g., an effector or protein tag.

In other illustrative embodiments, the sc-TCR of the polyspecific binding molecule includes a V-β chain fused to the V-α chain through a suitable peptide linker in which the C-terminus of the V-β chain or C-β chain fragment thereof and the N-terminus of the V-α chain are covalently linked.

The aforementioned sc-TCR molecules are further fused to a peptide linker sequence which sequence is typically further covalently linked to an antibody binding domain of interest. Preferred single-chain polyspecific binding proteins include covalently linked in sequence an sc-TCR, a peptide linker sequence, and a sc-Ab such as a sc-Fv.

As disclosed in the pending U.S. application Ser. Nos. 08/813,781 and 08/943,086, it is possible to make and use a variety of sc-TCR molecules. In particular, it is generally preferred that the sc-TCR include Vα,β chains for which a full-length or substantially full-length coding sequence is readily available. Methods for obtaining full-length TCR V chain sequences from cell sources are well known. Alternatively, the Vα,β chain regions can be obtained by PCR amplication of publicly available Vα,β chains. Exemplary Vβ gene sequences include Vβ8.1, Vβ6.1, Vβ5.1, Vβ5.2, Vβ5.3, Vβ2.1, and Vβ2.3 gene sequences. See Abe et al. (1992) *PNAS (USA)* 89: 4066; Wang, et al., 1993); *PNAS (USA)* 90: 188; Lahesma et al. (1993) *J. Immunol.* 150: 4125; Kotzin, et al., (1991) *PNAS (USA)* 88: 9161; Uematsu, et al. (1991) *PNAS (USA)* 88: 8534. See also, Kabat, E. A., et al. (199 1) *Sequences of Proteins of Immunological Interest*, ($5^{th}$ Ed.) Public Health Science, NIH, and Chotia, C. et al., (1988) *EMBO J.* 7:3745 for additional TCR V-β, Vα chain sequences.

In addition, Examples 1–3 below provide oligonucleotide primers for PCR amplifying specific V-α and V-β chains. See also, FIGS. 21A–21B for examples of oligonucleotide primers that can be used to isolate the TCR V chains.

In cases where it is desired to obtain TCR V chains from a biological source, a desired TCR can be identified by conventional immunological methods including use of TCR-specific antibodies, which predominantly bind, and preferably are specific for, an epitope of the TCR V region. Typically, surface expression can be detected by using known techniques such as fluorescence microscopy, flow cytometry, or immunochemistry. A number of antibodies which specifically bind TCR variable regions are known. See e.g., published PCT application WO 90/06758.

The DNA or RNA of the detected TCR can be probed directly, or preferably after PCR amplification, by specific hybridization with oligonucleotide probes for the various TCR gene families, using hybridization methods well-known in the field. Generally, high stringency nucleic acid hybridization conditions will be performed. As used herein the term "high stringency hybridization" means nucleic acid incubation conditions approximately 65° C. in 0.1×SSC. See Sambrook, et al., infra. The TCR DNA sequence or desired portion thereof can be obtained directly from the amplified DNA or RNA and can be subcloned into a suitable vector as desired.

Other methods are known for obtaining TCR V region DNA. For example, a desired TCR comprising V region genes can be identified by sequencing the TCR or preferably a portion thereof corresponding to the V region. The DNA sequence can be determined, e.g., after cloning DNA into a suitable sequencing vector as are known in the field or by first determining the protein sequence of at least part of the TCR and determining the DNA sequence. It will be readily apparent to those skilled in this field that the above-mentioned manipulations as well as others known to the artisan can be employed to successfully identify a desired TCR and to obtain the V region genes from that TCR so that a single-chain Vαβ construct can be made.

More specifically, when it is desired to obtain TCR V region DNA from a biological source, a DNA segment encoding the desired V-α and V-β chain can be obtained from cells such as T-cell hybridomas or cytotoxic T-cells (CTLs). The T-cells (e.g., $T_S$, $T_C$ or $T_H$ cells) can be obtained in vivo, or the T-cells can be cultured T-cell hybridoma(s) (e.g., D10 or B12 cell lines). See Examples 1–3 which follows and the pending U.S. application Ser. Nos. 08/813, 781 and 08/943,086. CTLs can be uninduced or can be associated with a pathogenic immune system response in a rodent (e.g., mouse, rat, rabbit) or primate (e.g. human or chimpanzee). For example, CTLs or other T-cells can be derived from patients suffering from or suspected of having Lyme disease, Kawasaki disease, leprosy, cancer (i.e. immune responses against tumor associated antigens such as CEA), or an autoimmune disorder, particularly those associated with transplantation rejection, multiple sclerosis, insulin dependent diabetes, rheumatoid arthritis, and allergies; or an infectious disease, particularly an infectious disease involving an RNA or DNA virus. Particular viruses of interest include the human immunodeficiency viruses (HIV), cytomeglovirus (CMV), influenza, hepatitis, pox virus, Epstein Barr, adenovirus or polyoma viruses. Exemplary sources of CTLs are antigen-specific CTLs and TILs isolated from patients with established carcinomas and melanomas (see e.g., Cox A. et al. *Science* (1994) 264: 716; Rosenberg, S. A. et al. *N. Eng. J. Med.* (1988) 319: 1676; Kawakami, Y. et al., *J. Exp. Med.* (1994) 180: 347); Kawakami, Y. et al. *PNAS* (1994) 91:6458).

As mentioned previously with respect to obtaining V-α and V-β chains from cell sources, several alternative procedures can be used to prepare nucleic acids isolated therefrom. More particularly, to prepare V-α and V-β chain DNA, mRNA is isolated from those cells demonstrating a desired TCR binding specificity. Such methods generally include use of a suitable PCR protocol using first-strand cDNA template made from the mRNA. Standard recombinant techniques can then be employed to make the desired α and β chains. The DNA segment encoding the desired V-α and V-β chains is then modified to include a suitable peptide linker sequence and protein tag(s), if desired.

Generally, a DNA oligonucleotide primer for use in the PCR methods will be between from about 12 to 50 nucleotides in length preferably from between about 20–25 nucleotides in length. The PCR oligonucleotide primers may suitably include restriction sites to add specific restriction enzyme cleavage sites to the PCR product as needed, e.g., to introduce a ligation site. Exemplary primers are provided in the Examples and Drawings which follow. The PCR products produced will include amplified V-α and V-β chain sequences and can be modified to include, as desired, ribosome binding, leader and promoter sequences for optimal expression of the fusion protein.

A DNA segment encoding a desired sc-TCR molecule can be made in significant quantities (milligram quantities per gram cells) in accord with methods disclosed below and in the pending U.S. application Ser. No. 08/943,086.

More particular sc-TCRs used to make the present polyspecific binding proteins include those sc-TCRs with V-α and Vβ chains derived from a mammal. Examples include primates, particularly human and chimpanzees; rodents, e.g., immunologically naive mice such as nude mice or mice which include a transgene capable of expressing an HLA-A2 antigen complex (Vitiello, A. et al., *J. Exp. Med.*, (1991) 175, 1002). Particular humans of interest include those suffering from any of the previously mentioned pathologies, such as an autoimmune disorder. Chimeric constructs comprising V-α and V-β DNA sequences derived from different mammals can be constructed in accordance with known methods and are also within the scope of the present invention.

It is preferred that a peptide linker sequence used to make the sc-TCR be capable of effectively positioning the V-α and V-β chains to form a ligand binding pocket. The sc-TCR is thus preferably capable of specifically binding a desired ligand such as a superantigen or peptide antigen in the context of an MHC/HLA peptide complex, or a small molecule. In some embodiments of the present invention, the polyspecific binding molecules may be used to compete with naturally-occurring TCRs on the surface of T-cells. By "compete" is meant that the soluble fusion protein is able to bind the ligand at a level which is equal to, or in some instances exceeds the specific binding affinity of the TCR for the same ligand. For example, in accordance with methods described below and in the pending U.S. application Ser. No. 08/943,086, the sc-TCR fusion protein (or sc-TCR molecule derived therefrom) can exhibit a binding affinity which is about equal or up to approximately 2 to 10 fold higher than the naturally-occurring TCR. Exemplary binding assays are disclosed herein and include standard Western blotting assays and surface plasmon resonance assays disclosed below and in the pending U.S. Application.

In general, the peptide linker sequences disclosed herein (sometimes referred to as a polypeptide linker, spacer sequence, peptide linker or related term) are selected to maximize binding interactions between a particular polyspecific binding molecule and its binding target or targets. For example, a peptide linker sequence suitable for the sc-TCR is preferably selected so that the sc-TCR forms a specific binding site which resembles that of a naturally occurring TCR V-α and V-β chain. Additional peptide linker sequences such as those used for making sc-Ab molecules are also selected to optimize binding to specific antigens. In single-chain constructs, peptide linker sequences fusing the sc-TCR to the sc-Ab are selected typically maximize interaction between the sc-TCR, the sc-Ab, and respective targets of those binding units.

More particularly, the peptide linker sequence separating the Vα,β chains of the sc-TCR preferably flexibly positions the V-chains in a pocket that is capable of specifically binding ligand. Preferred ligands in this instance are antigens and especially peptide ligands presented in the context of an MHC. As will be explained more fully below, in the discussion that follows ligand binding to the sc-TCR can be used to modulate T-cell activity as determined by specific assays described below. Exemplary of such assays include in vitro assays involving sequential steps of culturing T-cells expressing a TCR, contacting the T-cells with the sc-TCR protein (or sc-TCR obtained therefrom) under conditions which allow binding between the TCR and the ligand, and then evaluating whether the soluble fusion protein is capable of modulating activity of the T-cells.

In a more specific embodiment, the polypeptide linker sequence comprises from about 7 to 25 amino acids, more preferably from about 10 to 20 amino acids, still more preferably from about 12 to amino acids. The linker sequence is typically flexibly disposed in the fusion protein so as to position the V-α and V-β chains in a configuration which provides for specific binding of a desired ligand such as a peptide antigen. The linker preferably predominantly comprises amino acids with small side chains, such as glycine, alanine and serine, to provide optimal flexibility. Preferably, about 80 or 90 percent or greater of the linker sequence comprises glycine, alanine or serine residues, particularly glycine and serine residues.

Preferably, the linker sequence does not contain any proline residues, which could inhibit flexibility. The linker sequence is suitably attached to the C-terminus of the V-α chain and the N-terminus of the V-β chain of a fusion protein. See Examples 1–3 and 5 below for disclosure related to making and using specific peptide linker sequences.

More specifically, suitable peptide linker sequences in accord with the invention include between from about 5 to 25 amino acid sequences such as the (GGGGS)$_4$ sequence (i.e., Gly Gly Gly Gly Ser)$_4$ (SEQ ID NO: 1). Preferably, a selected peptide linker sequence is covalently linked between the C-terminal residue of the V-α chain, and the first amino acid of the V-β chain of the sc-TCR. Several polypeptide linker sequences have been disclosed as being acceptable for use in joining antibody variable regions (see M. Whitlow et al., *Methods: A Companion to Methods in Enzymology*, 2:97–105 (1991)). Many of those reported peptide linker sequences can be used to make the sc-TCR.

Alternatively, other suitable linker sequences can be readily identified empirically. For example, a DNA vector including a DNA segment encoding a fusion protein that includes the linker sequence can be cloned and expressed, and the fusion molecule tested to determine if the molecule is capable of binding antigen. An exemplary assay is a conventional antigen binding assay such as those disclosed in Harlow and Lane, supra. Alternatively, the expressed fusion protein comprising the linker sequence can be tested for capacity to modulate the activity of a T-cell as determined by assays disclosed herein. Suitable size and sequences of linker sequences also can be determined by conventional computer modeling techniques based on the predicted size and shape of the fusion protein. Exemplary peptide linker sequences are those which include suitable restriction sites (e.g. XhoI and SpeI) at the ends of the polypeptide linker sequence between the Vα and V-β chains.

Although the foregoing discussion has focused on selection of suitable sc-TCR peptide linker sequences, it will be understood that similar considerations can be used to select other peptide linker sequences useful for making the polyspecific binding molecules of this invention. Additional peptide linker sequences include those that are used to make certain antibody binding domains and particularly the sc-Ab, as well as peptide linker sequences used to join the sc-Ab to the sc-TCR in single-chain constructs.

In particular, preferred peptide linkers for making sc-Ab molecules and especially sc-Fv molecules are usually helical in structure. In general, such peptide linker sequences facilitate proper folding of the sc-Fv and can enhance the solubility of the sc-Fv and the polyspecific binding protein. More preferred peptide linker sequences include from between about 5 to 25 amino acids and preferably from between about 10 to 25 amino acids. More specific disclosure relating to suitable sc-Fv peptide linker sequences can be found in U.S. Pat. No. 5,637,481 to Ledbetter et al. the disclosure of which is incorporated by reference.

More preferred sc-Fv peptide linker sequences include the following peptide sequences: (G$_4$S)$_3$(i.e. Gly Gly Gly Gly Ser)$_3$ (SEQ ID NO. 2) and (G$_4$SA$_4$PG$_4$S) (i.e. Gly Gly Gly Gly Ser Ala Pro Gly Gly Gly Gly Ser) (SEQ ID NO. 3). See FIGS. 1A–B and Examples 4,5 below.

Preferred peptide linker sequences for joining the sc-TCR to the sc-Fv include can be the same or closely related to those peptide linker sequences used to make the sc-TCR. More preferred are peptide linker sequences having the following sequences: (G$_4$S)$_4$ (SEQ ID NO. 1) and VNAKT-TAPSVYPLEPVSGSSGSG (SEQ. ID NO. 4). See also FIG. 6 and Example 7 below.

The sc-TCR of the present binding molecules can be prepared as discussed above, as well as the examples which follow. See also the pending U.S. application Ser. Nos. 08/813,781 and 08/943,086. Generally, DNA coding for a desired V-α or V-β chain can be obtained from a suitable source such as a T-cell, T-cell hybridoma line, or publicly available V-α and V-β chain sequence as described previously. The DNA can be amplified by PCR, cloning or other suitable means. For example, DNA encoding a desired V-α chain can be cloned into a suitable vector, followed by cloning of DNA encoding a desired V-β chain and a suitable single chain linker sequence to produce a desired sc-TCR. As disclosed previously, in some cases the sc-TCR will include a DNA encoding a C-α and/or C-β chain fragment. In some instances it may be useful to further fuse an Ig-C$_L$ chain or fragment to the sc-TCR e.g., the murine or human C$_K$ chain or suitable C$_K$ chain fragment. As noted previously, DNA encoding the C$_K$ chain can be PCR amplified and ligated to DNA encoding the sc-TCR. Alternatively, the C$_K$ chain can be included in a DNA vector such as those disclosed by Near, et al., infra. The DNA segment encoding the fusion protein is then introduced into the DNA vector. The DNA vector is then expressed in a host cell and fusion protein harvested and purified if desired.

Illustrative sc-TCRs are generally encoded by a DNA segment including covalently linked in sequence: promoter/leader sequence/V-α chain/single-chain linker sequence/V-β chain; promoter/leader sequence/V-α chain/single-chain linker sequence/V-β chain, C-β chain fragment; promoter/leader sequence/ V-α chain, C-α chain/single chain linker sequence/V-β chain/C$_K$ chain; or promoter/leader sequence/ V-α chain, C-α chain fragment/single-chain linker sequence/V-β chain, C-β chain fragment. Additional sc-TCR molecules are as described above except that a C$_K$ chain is fused to the DNA segment. The DNA vectors encoding the sc-TCR proteins are introduced into desired cells, including those specific expression systems disclosed herein, for soluble expression of the fusion protein.

As discussed, the single-chain variable regions of the present binding molecules can be derived from nearly any suitable TCR or immunoglobulin variable region. With respect to the TCR portion of the present binding molecules, suitable Vα,β chains will be those for which there is an increase in gene expression following immunological induction. Methods for assaying an increase in TCR V chain expression are known (see e.g., Hafler, D. A. et al. *J. Exp. Med.* 167: 1313 (1988); and Mantgazza R., et al. *Autoimmunity* 3, 431 (1990)).

Additionally specific sc-TCR molecules include those molecules capable of binding known or yet to be discovered TAAs. Illustrative TAAs include p53 and Her-2 Neu.

As also discussed, the present polyspecific binding molecules also include an antibody binding domain such as a sc-Ab and particularly a sc-Fv or functional fragment thereof. As also discussed, methods of making and using various sc-Fv molecules have been described. See e.g., the U.S. Pat. No. 5,637,481; Jost, C. R. et al. supra, and Lindhofer, H. et al. (1996), supra.

More particular sc-Ab molecules generally include immunoglobulin chains that are capable of specifically binding antigen. The immunoglobulin chains may include full-length immunoglobulin chains, e.g., a full-length V$_L$ and V$_H$ chain; or may include a functional fragment of one or both full-length immunoglobulin chains. The term "functional fragment" as used with respect to a sc-Ab means a portion of the full-length immunoglobulin chain making up that sc-Ab that is capable of specifically binding at least about 70% and preferably at least about 80%, 90%, or 95% up to about 100% of a specific antigen when compared to the full-length immunoglobulin chain. Specific binding can be quantitated by a variety of techniques such as a Western blot or other suitable antibody binding assay as described below.

More specific examples of an antibody binding domain in accord with the invention include, but are not limited to, (1) a single variable region of an antibody ($V_L$ or $V_H$) 2) two or more single-chain variable regions (e.g. $V_L+V_H$; $V_L+V_L$; or $V_H+V_H$) or the complementary determining region (CDR) thereof. Each variable region fragment ($V_L$ or $V_H$) is preferably encoded by $V_L+J_L$ or by $V_H+D_H+J_H$ sequences and composed of approximately 100 amino acids. Within these sequences are three regions of hypervariability called complementarity determining regions (CDR) that appear to contain the amino acids that line the antibody's combining site. The CDRs are interspersed in four regions of lower variability called framework regions (FR).

In one embodiment, the antibody binding domain of a polyspecific binding molecule can be formed by the association of $V_L$ and $V_H$ polypeptides into a β-pleated sheet conformation, with the CDR regions contained at, or near, the loops between strands. Occasionally, the $V_L+V_L$ pairs or the $V_H+V_H$ pairs or the $V_L$ or $V_H$ alone can bind antigen.

In a more preferred embodiment, the antibody binding domain is a sc-Ab and particularly a sc-Fv including at least one and preferably one of the following: (1) a $V_L$ chain and a $V_H$ chain; (2) a $V_L$ chain and a $V_L$ chain; (3) a $V_H$ chain and a $V_H$ chain; (4) a single $V_L$ chain; or (5) a single $V_H$ chain. The binding domain may include immunoglobulin chains of any suitable isotype, e.g., IgG or IgM.

In embodiments in which the polyspecific binding region includes an antibody binding domain that exists as two variable regions linked as a single chain protein such as a sc-Fv (e.g., $V_L+V_H$; $V_L+V_L$; $V_H+V_H$) the single chain protein will preferably include a polypeptide linker sequence to link the two variable domains together. A variety of peptide linkers are known to be suitable for making sc-Fv constructs. See e.g., Huston, J. S. (1988) *PNAS (USA)* 85:5879; and Pluckthorn, A. (1992) *Immunological Rev.* 103:151. A specifically preferred linker has the following general formula (Gly4Ser)$_n$ in which n is from about 2 to 5 and preferably about 3.

A variety of immunoglobulin $V_H$ and $V_L$ chains have been described at the nucleic acid and protein levels. See, e.g. Davis in *Fundamental Immunology*, (1993) supra, Kabat E. A., supra; U.S. Pat. No. 5,637,481; Jost, C. R. et al. supra, and Lindhofer, H. et al. (1996), and the Brookhaven Protein Data Bank (Brookhaven Protein Data Base, Chemistry Dept. *Brookhaven National Laboratory*, Upton, N.Y. (1973).

As mentioned previously, a variety of sc-Fv constructs have been reported. The constructs can be used in accord with the invention to make a wide spectrum of polyspecific binding proteins. See generally, Pastan, I and Fitzgerald D., (1991) *Science* 254:I173; Webber, et al., *Molecular Immunol.* (1995), 32:249; and published PCT application Nos. WO96/05228 and WO97/2891 for disclosure relating to making and using single-chain antibodies.

More specific sc-Fv molecules are those capable of specifically binding cell surface targets such as glycoproteins and lipoproteins. Examples of particular glycoproteins include, but are not limited to, CD3/TcR and CD28. See Gilliland L. K. et al., (1996) *Tissue Antigens* 47:1 for disclosure relating to generating and characterizing sc-Fv molecules that bind these molecules and other surface molecules. Additional specific sc-Fv constructs have been disclosed in Colcher, D. et al. (1990) *J. Nat. Cancer Inst.* 82:1191; and Yokota, T., et al. (1992) *Cancer Res.* 52:3402).

Additional sequence information relating to specific sc-TCR and sc-Ab chains is available from the National Center for Biotechnology Information (NCBI)-Genetic Sequence Data Bank (Genebank) at the National Library of Medicine, 38A, 8NO5, Rockville Pike, Hethesda, Md. 20894. Genbank is also available on the internet. See Benson, D. A. et al. (1997) *Nucl. Acids. Res.* 25:1 for a description of Genbank.

The Ig-$C_L$ chain of a polyspecific binding protein of this invention is κ- or λ-type immunoglobulin light chain region. The κ-type immunoglobulin light chain constant region will sometimes be referenced herein as "$C_κ$ chain", whereas the λ-type immunoglobulin constant chain light chain region will often be referred to as "$C_λ$ chain". For example, the Ig-$C_L$ chain can be a $C_κ$ chain or a suitable fragment thereof such as those disclosed below. In addition, an Ig-$C_H$ chain of the polyspecific binding protein can be $μ$, $δ$, $γ$, $α$, or $ε$ type as desired. Preferably the amino acid sequences of the immunoglobulin heavy and light chains are known.

As noted, the present polyspecific binding molecules are fully functional and soluble. By the term "fully functional" or similar term is meant that the binding molecules can specifically bind other molecules for which binding is intended. More specifically, a binding molecule of this invention is fully functional if the sc-TCR part of the molecule can specifically bind an pMHC or pHLA (or a portion thereof). The term also means that the sc-Fv part of the binding molecule can specifically bind an antigen or portion thereof. Assays for detecting specific binding between a polyspecific binding molecule of interest and the pMHC (pHLA) or the antigen include Western blots and other standard assays such as those disclosed below.

By the term, "specific binding" or a similar term is meant a molecule disclosed herein which binds another molecule, thereby forming a specific binding pair. However, the molecule does not recognize or bind to other molecules as determined by, e.g., Western blotting ELISA, RIA, mobility shift assay, enzyme-immuno assay, competitive assays, saturation assays or other protein binding assays know in the art. See generally, Ausubel, et al infra; Sambrook, et al, infra; Harlow and Lane, supra and references cited therein for examples of methods for detecting specific binding between molecules.

By the term "fully soluble" or similar term is meant that the fusion protein is not readily sedimented under low G-force centrifugation from an aqueous buffer e.g., cell media. Further, a specific polyspecific binding molecule of this invention is soluble if can remain in aqueous solution at a temperature greater than about 5–37° C. and at or near neutral pH in the presence of low or no concentration of an anionic or non-ionic detergent. Under these conditions, a soluble protein will often have a low sedimentation value e.g., less than about 10 to 50 svedberg units. Aqueous solutions referenced herein typically have a buffering compound to establish pH, typically within a pH range of about 5–9, and an ionic strength range between about 2 mM and 500 mM. Sometimes a protease inhibitor or mild non-ionic detergent is added and a carrier protein may be added if desired such as bovine serum albumin (BSA) to a few mg/ml. Exemplary aqueous buffers include standard phosphate buffered saline, tris-buffered saline, or other known buffers and cell media formulations.

Conventionally, there are several means for linking the polyspecific binding molecules disclosed herein including cellular, genetic, chemical and biochemical. methods. As will be appreciated, certain polyspecific binding molecules of this invention can be joined (crosslinked) by chemical cross-linking; natural cross-linking by disulfide bonds; natural association without disulfide bonds; and connecting by a genetically encoded peptide linker (Bird, R. E., et al. (1988) *Science* 242; Huston et al., supra). For example, coupling between desired polyspecific binding molecules will include standard protein coupling reactions such as those generally described in Means, G. E. and Feeney, R. E. (1974) in *Chemical Modification of Proteins*, Holden-Day. See also, S. S. Wong (1991) in *Chemistry of Protein Conjugation and Cross-Linking*, CRC Press.

Additionally, it will be appreciated that the polyspecific binding complexes of the invention can be modified in several well-known ways to suit intended uses. For example, the complexes can be disulfide-stabilized in accordance with known methods see e.g., the published PCT application no. WO/29350.

The present binding molecules can also be made by employing inert polymers called dendrimers. In a more specific embodiment, a particular dendrimer, known as the Janice face dendrimer, can be used to join or couple together portions of the present binding molecules. In one specific embodiment of this invention, the sc-Fv molecule can be made to include a C-terminal cysteine residue that can be used to cross-link the antibody to the dendrimer particularly through disulfide bonds. The scTCR would then be coupled to the dendrimer through free amine groups. A preferred resulting product is a stable polyfunctional dendrimer molecule. See Example 19 below.

As discussed above, the present invention features multi-chain polyspecific binding protein comprising at least one sc-TCR and an antibody binding domain. In one embodiment, the binding protein is represented by the following general formula:

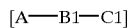

[A═B1─C1]

wherein,
a) A represents an antibody binding domain or functional fragment thereof,
b) B1, B2 are each independently a joining molecule the same or different,
c) C1, C2 are each independently —H or a protein tag; and
d) D represents at least one sc-TCR molecule or functional fragment thereof.

With respect to the formula provided above, a single line represents a covalent bond (e.g., a peptide bond), whereas a double line represents one or more covalent bonds, e.g., a disulfide bond such as those linking immunoglobulin heavy chains; or the double line represents hydrogen bonds. The brackets indicate flexibility in the sequential arrangement of the bracketed molecules (i.e., subunits). Thus, the order of the subunits is not important so long as each subunit performs the function for which it is intended.

In the formula shown above, the subunits A, B1, B2, C1, C2 and D each independently represent preferably one or a plurality of molecules. In instances where A or D represents a plurality of molecules, each molecule will preferably be attached to the same type of molecule (e.g., sc-TCR fused to another sc-TCR, sc-Fv fused to another sc-Fv). Preferably each molecule in the plurality is spaced from another by a suitable peptide linker sequence. The number of linked molecules will vary depending on intended use but will generally be from between about 2 to 10, preferably from about 2 to 5, more preferably 2 of such molecules, and most preferably 1 molecule. Each of the subunits described above can be fused directly to another subunit or it may be spaced therefrom by a suitable peptide linker, e.g., to enhance flexibility or binding affinity.

In a particular embodiment of the multi-chain polyspecific binding molecule represented above, A represents an F(v) or sc-Fv molecule; D represents a sc-TCR molecule, and each of C1 and C2 is —H.

A variety of joining molecules can be used in accord with the present invention. For example, in one embodiment, each of B1, B2 in the above formula can represent an immunoglobulin chain or suitable fragment thereof capable of forming a specific binding complex as determined, e.g., by RIA, Western blot or other suitable binding assay. In a more particular embodiment, each of B1 and B2 is derived whole or in part from an immunoglobulin heavy chain. In this embodiment, the joining molecules can be the same or different class (IgG, IgA, IgM, IgD, or IgE class) provided that the molecules are capable of forming a specific binding pair. In addition, joining molecules consisting of chimeric immunoglobulin heavy chains are within the scope of the present invention. Preferred joining molecules include full-length immunoglobulin heavy chain (Ig-$C_H$) or fragments thereof such as $C_H^1$; $C_H^1$–$C_H^2$; $C_H^1$–$C_H^3$ and $C_H^1$–$C_H^2$–$CH_H^3$. Additionally preferred fragments are capable of forming at least one disulfide bond with another suitable immunoglobulin chain or fragment. An especially preferred pair of joining molecules is a pair of immunoglobulin heavy chains having an IgG isotype.

In another embodiment, each of B1 and B2 is an immunoglobulin light chain the same or different provided that the light chains are capable of forming a specific binding pair as determined by RIA, Western immunoblot or other suitable binding assay. Suitable immunoglobulin light chain joining molecules may be full-length or fragments thereof and can be κ or λ type. As will be appreciated, a suitable fragment of a joining molecule will be one that is capable of forming a specific binding pair as determined by assays described herein.

Additionally, an immunoglobulin joining molecule in accord with the invention may be of animal (e.g., a rodent such as a mouse or rat), or human origin or may be chimeric or humanized (see e.g., Morrison et al., *PNAS* 81, 6851 (1984); Jones et al. *Nature* 321, 522 (1986)). Exemplary joining molecules include those capable of being specifically bound by anti-idiotype antibodies such as those disclosed below as well as commercially available anti-idiotype antibodies. See e.g., Linscott's Directory (40 Glen Drive, Mill Valley, Calif. 94941), and by the American Type Culture Collection (ATCC) 12301 Parklawn Drive, Rockville, Md. 20852.

Figure 7A:
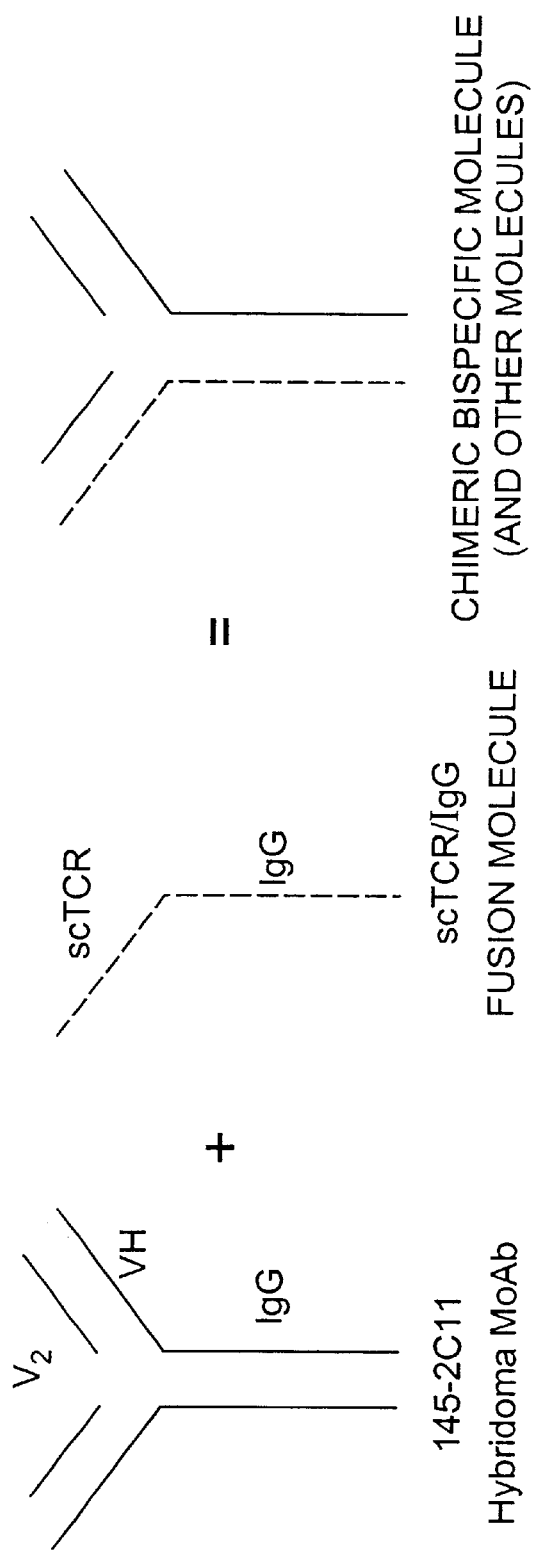
FIG. 7A is a schematic drawing showing a method for making a chimeric bispecific antibody molecule. The method uses a hybridoma-expressing cell (145-2C11 hybridoma) to produce antibody chains (heavy lines) that combine with an sc-TCR/Ig fusion molecule (light chain) inside the cell. A preferred structure for the sc-TCR/Ig molecule is illustrated in FIG. 7B.

More specific examples of multi-chain polyspecific binding proteins are represented in FIG. 7A. In the figure, the binding protein includes a sc-TCR linked to a first immunoglobulin heavy chain (Ig-$C_H$). The first Ig-$C_H$ is linked to a second Ig-$C_H$ to form a specific binding pair. The second Ig-$C_H$ is the same isotype (IgG) as the first immunoglobulin heavy chain and is further linked to an F(v) produced by a hybridoma cell. The sc-TCR is further linked to an immunoglobulin light chain produced the hybridoma cell. Additional multi-chain polyspecific binding complexes (sometimes referred to as "chimeric bispecific" molecules or antibodies) can be made by using other hybridoma cells or other sc-TCR/Ig molecules.

As mentioned previously, the present invention also features polyspecific binding proteins that include nonimmunoglobulin joining molecules. For example, each of B1 and B2 in the formula shown above can be a polypeptide that includes (or consists of) a protein-protein binding motif such as, e.g., a helix-turn-helix or leucine zipper motif. Many examples of these binding motifs have been described and are known in the field. See e.g., Horberg, et al., (1993) *Science* 262:1401; Kamtekar, et al., (1993) *Science* 262:1680; Harris, et al., *J. Mol. Biol.* (1996) 236:1356.

More specifically, each of B1 and B2 can be a polypeptide that consists of a protein-protein binding motif that is capable of forming a specific binding pair. For example, each of B1 and B2 can be a protein-protein binding motif of a transcription factor such as fos or jun. More specific examples of protein-protein binding motifs include birA (LXLIFEAQKIEWR; SEQ ID NO. 5), avidin (ARKCSLTGKWTNDLGSNMT; SEQ ID NO. 6), EE (EEEEYMPME; SEQ ID NO. 7), 6XHIS (GMAHHHHHH; SEQ ID NO. 8), fos/jun, and (TPPPEPET; SEQ ID NO. 9). See Rhind, S. K. (1992) U.S. Pat. No. 5,354,554; Altman, J. D. (1996) *Science*, 274:94; Shatz, P. (1993) *Biotechnology*, 11:1138. See also Examples 1–3 below.

As discussed, the present invention provides polynucleotides that encode single- and multi-chain polyspecific binding proteins (or portions thereof). In one embodiment, the polyspecific binding protein is encoded by a polynucleotide which can be RNA, DNA, or a chimera thereof. Typically, the polynucleotide will include or consist of a DNA sequence (segment) that encodes the binding protein.

For example, a polynucleotide according to the invention typically includes an operably linked leader sequence to provide appropriate cell processing signals. The leader sequence can be fused to the 5' end of the DNA sequence encoding the sc-TCR molecule. In particular, the leader can be covalently linked to the 5' end of the DNA sequence encoding the V-α chain, or in some embodiments, the V-β chain of the sc-TCR. In other embodiments, the leader will be fused to the sc-Ab and particularly to the sc-Fv. In a more specific embodiment, the leader sequence can be fused to the $V_H$ chain or the $V_L$ chain of the sc-Fv. It will be recognized however that although a specific leader sequence is linked to a particular sc-TCR or sc-Fv sequence, the leader sequence can often be exchanged using recombinant techniques without a detrimental effect on the processing of the fusion protein. Thus in one embodiment, the 5' end of the V-α chain is covalently linked to the 3' end of a suitable leader sequence.

A variety of specific leader sequences can be used with the polynucleotides. In one embodiment, the leader sequence is from between about 12 to 26 amino acid residues in length. In a specific embodiment, a DNA sequence designed for insertion into a bacterial expression vector can include a Pel B leader sequence. Alternatively, DNA segments for insertion into mammalian expression vectors may include an Ig-$C_L$ leader such as a mammalian $C_\kappa$ leader sequence. An exemplary $C_\kappa$ leader is provided below.

Additionally provided are polynucleotides that encode at least a portion of a polyspecific binding protein and particularly certain multi-chain polyspecific binding proteins represented in the formula shown above. In a more particular embodiment, the portion is sufficient to encode at least the A-B1 or D-B2 subunits. See Examples 8, 9 and 12 below.

Additional polynucleotides according to the invention include a DNA sequence that encodes a single-chain polyspecific binding protein of this invention. More specifically, the polynucleotide will usually include a promoter, translation initiation signal, and leader sequence operably linked to the sequence. For optimal expression in bacterial hosts, the promoter is preferably phoA and the leader is pelB from *E. coli*. If desired, the DNA sequence can further comprise a ribosome binding site from a gene 10 sequence. For optimal expression in eukaryotic hosts, the promoter is preferably a cytomeglovirus (CMV) promoter operably linked to a CMV enhancer element and the leader is a mouse kappa chain leader. By the term "operably linked" is meant a genetic sequence operationally (i.e., functionally) linked to a polynucleotide, or sequences upstream (5I or downstream (3' from a given segment or sequence.

Further polynucleotides according to the invention encode at least one sc-TCR or at least one sc-Fv each independently fused to a DNA sequence encoding a suitable bacteriophage coat protein. Preferably, the bacteriophage coat protein is a gene VIII or gene III protein. Methods for making and using the polynucleotides have been described in the pending U.S. application Ser. No. 08/813,781. See also U.S. Pat. No. 5,759,817 for disclosure relating to construction and use of bacteriophage fusion proteins.

More specific polynucleotides of this invention include a DNA sequence that encodes an sc-TCR that includes a V-α chain covalently linked by a suitable peptide linker sequence to the N-terminus of a V-β chain. Preferably, the DNA sequence further encodes an antibody binding domain and particularly an sc-Fv as discussed above separated from the sc-TCR by a suitable peptide linker sequence.

Polynucleotides that encode the present polyspecific binding proteins can be obtained from a variety of sources including polymerase chain reaction (PCR) amplification of publicly available DNA sequences. In one embodiment, the polynucleotide is provided in a DNA vector capable of expressing the molecule in a suitable eukaryotic or prokaryotic cell expression system. As discussed, polynucleotides of this invention may include operably linked transcriptional elements such as a promoter, leader and optimal enhancer sequences to drive expression of the soluble scTCR fusion protein in a desired cell expression system. Alternatively, the DNA vector may be selected to provide some or all of the control elements.

The term "vector" as used herein means a nucleic acid sequence capable of being incorporated and replicated into a host cell typically resulting in the expression of a nucleic acid segment of interest e.g., a polynucleotide encoding a polyspecific binding molecule as described herein. The vectors can include e.g., linear nucleic acid segments or sequences, plasmids, cosmids, yeast artificial chromosomes (YACs), phagmids and extra chromosomal DNA. Specifically, the vector can be recombinant DNA. Also used herein the term "expression," or "gene expression", is meant to refer to the production of the protein product of the nucleic acid sequence of interest including transcription of the DNA and translation of the RNA transcription. Typically, a DNA segment encoding an sc-TCR fusion protein of the invention is inserted into the vector, preferably a DNA vector, to replicate the DNA segment in a suitable host cell.

More particular DNA vectors according to the invention will include control elements that are selected to optimize expression in a host for which it is intended. For example, a DNA vector for use in a bacterial host can include a promoter such as the trp operon promoter, lac promoter, trp-lac promoter, lac$^{uva}$ or phoA promoter. Exemplary promoters are those such as phoA which provide strong, regulated expression during slow induction conditions lasting about several hours (e.g., 2 to 10 hours). Under suitable culture conditions, most strong promoters are capable of providing soluble fusion protein at levels up to and exceeding approximately 10% of the total host cell protein. See the pending U.S. application Ser. No. 08/813,781 for more disclosure relating to preferred conditions for expressing fusion proteins that include a sc-TCR in bacterial cells.

In some embodiments of the invention, a polynucleotide encoding a polyspecific binding protein of interest will be recombinantly engineered into an appropriate DNA vector. For example, in embodiments where the desired TCR or immunoglobulin chain is PCR-amplified, the oligonucleotide primers are usually configured with suitable restriction sites on both ends of the primers so that the polynucleotide can be replaced with another desired DNA. Thus, a suitable DNA vector of the invention is one in which the desired binding molecule can be readily inserted in the vector. Sometimes, as when an sc-TCR/IgG or other fusion between the sc-TCR or immunoglobulin heavy chain or fragment thereof is desired, the Ig-$C_L$ chain or chain fragment will be encoded by the vector and will be fused to the DNA segment by ligation. In other cases, the Ig-$C_L$ chain or the fragment will be fused to the DNA segment prior to the ligation to the vector.

In general, preparation of the present polyspecific binding proteins can be accomplished by specific procedures disclosed herein and by recognized recombinant DNA techniques. For example, preparation of plasmid DNA, DNA cleavage with restriction enzymes, ligation of DNA, introduction of DNA into a cell, culturing the cell, and isolation and purification of the expressed protein are known techniques. See generally Sambrook et al. in *Molecular Cloning: A Laboratory Manual* (2d ed. 1989); and Ausubel et al. (1989), *Current Protocols in Molecular Biology*, John Wiley & Sons, New York.

More particular strategies can be employed to express the polyspecific binding molecules described herein. For example, in one approach, a polynucleotide encoding a polyspecific binding protein of interest can be incorporated into a DNA vector by known means such as by use of enzymes to restrict the vector at pre-determined sites, followed by ligation of the DNA into the vector. The vector containing the DNA sequence is then introduced into a suitable host for soluble expression of the binding protein. Selection of suitable vectors can be empirically based on factors relating to the cloning protocol. For example, the vector should be compatible with, and have the proper replicon for the host cell that is being employed. Further, the vector must be able to accommodate the DNA sequence coding for the protein that is to be expressed. Preferred vectors are those capable of expressing the soluble proteins in mammalian cells e.g., pCDNA3 available from InVitrogen. See also Sambrook et al., supra and Ausubel et al. supra for other suitable vectors for use in, mammalian, cells. Typically, DNA vectors designed for expression in bacteria and encoding soluble fusion proteins will not include a full-length $C_\lambda$ or $C_\kappa$ intron although these sequences can be included in vectors designed for expression in mammalian cells capable of RNA splicing.

More preferred DNA vectors are designed to express the polyspecific binding protein in eukaryotic cells, particularly mammalian cells. The DNA vectors can be formatted for replication in a bacterial host if desired so that suitable amounts of the DNA vector can be obtained. For example, a DNA vector will usually include (i) an origin of replication (Ori) functional in *E. coli*; (ii) a selectable antibiotic resistance gene (e.g., Amp, Tet, Neo or Kan resistance); (iii) a strong viral promoter such as the cytomeglovirus (CMV) promoter and optional CMV enhancer element, (iv) an Ig-$C_L$ leader sequence, (v) a sc-TCR molecule of interest, (vi) a full-length Ig-$C_L$ intron linked to an Ig-$C_L$ exon, (vii) a growth hormone polyadenlyation sequence, e.g., bovine growth hormone (bgh) poly A sequence and (viii) DNA encoding a selectable eukaryotic marker such as a strong viral promoter (e.g., simian virus 40 (SV40) promoter) linked to the antibiotic resistance gene and fused to a viral polyadenlyation sequence (e.g., the SV40 polyA sequence). Alternatively, the DNA vector can include all of (i)–(v), and (Vii)–(viii), above, without the full-length Ig-$C_L$ intron linked to the Ig-$C_L$ exon of (vi). An exemplary Ig-$C_L$ leader sequence is the mouse kappa leader. An example of a full-length Ig-$C_L$ intron and exon is the full-length $C_\kappa$ gene.

Figure 5:
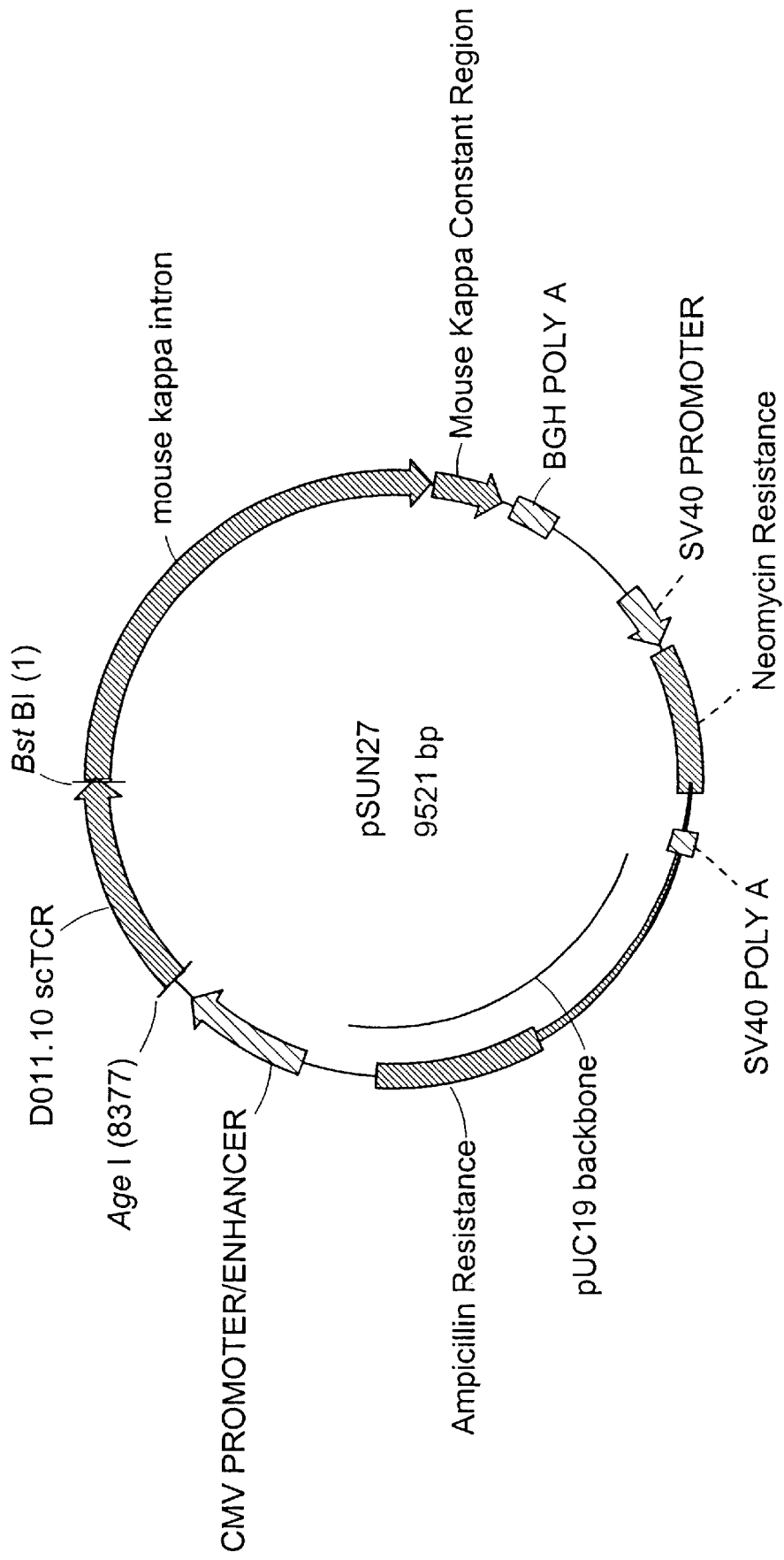
FIG. 5 is a schematic drawing showing the pSUN27 vector.

An example of a specifically preferred DNA vector for expressing the present single-chain polyspecific binding proteins in mammalian cells is the pSUN 27 vector illustrated in FIG. 5. Construction and use of the pSUN27 vector has been described previously in the pending U.S. application Ser. Nos. 08/813,781 and 08/943,086. The pSUN27 vector has been deposited pursuant to the Budapest Treaty with the American Type Culture Collection (ATCC) at 10801 University Boulevard, Manassas, Va. 20110-2209. The DNA vector was deposited with the ATCC on Sep. 17, 1997 and was assigned Accession No. 209276. The pSUN27 vector includes a CMV promoter, murine light chain leader sequence, Kozak consensus sequence, and the murine $C_\kappa$ gene intron and exon sequence. See also Near, et al., *Mol. Immunology* (1990) for more specific disclosure relating to the murine heavy chain sequence.

Additionally preferred are DNA vectors suited for joining a desired sc-TCR or functional fragment to an immunoglobulin heavy chain or fragment. For example, in one embodiment, the DNA vector can be replicated in a bacterial host if desired. In particular, the DNA vector will usually include (I) an origin of replication (Ori) functional in *E. Coli*; (ii) a selectable antibiotic resistance gene (Amp, Tet, Neo, or Kan); (iii) a strong viral promoter such as CMV promoter and optional CMV enhancer; (iv) a $V_H$ chain or fragment; (v) a $C_H$ chain; (vi) a growth hormone polyadenlyation sequence, e.g., bgh poly A sequence; and (vii) strong viral promoter (e.g., SV40 promoter) linked to the antibiotic resistance gene and fused to a viral polyadenylation sequence (e.g., SV40 PolyA sequence).

Figure 8:
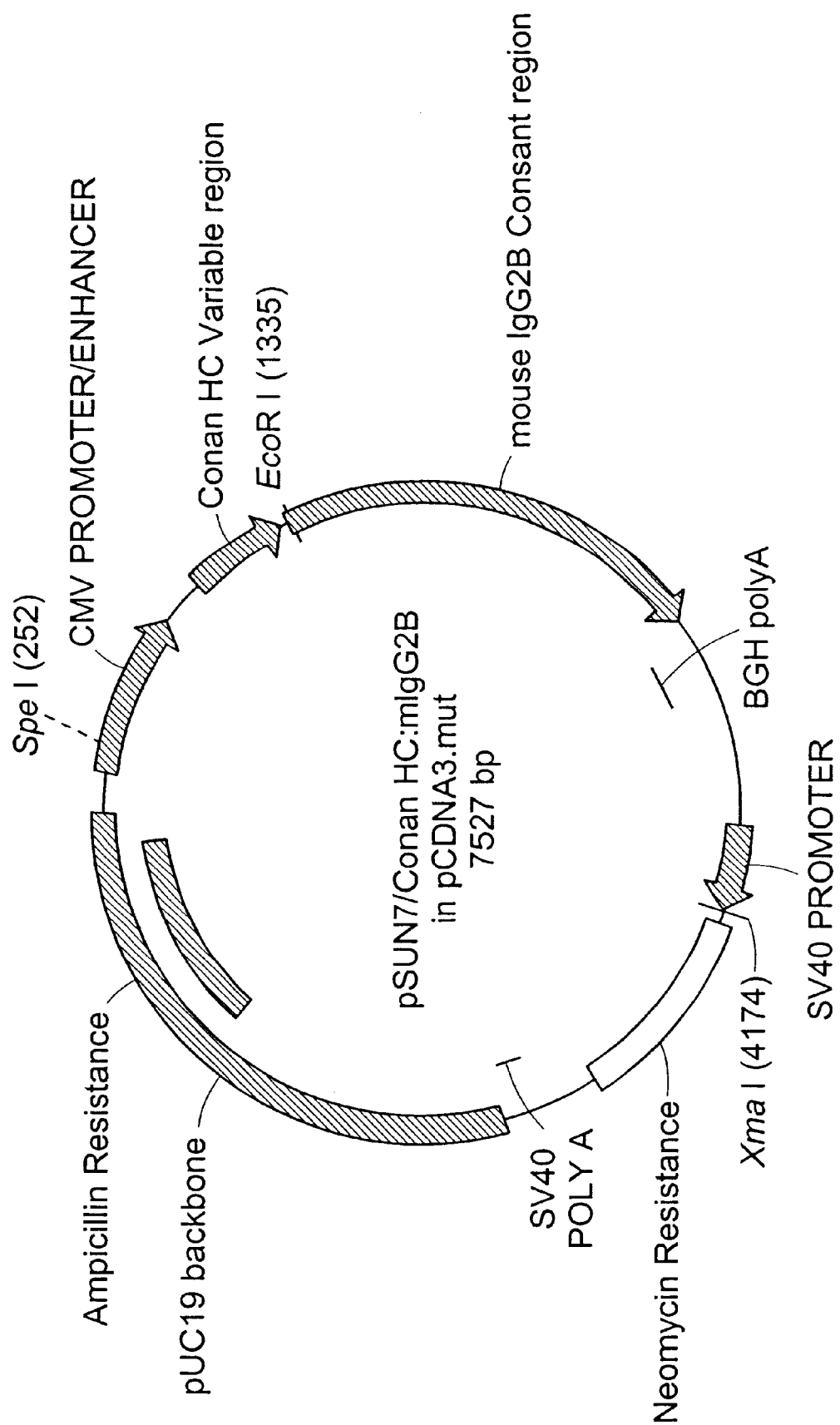
FIG. 8 is a drawing showing the vector pSUN7 vector.

An example of a specifically preferred DNA vector for joining a desired sc-TCR to the immunoglobulin chains is pSUN7 shown in FIG. 8.

A DNA vector of the invention can be modified according to conventional techniques to optimize expression in mammalian cells. For example, the eukaryotic marker encoding the neomycin resistance gene of the pSUN27 or pSUN7 vector described above can be replaced by DNA encoding the thymidine kinase (TK) gene to facilitate expression of the sc-TCR fusion protein in TK- (TK deficient) mammalian cells. The DNA vector can be modified in other ways well-known in the art (e.g., changing promoters, antibiotic resistance genes, replacing the CMV promoter with a promoter obtained from an immunoglobulin, SV40, an adenovirus or papilloma virus promoter to optimize sc-TCR fusion protein expression in a desired mammalian cell. Alternatively, the DNA sequence encoding the sc-TCR protein can be inserted into well-known vectors suitable for expression in yeast or insect cells, as desired. See e.g. Ausubel, et al., supra and Summer and Smith, infra.

A DNA vector especially designed for replication and expression of a desired binding protein in bacteria includes e.g., (i) an origin of replication functional in *E. coli* and derived e.g., from pBR322, preferably from well-known pUC19 vectors; (ii) a selectable antibiotic resistance gene, e.g., ampicillin and/or neomycin resistance gene; (iii) a transcriptional termination region, e.g., the termination region of the *E. coli* trp operon; (iv) a transcriptional promoter, e.g., a phoA, tac, tac-lac, lacZ, lac$^{uvs}$, T7, or T3 promoter; (v) a leader sequence, e.g., a pelB or ompA leader; (vi) a DNA sequence encoding the sc-TCR fused to a desired sc-Fv through a suitable peptide linker sequence (vii) a transcriptional terminator, e.g., the T1T2 sequence from the ribosomal RNA locus of *E. coli*. Alternatively, the vector can include (i)–(vii), above, except that the sc-TCR is provided with a fused Ig-$C_L$ chain or fragment.

Suitable host cells can be transformed by a variety of methods including retroviral transfer, viral or bacteriophage infection, calcium-, liposome-, or polybrene- mediated transfection, biolistic transfer, or other such techniques known in the art.

As noted previously, in some cases it may be desirable to express the polyspecific binding protein in non-mammalian cells. For example, suitable host cells for expressing the fusion proteins in bacteria include cells capable of being readily transformed and exhibiting rapid growth in culture medium. Particularly preferred hosts cells include *E. coli, Bacillus subtillus*, etc. Other host cells include, yeasts, e.g., *S. cerevisiae* and insect cells. Exemplary cells for insect cell expression are those capable of being infected by a baculovirus such as Sf9 cells. See also, Summer and Smith (1988) *A Manual of Methods for Baclovirus Vectors and Insect Cell Culture Procedures*, Texas Agricultural Experimental Station Bulletin No. 1555, College Station, Tex.

Although in the examples which follow cells of mammalian origin are used, in principle, nearly any eukaryotic cell is useful in the practice of the subject invention. Examples include primate cells, e.g., human cells such as fibroblast cells, and cells from other animals such as ovine, porcine, murine, and bovine cells. Specific examples of mammalian cells include COS, HeLa, and CHO, cells.

In general, cell culturing conditions are employed in which stably transformed or transfected cell lines are selected e.g., by incorporation of a suitable cell selection marker into the vector (e.g., an antibiotic resistance gene or G418). Cells which express a desired polyspecific binding protein of this invention can be determined by known procedures e.g., by ELISA assay using commercially available monoclonal antibodies which specifically bind the binding molecule at a desired site. Illustrative of such sites includes the V-α or V-β chain of the sc-TCR or the variable chain of an antibody binding site, e.g., the $V_H$ or $V_L$ chain of the sc-Fv. Alternatively, in embodiments in which a polyspecific binding molecule includes an immunoglobulin heavy chain, e.g., an sc-TCR/IgG molecule, a monoclonal antibody can be chosen which specifically binds the $C_\kappa$ or $C_\lambda$ chain (or fragment). Examples of monoclonal antibodies and suitable assays are provided in the examples below.

If included, a leader sequence in a DNA vector suitably directs expression of the binding protein to host cell membranes or to the host cell media and can be formatted to include a restriction site so that DNA encoding, e.g., a V-α chain of interest, can be conveniently ligated to the construct. Suitably, the restriction site is incorporated into the 3'-end of the leader sequence, sometimes referred herein as a junction sequence, e.g. of about 2 to 10 codons in length, and linked to the V-α chain so that the coding region for the V-α chain is typically the first amino acid of the V-α coding region. Alternatively, the leader sequence can be linked to the $V_H$ or the $V_L$ coding region of the sc-Fv chain. For example, one restriction site is the Sfi I site, although other cleavage sites can be incorporated before the V-α chain coding region to augment convenient insertion of the V-α chain into the vector construct. As discussed above, use of such a restriction site in combination with a second restriction site, typically positioned at the beginning of the V-α chain, enables rapid and straightforward insertion of sequences coding for a wide variety of V-α chains, or V-α, C-α chains. Preferred leader sequences contain a strong translation initiation site and can sometimes include a cap site at the 3'-end of their mRNA. As mentioned above, exemplary leader sequences include pelB, and OmpA for bacterial expression and a $C_\kappa$ mouse kappa chain leader sequence for mammalian expression.

The present invention also includes methods for isolating the polynucleotides or vectors encoding same. In general, the methods include introducing the vector or polynucleotide into desired host cells, culturing the cells and purifying the encoded polyspecific binding molecule (or portion thereof) from the host cells to obtain substantially pure protein. The vector or polynucleotide can also be isolated in substantially pure form by standard methods. Typically, the vector or polynucleotide will be DNA for most recombinant manipulations.

In some instances, the polyspecific binding proteins of the present invention will include one or more fused protein tags (typically one or two). For example, the protein tags can be used to help purify the protein from naturally occurring cell components, which typically accompany the fusion protein. In other cases, the protein tag can be used to introduce a pre-determined chemical or proteolytic cleavage site into the soluble fusion protein. Particularly, contemplated is introduction of a segment encoding a protein tag into a DNA vector, e.g., between sequence encoding the soluble fusion protein and the Ig-$C_L$ chain or suitable fragment so that the scTCR molecule can be cleaved (i.e. separated) from the Ig-$C_L$ chain or fragment if desired.

Polyspecific binding molecules that include a protein tag can have that tag fused to the molecule by genetic or chemical manipulations as needed. In one embodiment, the binding molecule includes one protein tag fused to the C-terminus of the protein. Alternatively, the protein tag can be fused to the N-terminus of the binding protein. In another embodiment, the protein tag is fused between the sc-TCR and sc-Ab molecules of the polyspecific binding protein.

The polyspecific binding proteins of this invention can be purified by several conventional techniques. For example, as previously mentioned, the binding proteins can include at least one protein tag (the same or different), including tags which comprise a chemical or protease cleavage site. Particularly, a protein tag can be a polypeptide bearing a charge at physiological pH, such as e.g., 6×HIS. In this embodiment, a suitable synthetic matrix can be used to purify the fusion protein. More particularly, the synthetic matrix can be a commercially available sepharose matrix, such as e.g. Ni-Sepharose or other such suitable matrixes capable of binding the 6×HIS tag at about pH 6–9. Other suitable tags include EE or MYC epitopes, which are specifically bound by commercially available monoclonal antibodies. In general, a wide variety of epitopes capable of being specifically bound by an antibody, e.g., a monoclonal antibody, are capable of serving as a protein tag. Other suitable synthetic matrices includes those with a bound antibody capable of specifically binding the present sc-TCR proteins. Exemplary protein tags include those with an enterokinase, Factor Xa, snake venom or thrombin cleavage site. See e.g., published PCT application WO 96/13593. See also Example 6–7 below.

An expressed polyspecific binding protein can be isolated and purified by known methods including immunoaffinity chromatography, immunoabsorption, immunoprecipitation and the like. Importantly, the preparative procedures will not usually require prolonged isolation steps to obtain significant yields of the fusion protein. In accordance with the protein purification methods described more fully below, yields for most polyspecific binding proteins are in the range of about 2 to 6 milligrams per liter.

As discussed, the polyspecific binding proteins of this invention can be expressed and purified by one or a combination of strategies. In one approach, a polyspecific binding protein such as a single-chain fusion protein is expressed in a suitable cell. Preferably the binding protein is expressed in the cell or cell media. A cell extract or host cell culture medium is obtained and then centrifuged. The resulting supernatant can be purified by affinity or immunoaffinity chromatography, e.g. Protein-A or Protein-G affinity chromatography or an immunoaffinity protocol comprising use of an antibody that specifically binds the binding protein. Examples of such an antibody are commercially available monoclonal antibodies capable of specifically binding the sc-TCR, sc-Fv or other portion of the binding molecule such as the protein tag or immunoglobulin heavy chain portion. More specific examples of suitable monoclonal antibodies are those capable of binding a V-α chain or V-β chain of the sc-TCR, e.g., H57, B20.1, MR5-2, and F23.1 (Pharmagen). Specific examples of such antibodies are anti-idiotypic antibodies such as those in the examples below.

As described above, the polyspecific binding molecules of the present invention are provided in a soluble and fully functional form. Thus, in one embodiment, the binding molecules are stably secreted into culture medium and are capable of specifically binding a ligand of interest such as a TCR antigen or portion thereof capable of binding the binding molecule. In embodiments of the invention in which a polyspecific binding molecules is present as a single-chain, the molecule is preferably stable under physiological conditions in the substantial or complete absence of a chaotropic agent such as a detergent or the like. Thus, the binding molecules will usually not include regions rich in hydrophobic amino acids such as those amino acids found in a TCR transmembrane region.

The polyspecific binding molecules provided herein can be modified by standard methods to include a variety of covalently linked protein tags (effectors). For example, one or more effectors or tags can be added to the binding molecules to visualize bridging between bound cells and/or to boost recognition, damage or killing by immune cells. Potential sites for adding the effectors or tags include the sc-TCR, sc-Fv or immunoglobulin heavy chain portion (if present). Preferred tags generally impart a desired biological, chemical or physical property. More specific effectors or tags have been described in the pending U.S. application Ser. Nos. 08/813,781 and 08/943,086.

Additional examples of suitable protein tags include polypeptide sequences that have a charge at physiological pH, such as, e.g., 6×HIS. In this instance, a suitable synthetic matrix to purify the polyspecific binding complex would be, e.g., a commercially available metallo-sepharose such as, e.g., Ni-sepharose or other such suitable matrix capable of binding 6×HIS at about pH 6–9. The EE epitope and myc epitope are further examples of suitable protein tags, which epitopes can be specifically bound by one or more commercially available monoclonal antibodies. Effector molecules may be conjugated to the polyspecific binding complexes by means of a heterobifunctional protein cross-linking agent such as, e.g., SPDP, carbodimide, or the like. See Meany and Feeney, supra; Wong, supra.

It will be useful for some applications to non-recombinantly modify the polyspecific binding complexes of the invention by non-genetic means. For example, the binding complexes can include a variety of pharmaceutical agents in addition to those described above such as drugs, enzymes, hormones, chelating agents capable of binding, e.g., a radionuclide, as well as other proteins and polypeptides useful for diagnosis or treatment of disease. For diagnostic purposes, the polyspecific binding molecule can either be labeled or unlabelled. For example, a wide variety of labels may be suitably employed, such as radionuclides, fluors, enzymes, enzyme substrates, enzyme cofactors, enzyme inhibitors, ligands such as, e.g., haptens, and the like.

For some applications, it will be desirable to position a polyspecific binding molecule by including a fused peptide linker sequence. Several suitable peptide linkers and methods of testing same have been described. In some cases it may be useful to add an agent to the fused peptide linker in accordance with well-known techniques. Examples of useful agents include photometrically detectable labels such as, e.g., a dye or a fluor; an enzyme (such as, e.g., β-galactosidase, alkaline phosphatase, or horseradish peroxidase; which enzymes are capable of forming a photometrically detectable label). See generally U.S. Pat. No. 5,434,051 for a discussion of suitable photometrically detectable labels. Alternatively, the agents can be conjugated directly to the polyspecific binding molecules disclosed herein by a variety of other means not involving a peptide linker, some of which means are disclosed.

Further, the polyspecific binding proteins of the invention can be post-translationally modified if desired by e.g., carbohydrate or fatty acid addition. For example, the binding molecules can be modified by glycosylation. Glycosylation sites on proteins are known in the art and are typically either N-linked (asparagine-linked) or O-linked (serine- or threonine-linked). Such glycosylation sites can be readily identified by inspection of the protein sequence. The present binding molecules can be glycosylated by suitable eukaryotic cells as evidenced by, e.g., SDS-PAGE gel electrophoresis. SDS-PAGE gel electrophoresis and other related methods can be combined with conventional biochemical techniques such as, e.g., enzymatic digestion, to detect carbohydrate bound to the polyspecific binding proteins of the invention. Examples of preferred digestive enzymes include, e.g., endoglycosidases, and exoglycosidases available, e.g., from New England Biolabs (Beverly, Mass.). Accordingly, the polyspecific binding molecules of the invention can be readily analyzed for the presence of carbohydrate groups, particularly oligosaccharide groups.

In some instances, it may be useful to obtain substantially pure polyspecific binding molecules of the invention in glycosylated form. Particularly, such glycosylated molecules may exhibit less in vivo degradation when administered as a therapeutic agent, thereby increasing circulating half-life (see e.g., Goto, M. et al. *Bio/Technology* 6:67 (1988)).

In particular, the present polyspecific binding molecules are also suitable for a variety of in vitro and in vivo uses including diagnostic and imaging applications as well as HLA typing. See e.g., A. K. Abbas, *Cellular and Molecular Immunology*, page 328 (W. B. Saunders Co. 1991). For in vivo imaging applications, a polyspecific binding protein of interest can be detectably labeled by addition of $^{125}I$, $^{32}P$, $^{99}Tc$ or other detectable tag. The labeled polyspecific binding molecule can then be administered to a mammal and the subject scanned by known procedures. Such an analysis of the mammal could aid in the diagnosis and treatment of a number of disorders including e.g. undesired expression of APCs accompanying immune system disorders.

Molecular weights of present polyspecific binding molecules will vary depending on a number of factors including whether a particular binding molecule includes one or more sc-TCR molecules, what specific antibody binding domain is included, whether a full-length $C_\kappa$ or $C_\lambda$ chain is present, or whether one or more protein tags is employed. In general, in embodiments in which the polyspecific binding molecule is present as a single-chain, the binding molecule will have a molecular weight from between about 80 to 110 kDA, and particularly from between about 90 to 100 kDA. In this embodiment, the V-α and V-β chains of the sc-TCR will have a molecular weight of greater than about 16 kDA, more typically between about 12 to about 20 kDa. Additionally, in embodiments in which he sc-Fv includes a $V_H$ and a $V_L$ chain, the chains will have a molecular weight of greater than about 18, more typically about 12 to about 20 kDA. The molecular weight of a specific binding molecule will depend on several paramters including the number of sc-TCR or sc-Fv molecules present.

As discussed, some polyspecific binding molecules of the present invention are multi-chain molecules and especially bispecific chimeric antibodies. See FIGS. 7A and 7B. Typically, the multi-chain molecules will have a molecular weight from between about 150 to about 250 kDa or greater depending, e.g., on the number of sc-TCR or sc-Fv molecules present. All of the above mentioned molecular weights are determined by conventional molecular sizing experiments such as SDS-PAGE gel electrophoresis or centrifugation. See generally Sambrook, et al., supra Harlow and Lane, supra; Ausubel et al, supra.

In some settings it can be useful to increase the valency of a particular polyspecific binding molecules. For example, one way to increase the valency of a polyspecific binding molecule is to covalently link together between one and four binding molecules (the same or different) by using e.g., standard biotin-streptavidin labeling techniques, or by conjugation to suitable solid supports such as latex beads. Chemically cross-linked proteins (for example cross-linked to dendrimers) are also suitable polyvalent species. For example, the protein can be modified by including sequences encoding amino acid residues with chemically reactive side chains such as Cys or His. Such amino acids with chemically reactive side chains may be positioned in a variety of positions in the fusion protein, preferably distal to the binding region of the sc-TCR or sc-Fv.

As a specific example, the C-terminus of the polyspecific binding molecule can be covalently linked to a protein purification tag or other fused protein which includes such a reactive amino acid(s). Suitable side chains can be included to chemically link two or more fusion proteins to a suitable dendrimer particle to give a multivalent molecule. Dendrimers are synthetic chemical polymers that can have any one of a number of different functional groups on their surface (D. Tomalia, *Aldrichimica Acta*, 26:91:101 (1993)). Exemplary dendrimers for use in accordance with the present invention include e.g. E9 starburst polyamine dendrimer and E9 comburst polyamine dendrimer, which can link cysteine residues.

Highly useful in vitro and in vivo T-cell binding assays have been disclosed in published PCT application Ser. Nos. PCT/US95/09816, PCT/US96/04314 and PCT/US97/01617, as well as the pending U.S. patent application Ser. Nos. 08/382,454, 08/596,387 and 08/943,086. The disclosed T-cell binding assays can be used or readily adapted if necessary to test the function of the polyspecific binding proteins of this invention. The disclosures of said published PCT application Ser. Nos. PCT/US95/09816, PCT/US96/04314, PCT/US97/01617, and pending U.S. application Ser. Nos. 08/382,454, 08/596,387 are each incorporated herein by reference.

The ability of a polyspecific binding protein of the present invention to modulate activity of an immune cells and especially a T-cell (i.e. cause or elicit T-cell activity such as proliferation) can be readily determined in accordance with the assays and materials for performing the assays disclosed in said published PCT application Ser. Nos. PCT/US95/09816, PCT/US96/04314, PCT/US97/01617, as well as said pending U.S. patent application Ser. Nos. 08/382,454, 08/596,387 and 08/943,086. See also Matsui, et al. (1994) *PNAS (USA)* (1994) 91:12862.

More specifically, as disclosed in said published PCT application Ser. Nos. US95/09816, PCT/US96/04314, PCT/US97/01617, as well as said pending U.S. patent application Ser. Nos. 08/382,454, 08/596,387 and 08/943,086, in vitro assays can be performed to determine if a molecule is capable of modulating T-cell activity. Such assays can be modified to determine functionality of the polyspecific binding proteins. Generally, a exemplary assay is conducted as follows, by the sequential steps 1–4 below.

T-cells suitably express a marker that can be assayed and that indicates T-cell activation, or modulation of T-cell activity after activation. Thus, as disclosed in the prior applications, the murine T-cell hybridoma DO11.10 expressing interleukin-2 (IL2) upon activation can be employed. IL-2 concentrations can be measured to determine if a particular sc-TCR fusion molecule is capable of modulating activity of the T-cell hybridoma (e.g., increasing IL-2 production). A general example of such a suitable assay is conducted by the following sequential steps:

1. Suitable T-cell hybridomas or T-cells are obtained.
2. The T-cell hybridoma or T-cells are then cultured under conditions that allow proliferation.
3. The proliferating T-cell hybridoma or T-cells are then contacted with one or more of the polyspecific binding proteins. The cells will typically not proliferate (i.e. they are resting) until the polyspecific binding protein is added along with suitable target cells.
4. In cases where non-hybridoma T-cells are employed such as naive T-cells, it may be useful to add a suitable co-stimulatory factor to provide signals necessary for activation. The T-cell hybridomas or T-cells are subsequently assayed for a marker, e.g. IL-2 production is measured. In embodiments in which a bispecific molecule is used, production of IL-2 is one way to evaluate the extent to which the bispecific molecule can modify the T-cell response. Preferred are bispecific molecules that provide for cell bridging and facilitate about a two to about a threefold increase in IL-2 over a suitable control (i.e. an unstimulated T-cell). Additionally preferred are bispecific molecules which when used without added immune cells will not result in stimulation and in significant IL-2 production as measured by the above-mentioned general assay. That is, addition of the polyspecific binding molecule without addition of target cells will not result in significant T-cell stimulation (i.e. IL-2 production). See Example 14 below for a more specific assay.

As disclosed previously in said published PCT application Ser. Nos. PCT/US95/09816, PCT/US96/04314, PCT/US97/01617, and in said pending U.S. patent application Ser. No. 08/382,454, 08/596,387 and 08/943,086, the T-cells employed in the assays are usually incubated under conditions suitable for proliferation. For example, a DO11.10 T-cell hybridoma is suitably incubated at about 37° C. and 5% $CO_2$ in complete culture medium (RPMI 1640 supplemented with 10% FBS, penicillin/streptomycin, L-glutamine and 5×10–5 M 2-mercaptoethanol). Serial dilutions of a fusion protein can be added to the T-cell culture medium in concentrations typically in the range of from $10^{-8}$ to $10^{-5}$ M. T-cell activation signals are preferably provided by antigen presenting cells that have been loaded with the appropriate antigen.

As disclosed previously in said published PCT Application Nos. PCT/US95/09816, PCT/US96/04314, PCT/US97/01617 and in said pending U.S. patent application Ser. No. 08/382,454, 08/596,387 and 08/943,086, rather than measurement of an expressed protein such as IL-2, modulation of T-cell activation can be suitably determined by changes in antigen-dependent T-cell proliferation as measured by radio-labelling techniques as are recognized in the art. For example, a detectably-labeled (e.g., tritiated) nucleotide may be introduced into an assay culture medium. Incorporation of such a tagged nucleotide into DNA serves as a measure of T-cell proliferation. This assay is not suitable for T-cells that do not require antigen presentation for growth, e.g., T-cell hybridomas. It is suitable for measurement of modulation of T-cell activation for untransformed T-cells isolated from mammals. T-cell proliferation following contact with the fusion protein (only in the presence of peptide/MHC target cells) indicates that the molecule modulates activity of the T-cells and can suppress immune response. The in vitro T-cell proliferation assay is preferred for measuring the effects of fusion proteins on antigen-specific changes in T-cell colony expansion in vivo. Measurement of IL-2 production or T-cell proliferation can be employed to determine if the polyspecific binding protein is capable of modifying T-cell activation.

Additionally preferred bispecific binding molecules include those capable of mediating CTL killing of desired target cells as determined by a cytotoxicity assay such as a conventional chromium ($Cr^{51}$) release assay. In a specific embodiment, the chromium release assay is used to measure CTL killing. The cell killing can be monitored and quantified if desired by a number of suitable means including measuring the released chromium. The chromium release assay is readily adaptable for use with nearly any polyspecific binding molecules disclosed herein and suitable tumor cell targets. Preferred are bispecific binding molecules that are capable of releasing between at least about 10 to 15% lysis with respect to spontaneous release from suitable control cells. See Example 18 below for more specific information regarding the chromium release assay.

In general, suitable T-cells for the assays are provided by transformed T-cell lines such as T-cell hybridomas or T-cells isolated from a mammal, e.g., a primate such as from a human or from a rodent such as a mouse, rat or rabbit. Other suitable T-cells include: 1) T-cell hybridomas which are publicly available or can be prepared by known methods, 2) T helper cells, and 3) T cytotoxic cells, preferably cytotoxic CD8+ cells. T-cells can be isolated from a mammal by known methods. See, for example, R. Shimonkevitz et al., *J. Exp. Med.*, (1983) 158:303.

Related in vitro and in vivo assays for testing sc-TCR molecules have been described in said published PCT application Ser. Nos. PCT/US95/09816, PCT/US96/04314, PCT/US97/01617 and in said pending U.S. patent application Ser. No. 08/382,454, 08/596,387 and 08/943,086. Such assays can be readily adapted for use with the present polyspecific binding molecules as needed.

See Example 14 below for an especially preferred assay for detecting stimulation of T hybridoma cells using preferred bispecific hybrid molecules.

The present invention provides additional methods for testing the single- and multi-chain polyspecific binding proteins disclosed herein. For example, the functionality of the sc-TCR or antibody-binding portion of the binding molecules can be readily demonstrated by a variety of specific binding assays. Preferred binding assays monitor and preferably quantitate specific binding between the antibody binding portion and a desired cell surface protein. Preferred specific binding assays include Western blotting, ELISA, RIA, mobility shift assay, enzyme-immuno assay, competitive assays, saturation assays, cytometric assays or other protein binding assays know in the art. Preferred are assays that are capable of detecting a cell surface protein, e.g., a TCR, glycoprotein or other suitable molecule.

One preferred assay for analyzing the present polyspecific binding molecules is an ELISA assay. For example, in one embodiment, suitable host cells expressing a desired bispecific hybrid molecule are screened in an ELISA format using an antibody that is capable of specifically binding the hybrid molecule. Preferred are bispecific hybrid molecules that include a protein tag such as an EE-tagged molecule. In this instance, the tagged molecules can be probed using commercially available antibodies that specifically bind the tag. The bound antibody can be conveniently detected using standard ELISA, e.g., by binding a second detectably-labeled antibody that binds the antibody recognizing the EE-tag. Alternatively, the bispecific hybrid molecule may be probed with an antibody that specifically binds the sc-TCR or the antibody binding domain and particularly the sc-Fv.

The above-described ELISA assays can be used to detect and characterize nearly any of the polyspecific binding proteins disclosed herein. Additionally, the ELISA assays can be used to screen cells for capacity to express a desired polyspecific binding protein. See Example 3 and FIGS. 9A, 9B, 10A, 10B and 11 for results of illustrative ELISA assays.

Figure 12:
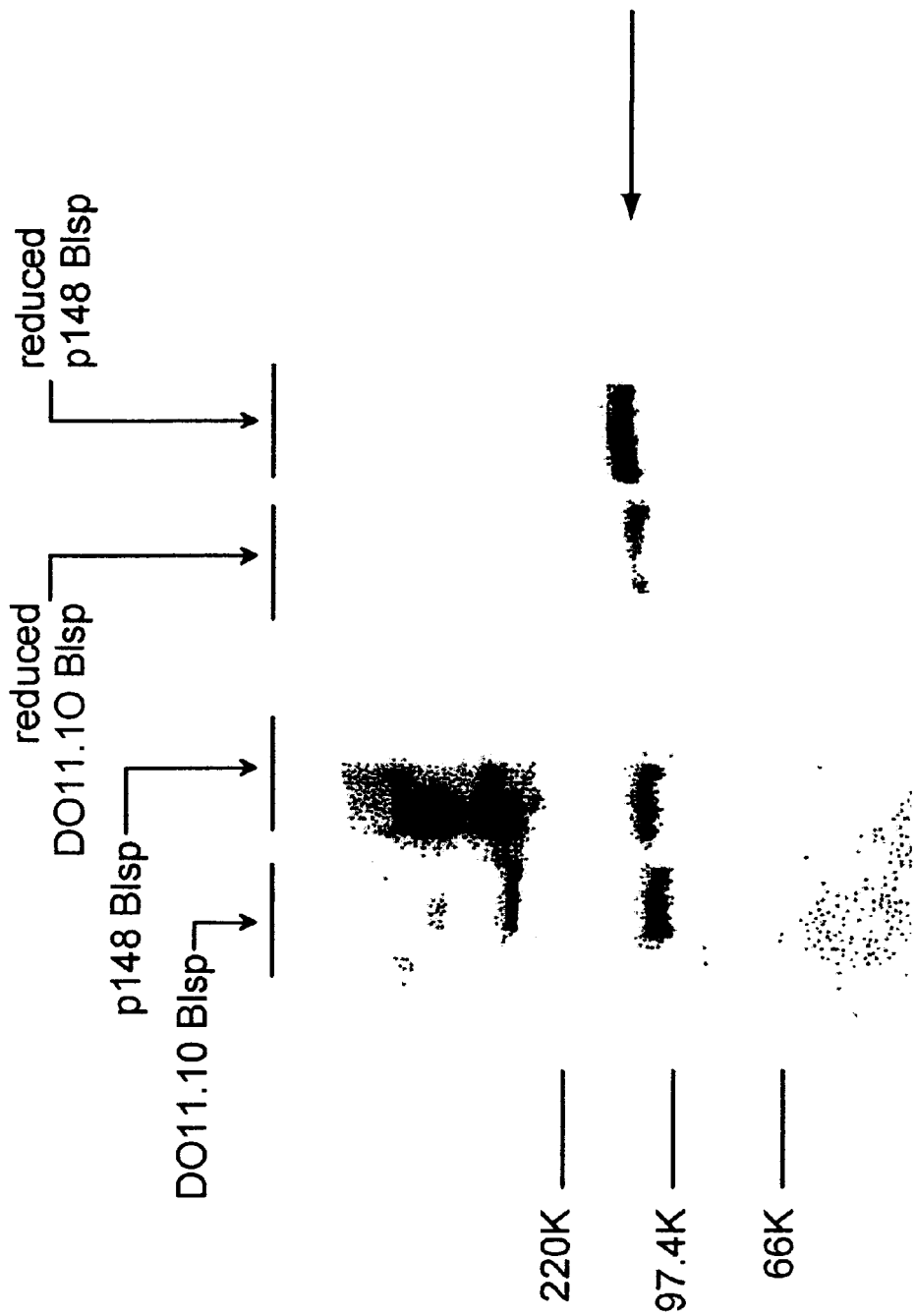
FIG. 12 is a representation of a Western Blot showing expression of BISP/DO11.10 and BISP/p149 bispecific hybrid molecules. Also shown are reduced forms of the proteins (arrow).

Additionally preferred assays for analyzing the present polyspecific binding proteins include Western immunoblots. Briefly, a particular polyspecific binding protein such as a bispecific hybrid molecule can be separated by conventional gel electrophoresis and transferred to a suitable support medium. The transferred blot can then be probed with a wide variety of antibodies such as those that specifically bind the sc-TCR or antibody binding domain, e.g., the sc-Fv. Bound antibody can be visualized by standard detection methods. See the Examples below and FIG. 12.

Additionally preferred assays for analyzing the present polyspecific binding proteins involve flow cytometric analysis. For example, specific binding between the sc-TCR or sc-Fv portion of a bispecific hybrid protein and a glycoprotein or other suitable marker expressed on a cell can be determined by flow cytometric analysis. In a more particular example, T hybridoma cells or other suitable cells that express the CD3 molecule are contacted with the bispecific hybrid molecule under conditions conducive to forming a specific binding complex. The cells are then washed and contacted with a detectably-labeled antibody (e.g., biotinylated) specific for a V chain of the sc-TCR or a protein tag attached to the bispecific hybrid molecule (e.g., the EE tag). A standard chromogenic assay is then performed using labeled streptavidin and spectrophotometric detection methods. Functionality of the sc-Fv can be demonstrated by staining of the T-hybridoma cells. Non-specific staining can be detected by a variety of methods including use of T hybridoma cells that do not express the CD3 molecule. For some applications it may be useful to check the binding specificity by including a suitable antibody that can compete with the bispecific hybrid protein for binding to the cells. Preferred bispecific binding proteins will exhibit from an increase in cytochrome from between about 5 to 1000 fold and preferably between from about 10 to 100 fold when compared to a suitable control. See Example 15 and FIGS. 17–19 for results of a flow cytometric analysis.

As discussed, the present invention also features recombinant bacteriophages that include fusion proteins that comprise sc-TCR or sc-Fv molecules fused to a suitable bacteriophage protein or fragment thereof. As discussed, sc-Fv fusion proteins comprising a bacteriophage coat protein are known in the field. Methods for making and using sc-TCR fusion proteins comprising a bacteriophage coat protein have been disclosed in pending U.S. application Ser. No. 08/813,781. See also U.S. Pat. No. 5,759,817. It will be apparent from the examples that follow that the disclosed methods can be adapted, as needed, to facilitate manufacture of the present recombinant bacteriophages.

More particularly, the present recombinant bacteriophages display fusion proteins that each include a sc-TCR or sc-Fv linked to a bacteriophage coat protein or fragment. Preferred recombinant bacteriophages of this invention are bispecific and feature the binding specificity of the sc-TCR and sc-Fv fusion proteins. As disclosed in the pending U.S. application Ser. No. 08/943,086, the scTCR fusion protein generally includes a bacteriophage coat protein or fragment thereof covalently linked to a V-α chain fused to a V-β chain preferably through a flexible peptide linker sequence. Preferably, the bacteriophage coat protein is a bacteriophage gene III or gene VIII protein. The sc-Fv fusion protein typically includes a bacteriophage coat protein or fragment covalently linked to the $V_H$ or $V_L$ chain preferably through a flexible peptide linker protein. As used herein "bacteriophage coat protein" includes the full-length coat protein. A suitable fragment of that coat protein is capable of facilitating packaging of the scTCR or sc-Fv and displaying the scTCR or sc-Fv as a fusion protein component of the bacteriophage coat. Successful packaging can be demonstrated in several ways including plaque assays that quantitate production of infectious particles. More specific disclosure relating to methods of making and using the bacteriophages can be found in Examples 21, 24, 26–28 below.

In one embodiment, the recombinant bacteriophages of this invention display scTCR and sc-Fv fusion proteins that each optionally include one or more fused protein tags (typically one or two). Attachment of at least one protein tag has several advantages including providing a straightforward way of purifying the bacteriophages from cell components which can accompany it. Preferred are proteins tags that facilitate chemical or immunological recognition of the bacteriophage such as those specific tags described below. An especially preferred tag is the EE sequence.

In particular, the sc-TCR and sc-Fv fusion proteins of the recombinant bacteriophages of this invention can include nearly any sc-TCR or sc-Fv molecule described herein. For example, the sc-TCR fusion protein can include covalently linked in sequence: 1) a V-α chain, 2) a suitable peptide linker sequence, 3) a V-β chain 4) a Cβ-chain and 5) and a first bacteriophage coat protein or fragment. The sc-Fv fusion protein can include covalently linked in sequence: 1) a $V_H$ chain, 2) a suitable peptide linker sequence, 3) a $V_L$ chain, and 4) a second bacteriophage coat protein or fragment. The first and second bacteriophage coat proteins can be the same or different depending, e.g., on the amount or quality of display desired.

In embodiments in which the recombinant bacteriophage includes fusion proteins that each comprise a sc-TCR or sc-Fv fusion protein, that bacteriophage will sometimes be referred to herein as a "bispecific bacteriophage" or simply "bispecific phage". Illustrative of such bispecific phages include those that display a desired sc-TCR fused to the bacteriophage gene VIII protein and the sc-Fv fused to the gene III protein. However, in some cases, it may be useful to make recombinant bispecific bacteriophages that display the sc-TCR fused to the gene III protein and the sc-Fv fused to the gene VIII protein.

As discussed, additional disclosure relating to the construction and use of the sc-TCR fusion proteins can be found in the pending U.S. application Ser. No. 08/813,781. In particular, the pending U.S. application Ser. No. 08/813,781 discloses an sc-TCR fusion protein that includes a C-β chain fragment covalently linked between the C-terminus of the Vβ chain and the N-terminus of the bacteriophage gene III protein. Optionally, a protein tag can be covalently linked to the C-terminus of the C-β fragment and the N-terminus of the bacteriophage gene III protein. Also disclosed is an sc-TCR fusion protein that includes a first protein tag covalently linked between the C-terminus of the V-β chain and the N-terminus of the bacteriophage gene III protein, and a second protein tag covalently linked to the C-terminus of the fusion protein.

Additionally disclosed in the pending U.S. application Ser. No. 08/813,781 is an sc-TCR fusion protein that includes covalently linked in sequence: 1) a V-α chain, 2) a peptide linker sequence, 3) a V-β chain covalently linked to a C-β chain fragment, and 4) a bacteriophage gene VIII protein. Also taught is an sc-TCR fusion protein that includes covalently linked in sequence: 1) a V-α chain covalently linked to a C-α chain fragment, 2) a peptide linker sequence, 3) a V-β chain covalently linked to a C-β chain fragment, and 4) a bacteriophage gene VIII protein. In this embodiment, the sc-TCR may further include a first protein tag covalently linked to the C-terminus of the V-β chain and the N-terminus of the gene VIII protein, and a second protein tag covalently linked to the C-terminus of the fusion protein. Additionally, a protein tag may be covalently linked to the C-terminus of the C-β chain fragment and the N-terminus of the gene VIII protein.

If desired, the present recombinant bacteriophages can be manipulated to have valancies from between about 2 to 10 and preferably from between about 2 to 3. That is, the bacteriophages can be formatted to include: 1) between from about 2 to 3 sc-TCR fusion proteins, 2) between from about 2 to 3 sc-Fv fusion proteins, or 3) between from about 2 to 3 sc-TCR and sc-Fv fusion proteins. Such polyspecific bacteriophages are highly useful, e.g., as when it is desirable to increase the avidity or binding affinity of an sc-TCR or sc-Fv fusion protein displayed on the bacteriophage.

The present invention also provides methods for making the recombinant polyspecific bacteriophages described herein. For example, in one embodiment, bacterial host cells are transfected with polynucleotides that encode a sc-TCR or sc-Fv in which the encoded sc-TCR or sc-Fv is fused to a suitable bacteriophage coat protein or fragment. Also contemplated are polynucleotides that encode a functional fragment of the sc-TCR or sc-Fv. Also envisioned are polynucleotides that encode multiple copies (i.e. about 2 to 5) of the sc-TCR or sc-Fv. More specific disclosure relating to making and using polynucleotides encoding the sc-TCR fused to a suitable bacteriophage coat protein or fragment can be found in the pending U.S. application Ser. No. 08/813,781.

The present recombinant bacteriophages can be produced by one or a combination of strategies. Preferred are methods that use bacterial host cells such as *E. coli* that are conducive to the bacteriophage propagation. In a particular embodiment, the host cells are transfected with a polynucleotide that encodes the sc-TCR fusion protein under. conditions sufficient to display same as part of the bacteriophage coat or capsid. The host cell can be infected at the same time or at later time with a polynucleotide encoding the sc-Fv fusion protein under conditions that are also conducive to displaying the sc-FV fusion protein on the capsid. Production of the polyspecific bacteriophages can be detected and quantified if desired by a variety of conventional methods methods such as RIA, ELISA, Western immunoblot and affinity chromatography.

In another embodiment, the recombinant polyspecific bacteriophages of this invention are made by infecting suitable host cells with "monospecific" recombinant bacteriophages that independently carry the sc-TCR or sc-Fv fusion proteins described herein. More specific disclosure relating to such bacteriophages can be found in the pending U.S. application Ser. No. 08/813,781. See also U.S. Pat. No. 5,759,817. For example, in a more specific embodiment, the polyspecific bacteriophages can be made by first infecting suitable bacterial host cells with a monospecific bacteriophage and then infecting the same host cells with the other monospecific bacteriophage. Alternatively, the infection can be conducted by co-infecting with both monospecific bacteriophages.

It will be appreciated that the present methods for making the recombinant polyspecific bacteriophages are highly flexible. That is, the order in which the host cells are transfected (or infected) with a particular polynucleotide (or recombinant bacteriophage) is not important so long as the resulting recombinant bacteriophage has the binding specifies intended. The recombinant bacteriophages of this invention provide a number of important uses and advantages. For example, the bacteriophages preferably display full- or nearly full-length scTCR and sc-Fv molecules. Accordingly, use of the present bacteriophage libraries positively impacts analysis of scTCR and sc-Fv molecules, particularly scTCR and sc-Fv binding pockets.

The present recombinant bacteriophages are particularly useful for a wide spectrum of screens such as those formatted to detect and evaluate specific binding of a sc-TCR and sc-Fv molecules. The bacteriophages are also useful for analyzing a variety of binding molecules such as antigens, antibodies, small molecules, superantigens and MHC/HLA peptide complexes. Importantly, the present bacteriophage display libraries express fusion proteins with a V-$\alpha$ and a V-$\beta$ chain, thereby making the fusion proteins more fully representative of TCRs found in vivo.

Additionally, the present bacteriophages can be manipulated to maximize formation of specific binding complexes between the bacteriophages and desired binding molecules or even cells, thereby increasing detection of the binding molecules or cells which may be rare or weakly binding. The bacteriophages of the invention are especially amenable to biopanning techniques (e.g., cell panning and immunopanning).

As discussed, the recombinant bacteriophages and bacteriophage libraries of the present invention can be provided in kit form. The kit may include recombinant bacteriophages displaying a single type of sc-TCR and sc-Fv. Alternatively, the kit may include a recombinant bacteriophage library in which case the library will preferably include a variety of different sc-TCR and sc-Fv fusion proteins. More specific kits further include pertinent host cells and/or reagents for detecting the bacteriophages, e.g., antibodies and directions for using the kit.

The present invention also provides a variety of methods for administering at least one polyspecific binding protein to a mammal and preferably a rodent or a primate such as a human patient. For example, in one embodiment, there is provided a method for administering a polynucleotide that encodes a polyspecific binding molecule and especially a single-chain polyspecific-binding molecule. Preferred are polynucleotides that can express the single-chain binding molecule in the mammal. Preferably, DNA carrying the coding regions of the binding protein, suitably under the control of an strong eukaryotic promoter such as a strong viral promoter (e.g., CMV), is injected directly into skeletal muscle of the subject according to known methods. Methods for administration of plasmid DNA, uptake of that DNA by cells of the administered subject and expression of protein has been reported (see J. Ulmer et al. *Science*, (1993) 259:1745–1749). In embodiments in which the polyspecific binding molecule is administered to a mammal and especially a human, it is preferred that the isotype of the molecule be compatible with the host employed.

As noted previously, the polyspecific binding proteins of the present invention have therapeutic applications. For example, as discussed, the binding molecules can be used to redirect the specificity of a certain immune cells and particularly a T-cell, CTL, CD8+ cell, NK cell, or macrophage to eliminate a desired target cell that expresses an MHC such as a virally infected or tumor cell. Cross-linking of the immune cells with the target cells provides a potent immune response sufficient to damage or kill the target cell.

Additionally, the polyspecific binding proteins described herein can be administered to reduce or eliminate an immune response in a mammal, e.g., to treat a mammal such as a human that suffers from or is susceptible to cancer and an infectious disease. Also suitable for treatment are those subjects suffering or likely to suffer from an undesired immune response e.g. patients undergoing transplant surgery such as transplant of heart, kidney, skin or other organs. In situations involving transplant rejection, a treatment protocol may suitably be commenced in advance of the surgical procedure.

Administration of the polyspecific binding molecules described herein can be via any suitable means such as administration of a therapeutically effective amount of the fusion protein or polynucleotide encoding same. In some embodiments in which DNA administration is desired it may be helpful to provide two or more polynucleotides encoding parts of a desired polyspecific binding protein such as when use of a bispecific hybrid molecule is desired.

A number of specific approaches can be employed to reduce or kill desired target cells in accord with the present invention. For example, one treatment method for damaging and preferably killing target cells provides for the administration of a therapeutically effective amount of a desired polyspecific binding molecule to link target cells expressing an MHC complex to specific immune cells expressing a cell surface antigen. Association between the target cells and the immune cells facilitates an immune reaction that damages and preferably eliminates the target cells. In some embodiments, more than one polyspecific-binding molecule may be administered as needed. In some instances, T-cell mediated immune responses such as T-cell proliferation, differentiation, activation or B lymphocyte stimulation can be selectively controlled.

The polyspecific binding proteins described herein can be administered to a mammal by injection, e.g., intraperitoneal or intravenous injection. In preferred embodiments, the polyspecific binding proteins are preferably produced from mammalian or other suitable cells and purified prior to use so it is essentially or completely free of pyrogens. The optimal dose for a given therapeutic application can be determined by conventional means and will generally vary depending on a number of factors including the route of administration, the patient's weight, general health, sex, and other such factors recognized by the art-skilled.

Administration can be in a single dose, or a series of doses separated by intervals of days or weeks. The term "single dose" as used herein can be a solitary dose, and can also be a sustained release dose. The subject can be a mammal (e.g.,. a human or livestock such as cattle and pets such as dogs and cats) and include treatment as a pharmaceutical composition which comprises at least one polyspecific binding protein and typically one of such protein. Such pharmaceutical compositions of the invention are prepared and used in accordance with procedures known in the art. For example, formulations containing a therapeutically effective amount of the binding protein may be presented in unit-dose or multi-dose containers, e.g., sealed ampules and vials, and may be stored in a freeze dried (lyophilized) condition requiring only the addition of the sterile liquid carrier, e.g. water injections, immediately prior use. Liposome formulations also may be preferred for many applications. Other compositions for parenteral administration also will be suitable and include aqueous and non-aqueous sterile injection solutions which may contain anti-oxidants, buffers, bacteriostat and solutes which render the formulation isotonic with the blood of the intended recipient; and aqueous and non-aqueous sterile suspensions which may include suspending agents and thickening agents.

Methods of the invention which include reducing or eliminating target cells expressing e.g., a tumor or viral peptide loaded MHC. The methods may be used in combination with other therapies such as anti-viral, immunosuppressive, anti-cancer or anti-inflammatory therapies to provide a more effective treatment regimen. For example, the polyspecific binding proteins of this invention can be used with specific anti-viral agents such as those used to reduce or eliminate a retrovirus infection and particularly infection by the AIDS virus. Additionally, the polyspecific binding proteins can be used with standard anti-cancer therapies such as chemotherapy or immunotherapy.

As mentioned previously, in some instances it may be useful to produce antibodies to the polyspecific binding proteins described herein or fragments thereof. More specific methods for making antibodies have been described in the pending U.S. application Ser. Nos. 08/813,781 and 08/943,086.

As mentioned above, the polyspecific binding molecules described herein can be readily modified by one or a combination of strategies to improve binding. More specific disclosure relating to methods for improving the binding of sc-TCR molecules has been reported in the pending U.S. application Ser. No. 08/813,781.

Substantially pure soluble fusion proteins or nucleic acids are at least about 90 to 95% pure and preferably at least 98% to 99% or more pure for pharmaceutical use. Once purified partially or to substantial purity, the soluble fusion proteins can be used therapeutically (including extracorporeally), or in developing or performing in vitro or in vivo assays as disclosed herein.

All documents mentioned herein are fully incorporated herein by reference in their entirety. The following non-limiting examples are illustrative of the invention.

EXAMPLE 1

Construction of p-149 Single-chain (sc) TCR

The T cell clone, p-149, recognizes a peptide fragment (STPPPGTRV, SEQ ID NO. 10) of the human wild-type tumor suppresser protein p53 restricted by HLA-A2.1. (See Theobald et al., *PNAS*, 1995) The T cell receptor gene was cloned into a three domain single-chain format previously shown to produce soluble TCR and functional receptor molecules (FIG. 1A).

In brief, mRNA was isolated from the T cell clone and cDNA was made using the Marathon cDNA Amplification Kit (Clontech). The cDNA was used as a template in polymerase chain reaction (PCR) with primers KC171 and KC174 to produce a 5'SfiI3'SpeI Vα chain fragment including the first seven amino acids of the Cα chain N-terminus. The same cDNA was then used as a PCR template with primers KC172 and KC 176 to generate a 5'XhoI-3'XmaI V beta C beta chain fragment. The C beta chain was truncated just before the cysteine residue at amino acid 127 of the full-length C beta chain.

Figure 3:
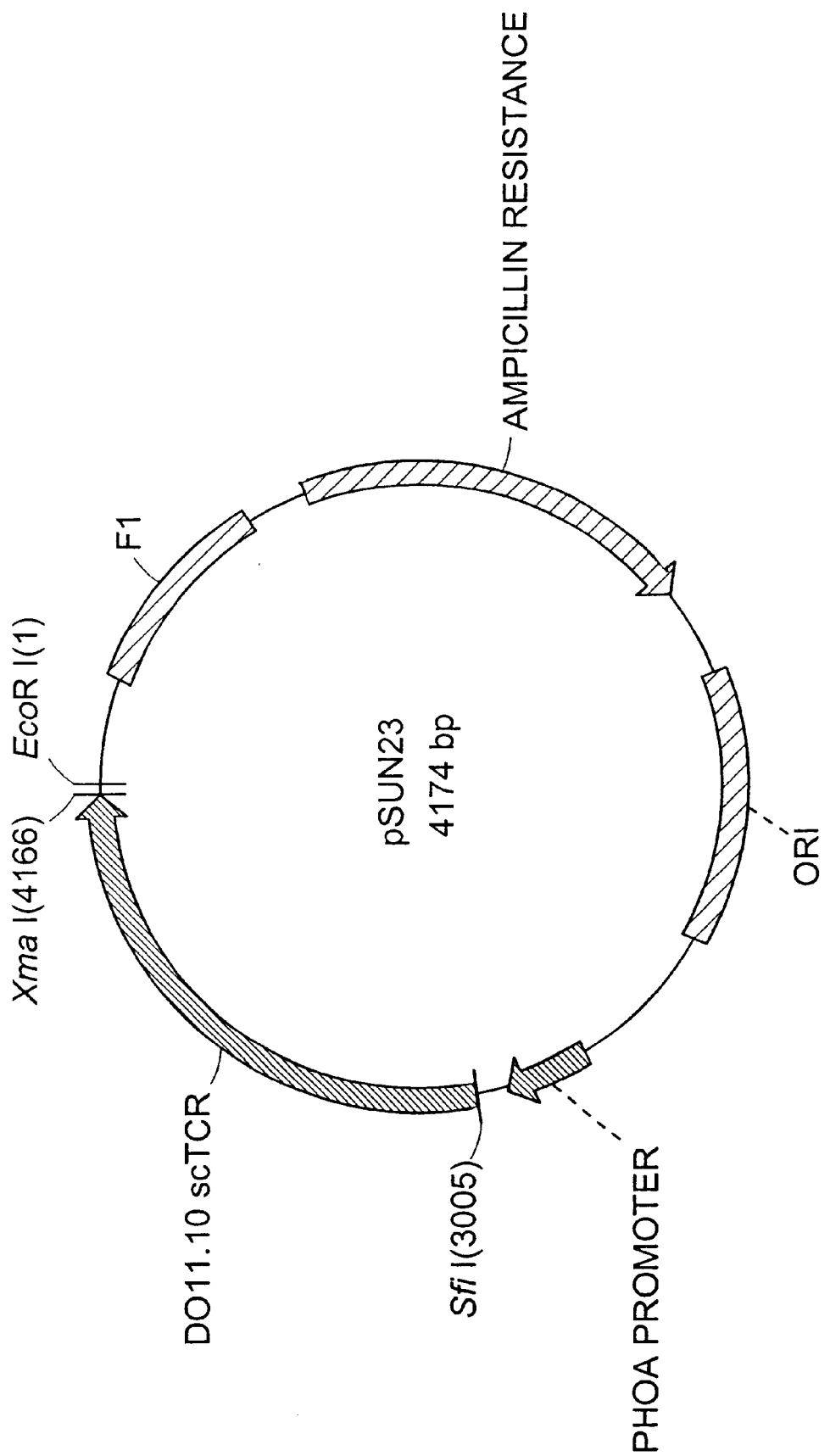
FIG. 3 is a schematic illustration of the pSUN23 vector.
Figure 4:
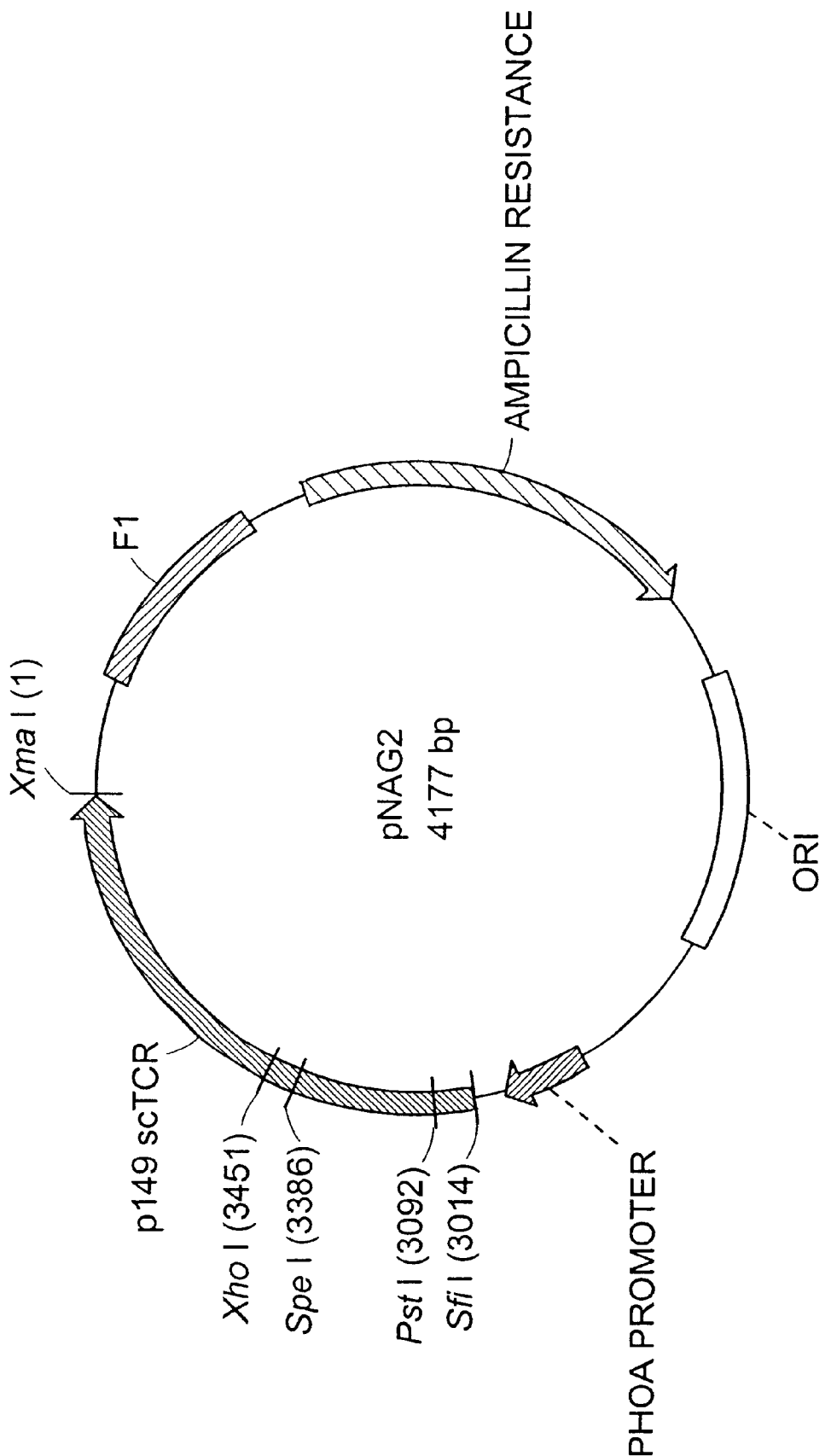
FIG. 4 is a schematic illustration of the pNAG2 vector.

The alpha and beta chain fragments were cloned into the pGEM-T Easy Vector System (Promega) for DNA sequence determination. Correct fragments were restriction digested and cloned into the expression vector pKC60 to create a V alpha-$(G_4S)_4$ V beta C beta scTCR molecule. The pK60 vector is referred to herein as PSUN23 (FIG. 3). The pKC60 vector has been described in the pending U.S. application Ser. No. 08/813,781. The new vector was named pNAG2 (FIG. 4).

The *E. coli* DNA construct pNAG2 was then reamplified by PCR with primers KC203 and KC208 to generate a 5'AgeI-3'HpaI/BspEI/NruI/ClaI DNA fragment. The scTCR fragment was cloned into the pGEM-T Easy Vector System for DNA sequence determination.

This new pGEM-based vector was then used as a "shuttle vector" for introduction of other DNA fragments to create a bispecific sc molecule.
1. Cloning and Expression of Variant p-149 sc-TCR Forms in *E. coli.*

It is possible to provide the p-149 sc-TCR in a variety of useful constructs. For example, four variations of the pSUN21 construct described below can be used to express the scTCR. It has been found that the level of soluble scTCR is increased when the scTCR is expressed in the pSUN21 scTCR design shown in FIG. 1B. Therefore, an initial cloning will be accomplished by using this single-chain construct as a template. As described, a two-step cloning procedure will be used to assemble the scTCR into the expression vector. As discussed above, the p-149 cDNA encoding the full length alpha and beta chains of this receptor has been cloned. Related cloning methods can be used to make the variants.

For example, one variant of the p-149 TCR construct will closely resemble the DO11.10 scTCR cloned into vector pSUN21. This construct contains the Vα domain, a stretch of 10–25 amino acids followed by a (G4S)4 linker, and the Vβ/Cβ domains. An EE-tag sequence will be included at the carboxyl terminal region. This facilitates detection of the molecule on immunoblots and can be used for cross-linking scTCR molecules. A slightly modified second construct will encode a BirA site (see Example 24 below) at the carboxyl terminal end. BirA has been characterized as a biotinylation sequence and has been used to produce tetrameric forms of MHC molecules. See Altman et al., *Science*, 274, 94–96 (1996). The site will be used for constructing tetrameric scTCR molecules for evaluation of the scTCR in cell binding and blocking assays. Also envisioned is construction of monomeric forms by cross-linking the scTCR with the scFv containing the BirA and avidin (see Example 24 below) tags, respectively. The addition of the BirA site through genetic manipulation has an advantage over more traditional biotinylation methods that rely on chemical cross-linking protocols. In many instances, the us of such coupling agents results in the denaturation of the protein which could be avoided by encoding at the gene level a site for biotinylation. Another advantage of having the BirA site is that stoichiometrically, a one:one molar ratio of scTCR:scFV can be assembled.

In another example, a p-149 scTCR variant can be made that will contain the DNA encoding for the jun sequence. This will be cloned as a 3' DNA fragment into the scTCR design. The scTCR/jun fusion will be available for cross-linking with the scFv/fos fusion.

In yet another example of a p-149 variant, a fusion protein can be made whereby, the carboxyl terminal region of the Cβ/EE-tag is genetically fused to pVIII, the major coat protein filmentous phage. A variety of sc-TCR fusions comprising bacteriophage proteins including the pVIII and pIII proteins have been disclosed in the pending U.S. application Ser. No. 08/813,781. As we described, the construction of bispecific phage (expression of both scTCR and scFV fragments on the surface of the phage) will be the one form of this hybrid molecule. The molecule has a variety of important uses including killing tumor cells in vitro and in vivo, by forming a "bridge" between CTL and target cells. The pSUN21 vector will be used to clone the scTCR/pVIII fusion. The vector has a lacZ promoter and has been used in the development of the scTCR/phage display model discussed in the preliminary results section. This is a modified pBluScript vector that can produce phage expressing scTCR/pVIII molecules after superinfection with wild-type phage.

As disclosed in the pending U.S. application Ser. No. 08/813,781 and 08/943,086, a variety of specific DNA vectors can be used to fuse a desires sc-TCR to bacteriophage coat proteins. For example, the pending U.S. Application disclose the DNA vectors pKC46 (pSUN18) and pKC62 (pSUN19). These vectors have been deposited pursuant to the Budapest Treaty with the American Type Culture Collection (ATCC). The DNA vectors were deposited with the ATCC on Feb. 26, 1997 and were assigned Acession Nos. 97895 (pSUN18) and 97896 (pSUN19). The DNA vector pKC62 (pSUN19) includes a phoA promoter, modified pelB sequence, gene 10 ribosome binding site and bacteriophage gene VIII protein. The DNA vector pKC46 (pSUN18) includes the lac Z promoter, an EE tag and bacteriophage gene III protein. The DNA vectors can be propagated in *E. coli* or other suitable host cells in accordance with standard methods.

The DNA vectors pKC46 (pSUN18) and pKC62 (pSUN19) are designed to accommodate a variety of Vα, Vβ-Cβ and polypeptide linker sequences. The Vα chain of both DNA vectors can be removed by restriction digestion with SFiI and SpeI. The Vβ-Cβ chain can be removed by restriction digestion with XhoI-XmaI. Additionally, the DNA vectors allow exchange of the peptide linker sequence by restriction digestion with SpeI and XhoI. See FIGS. 2A–2E for more specific examples of sc-TCR constructs.

EXAMPLE 2

Purification and Characterization of the p-149 sc-TCR

The pending U.S. application Ser. No. 08943,086 discloses a variety of methods for purifying sc-TCR proteins including these that comprise the DO11.10 sc-TCR. These methods can be adapted to purify the p-149 fusion protein. For example, to purify the scTCR, an antibody with specificity for a conformational epitope on Vβ 11.0 or Vα 2.3 can be used along lines disclosed in the pending U.S. application. In particular, the p-149 scTCR can be purified on an immunoaffinity column using the following procedure.

Cell paste generated from a fermentor can be suspended in extraction buffer followed by mechanical lysing of cells by passage through a French press. The supernatant is clarified by centrifugation at 25,000×g and applied to a Q-sepharose column. The scTCR is collected in the flow-thru and then applied to a Protein-A-sepharose column cross-linked with mAb H57-95. This is a hamster mAb specific for an epitope on the C-beta domain of murine TCRs. This antibody shows good binding characteristics for murine TCRs and has been previously used to purify intact scTCR molecule as well as breakdown products from the lysate. To remove the degraded or improperly folded receptors, a second antibody affinity column will be used that can discriminate between scTCR that is conformationally intact from scTCR that has been degraded. Bound scTCR is eluted using a 50 mM glycine buffer, pH 11, and the scTCR preparation will be analyzed by running sampled on a 12% SDS polyacrylamide gel and staining with coomassie brilliant blue or western blotting.

To determine whether the expressed protein is functional, the scTCR can be tested in accord with assays disclosed in the pending U.S. application Ser. Nos. 08/813,781 and 08/943,086 such as a cell binding assay and a blocking assay. The cell binding assay can be performed as discussed in the pending U.S. applications. Alternatively, the assays can be modified by forming tetramers using scTCR molecules that include a single biotin sequence at the carboxyl terminal end. See Example 24 below. The tetramers will be formed by adding streptavidin coupled to PE and then incubating these molecules with tumor cells known to naturally process and present the 149 peptide associated with HLA-A2.1. Controls will include cells only expressing HLA-A2.1, antigen and cells expressing neither the HLA-A2.1, nor the peptide. It is anticipated that a peak shift in fluorescence of cells expressing the peptide associated with HLA-A2.1.

EXAMPLE 3

Construction, Expression and Characterization of the DO11.10 scTCR

The DO11.10 TCR recognizes OVA peptide (323–339) in context of the class II MHC IA$^d$ molecule. (See Haskins et al., J. Exp. Med., 1983.) The *E. coli* DNA construct pKC60 was reamplified by PCR with primers KC169 and KC208 to generate a 5'AgeI-3'HpaI/BspEI/NruI/ClaI DNA fragment. The scTCR DNA fragment was cloned into the pGEM-T Easy Vector System for DNA sequence determination. The correct scTCR DNA was then restriction digested with AgeI and HpaI and cloned into the "shuttle vector", replacing the previous scTCR DNA fragment, to generate a new scTCR/scSc-Fv bispecific sc molecule. The DO11.10 bispecific sc molecule was then cloned into pSUN27 to create pBISP/DO11.10 (FIG. 6).

The pBISP/149scTCR vector (pSUN 28) has been deposited pursuant to the Budapest treaty with the ATCC on Sep. 3, 1998 and was assigned Acession No. 203186.

1. Expression of Variant scTCR Molecules in *E. coli*.

The effect of changes in the design of the scTCR was investigated on the level of protein expression. Vectors which encode for the different scTCR and fusion constructs were used to transform E. coli K91 cells. Expression experiments were carried out by growing transformed K91 cells overnight in media containing inorganic phosphate to prevent activating the phoA promoter and inducing protein expression. The following morning a new culture was started from the overnight culture and grown until phosphate had been depleted. The duration of induction was normalized by monitoring the depletion of phosphate over time in the culture. See the pending U.S. application Ser. Nos. 08/813,781 and 08/943,086 for additional disclosure relating to producing sc-TCR fusion molecules.

To compare the level of expression between the different constructs, protein was prepared from samples for analysis from cell lysates that had been normalized to the same absorbence reading at 600 nm (10 OD/ml). Protein was released from cells by sonication and the sample was clarified by centrifugation at 25,000×g for 20 minutes. Samples were then loaded onto a 12% SDS-PAGE gel and after electrophoresis and transfer of proteins to a nylon membrane, the TCR was detected by probing with an antibody specific for the EE-tag. We observed in this expression experiment that alterations to the basic design of the scTCR can produce significant changes in the level of soluble protein expressed. For example, the scTCR construct pSUN22, which includes the Vα and Vβ domains joined by a synthetic linker, is not detectable in the soluble fraction at the concentration of material loaded. A signal can be detected by loading 50-fold more sample although the signal is still not equivalent to the levels seen with pSUN21. These data indicate high levels of soluble scTCR can be produced in E. coli by modifying the construct design.

2. Characterization of the Soluble sc-TCR

A. Immunoprecipitation

The folding integrity of the scTCR protein produced by pSUN23 and pSUN19 DNA vectors was analyzed by running binding assay experiments using two mAb (MR5-2 and F23.1) with specificity for correctly folded epitopes on Vβ8.2. Furthermore, scTCR having correctly paired Vα with Vβ chains were assayed using an anti-idiotype mAb, KJ1, generated against the DO11.10 TCR. The binding assay experiments have been described in the pending U.S. application Ser. Nos. 08/813,781 and 08/943,086. The data indicate that the scTCR protein has a conformationally correct Vβ domain and correctly paired Vα and Vβ domains.

B. Enzyme-Linked Immunoassay (ELISA)

A sandwich ELISA assay was used to further characterize the folding domains of the scTCR. Use of the ELISA assay is more fully described in the pending U.S. application Ser. Nos. 08/813,781 and 08/943,086. Briefly, different dilutions of the scTCR was captured by anti-EE tag mAb coated on wells and was detected using one of the following mAbs, H57 (Cβ), MR5-2 (Vβ8.2), F23.1 (Vβ8.2) and KJ1 (Vα/Vβ). These data support the presence of a correctly folded scTCR and indicated that the scTCR is stable even after elution at high pH (11.0) and storage at 40° C. for several weeks.

C. Surface Plasmon Resonance (BioCore) Binding Studies Using Antibodies and Superantigen.

The scTCR/geneVIII fusion protein was characterized using surface plasmon resonance. The technique is more fully described in the pending U.S. application Ser. No. 08/813,781. As disclosed in the pending U.S. application Ser. No. 08/813,781, the data indicate that although the two anti-TCR mAbs recognize different epitopes they showed stearic hindrance which prevented binding of both mAbs to the beta chain in this assay format. To demonstrate the presence of the bacteriophage pVIII protein on the scTCR fusion protein, the scTCR was bound by the anti-M13 antibody. Binding of the Streptococcus SAg known as SEC3 (Toxin Technology, Tampa Fla.) to the scTCR/ gene VIII fusion is also disclosed in the pending U.S. application Ser. No. 08/813,781. These data together with the antibody binding data demonstrate that the E. coli produced scTCR is correctly folded.

3. Purification of the DO11.10 scTCR

Methods for purifying sc-TCR fusion proteins have been disclosed in the pending U.S. application Ser. Nos. 08/813, 781 and 08/943,086. The DO11.10 sc-TCR can be purified by those methods including the following specific method.

The fusion protein encoded by vector pSUN23 was purified from transformed cells by immunoaffinity chromatography in accordance with conventional methods. Briefly, the purification was performed by making an affinity column by coupling 4 mg of anti-idiotype antibody, KJ1 per ml of protein-A coated sepharose beads (Pharmacia). E. coli lysates were prepared by solubilizing 50 g of fermentor-derived cell paste in 600 ml of solubilization buffer. Resuspended cells were lysed by two passages through a French press. Insoluble material was removed by centrifugation at 27,000 g for 30 minutes and the supernatant was applied to a Q-sepharose anion exchange column. The scTCR protein was collected in the flowthru and subsequently applied to the antibody column. Bound scTCR was eluted with a 50 mM glycine buffer, pH 11.0 and fractions containing protein were used for characterization.

The scTCR protein preparations were evaluated for purity by electropheresis on an SDS-PAGE gel followed by commassie brilliant blue staining. Protein integrity was determined by immunoblotting using either antibody H57–597 or anti-Glu-Glu (EE) tag antibody as a probe. Finally an aliquot of purified scTCR was run under reduced and non-reduced conditions and after transfer of proteins the membrane was probed with the anti-EE tag antibody. The western blot results indicated that the purified scTCR was present as a monomer since both reduced and non-reduced samples migrated with the 46kD molecular weight marker.

EXAMPLE 4

Construction of 145-2C11 sc-Fv

The anti-murine CD3-epsilon monoclonal antibody hybridoma cell line 145-2C11 was purchased from American Type Culture Collection. (See Leo et al., PNAS, 1987) The DNA sequence of the variable chain coding regions of the antibody are available via the world wide web.

The Sc-Fv was designed as a $V_L$ -linker-$V_H$ gene construct. (See Jost et al, J. Biol. Chem., 1994) First, a shorter $(G_4S)_3$ linker was designed and made by annealing complementary oligos KC245 and KC246 to form a 5'SpeI-3'XhoI DNA fragment. pKC60 was restriction digested with the appropriate restriction enzymes to drop out the previous linker DNA fragment and allow for ligation with the annealed oligos.

To prepare DNA encoding the V regions of the mAb, mRNA from $10^6$145-2C 11 hybridoma cells was isolated using the RNeasy Total RNA Kit (Qiagen) in accordance with the manufacturer's instructions. $V_H$ chain cDNA was made by incubating a mixture containing "back" primer KC244 along with the 145-2C 11 mRNA. Standard amounts of nucleotides and reverse transcriptase were added to the mixture to form cDNA. The VH chain cDNA was made in a similar manner with the exception that "back" primer KC253 was used instead of the KC244 primer. $V_L$ chain cDNA was used as a template with primers KC243 and KC244 in a PCR reaction to amplify a 320 bp 5'SfiI-3"SpeI $V_L$ chain fragment. $V_H$ chain cDNA was used as a template with primers KC247 and KC253 in a similar manner to amplify a 350 bp 5'XhoI-3"XmaI $V_H$ chain fragment.

The $V_L$ and $V_H$ chain fragments were cloned into the pGEM-T Easy Vector System for DNA sequence determination. Correct fragments were restriction digested and cloned into the pKC60 expression vector already containing the shorter linker sequence described above.

Once the 145-2C11 Sc-Fv was complete, the DNA construct was reamplified by PCR with primers KC250 and KC251 to generate a 5'BspEI-3'NruI DNA fragment. The fragment was cloned into the pGEM-T Easy Vector System for DNA sequence determination. The correct DNA was then restriction digested and cloned into the "shuttle vector" downstream of the scTCR. See FIGS. 1C–1D for illustrations of the 145-2C11 sc-Fv (IC) and F23.1 sc-Fv (ID) molecules.

EXAMPLE 5

Design of the sc Molecule Linker Sequence

To connect the scTCR and scSc-Fv together as a single-chain fusion protein, two different linker sequences were designed. One set of annealed oligos, KC209 and KC210, coded for part of the CH1 domain of murine heavy chain followed by the standard (G4S) sequence. A second, shorter linker sequence was designed similarly but without the CHI domain using annealed oligos KC295 and KC296. Oligos were annealed to generate a 5'HpaI-3'BspEI DNA fragment. The "shuttle vector" was digested with the appropriate restriction enzymes to drop out the previous linker DNA fragment and allow for ligation of either of the two new linker sequences between the scTCR and the Sc-Fv.

EXAMPLE 6

Addition of a 3' Peptide Tag to sc Molecule Construct

In the "shuttle vector" design outlined above, a stop codon and splice site were introduced between the NruI and ClaI restriction sites as part of the PCR amplification of the scTCR with "back" primer KC208. To aid in downstream purification of the bispecific sc protein, a set of annealed oligos (KC237 and KC238) was designed to introduce a 3' EE tag (EEEEYMPME; SEQ ID NO. 7) with stop codon and splice site. The annealed oligo pair was cloned 5'NruI-3' ClaI into the "shuttle vector" already encoding for the complete bispecific sc molecule. Alternatively, oligos KC239 and KC240 (splice site only) were annealed and similarly cloned to allow expression of the bispecific sc molecule as a murine kappa light chain fusion protein.

EXAMPLE 7

Completion of p149 Bispecific sc Molecule

After cloning the scTCR, Sc-Fv, linker, and tag DNA fragments into the "shuttle vector" to complete the bispecific sc molecule design, the DNA was restriction digested (AgeI-ClaI) and cloned into the mammalian cell expression vector pSUN27 (FIG. 5) (previously described in the pending U.S. application Ser. No. 08/943,086 to create pBISP/149 (FIG. 6).

EXAMPLE 8

Construction of p149 scTCR/IgG Fusion Molecule

Figure 7B:
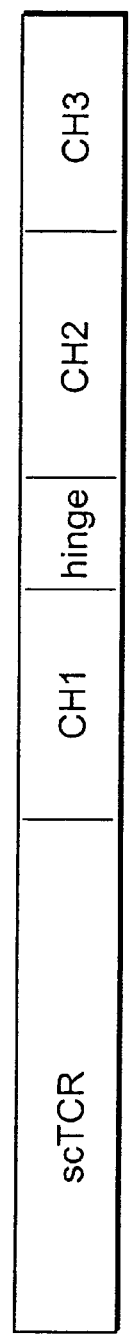

There has been recognition that the expression of the 145-2CII scSc-Fv alone, i.e. not as part of a bispecific sc molecule, is very low. Without wishing to be bound to theory, the low level of sc-Fv expression may be a limiting factor in the expression of bispecific molecules. Native 145-2C 11 hybridoma cell line was used as antibody source and cells were transfected with scTCR fused with murine IgG2b heavy chain (FIG. 7A–7B). The transfected hybridoma cell line should secrete some 145-2C11/scTCR chimeric molecules if the host's hamster IgG can pair efficiently with murine IgG2b heavy chain.

To clone the p149 scTCR as an IgG fusion, an internal EcoRI restriction site was first mutated using site-directed mutagenesis. Briefly, a pair of complimentary oligonucleotides, KC293 and KC294, were designed containing the desired mutation. The pNAG2 DNA construct was amplified by PCR with the primers using Pfu DNA polymerase. The resulting PCR product was digested with DpnI which digests the parental DNA template, leaving the mutated DNA intact. The mutated scTCR DNA was sequenced and then reamplified by PCR with primers KC276 and KC268 to generate a 5'NruI-3'EcoRI DNA fragment. The mutated scTCR DNA was cloned into the pGEM-T Easy Vector System for DNA sequence determination. The correct scTCR DNA was restriction digested and cloned into the mammalian cell expression vector pSUN7 to create the p149 scTCR/IgG fusion molecule.

EXAMPLE 9

Construction of DO11.10 scTCR/IgG Fusion Molecule

The pKC60 DNA construct was reamplified by PCR with primers KC275 and KC268 to generate a 5'NruI-3'EcoRI DNA fragment. The scTCR fragment was cloned into the pGEM-T Easy Vector System for DNA sequence determination. The correct scTCR DNA was restriction digested and cloned into the mammalian cell expression vector pSUN7 to create the DO11.10 scTCR/IgG fusion molecule (See FIGS. 7A and 7B).

EXAMPLE 10

Construction of the Murine IgG2b Expression Vector

The construction of the murine IgG2b (heavy chain) expression vector was as follows. The backbone of the vector was the plasmid pCDNA3 (Invitrogen). The plasmid was cut with HindIII and XhoI and a "light chain polylinker" DNA fragment was inserted to create the starting "light chain vector" pCDNA3.LCPL. This linker contained the restriction sites HindIII, KpnI, ClaI, PmlI, EcoRV, XmaI, BamnHI, and XhoI to facilitate subsequent cloning steps. A SmaI-BclI DNA fragment containing a light chain leader, mouse anti-CKMB kappa light chain genomic fragment, and 3' UTR was cloned into the EcoRV-BarnHI sites of pCDNA3.LCPL. Mutagenesis was then performed to eliminate an NruI MluI, and BstBI site and to introduce an NheI and BarnHI site to create the plasmid pCDNA3mut.LCPL.LCVK.

The "heavy chain vector" pCDNA3mut.HCPL was constructed from the pCDNA3mut.LCPL.LCVK plasmid by replacing the light chain expression region (HindIII-XhoI) with a "heavy chain polylinker" consisting of restriction sites HpaI, BspEI, EcoRV, KpnI, and XhoI. This plasmid was digested with EcoRv and KpnI. A SmaIKpnI digested DNA fragment containing a heavy chain leader and an anti-CKMB IgG2b mouse heavy chain genornic fragment (see Near et al., Molecular Immun., 1990) was then ligated into the EcoRV-KpnI digested plasmid. A KpnI-SalI oligonucleotide fragment containing a 3'UTR and a NotI site upstream of the SalI site was subsequently cloned into the KpnI-XhoI digested plasmid (knocking out the XhoI site) to create the plasmid pCDNA3mut.HCPL.HCV2b, also known as the murine IgG2b expression vector pSUN7 (FIG. 8).

EXAMPLE 11

Expression of Bispecific sc Molecules

CHO cells were prepared for transfection by washing with cold DPBS. The cells were resuspended in DPBS and mixed with 10–40 ug of PvuI linearized pBISP/149 or pBISP/DO11.10. After five minutes on ice, the cells were electroporated using a Gene Pulser (BioRad) set to deliver one pulse of 250 volts, 960$\mu$ Fd or 0.25$\mu$ Fd. The pulsed cells were placed on ice for five minutes. The cells were diluted into 10 ml of 10% IMDM medium (IMDM, 10% FBS, 2 mM glutamine, 5000 units/ml penicillin, 5000 ug/ml streptomycin) and grown in a T-25cm2 TC flask overnight at 37C with 10% CO2 The next day, the cells were plated in 96 well plates with neomycin selective medium (10% IMDM plus 0.75 mg/ml G418) and refed every 3–7 days.

Figure 9A:
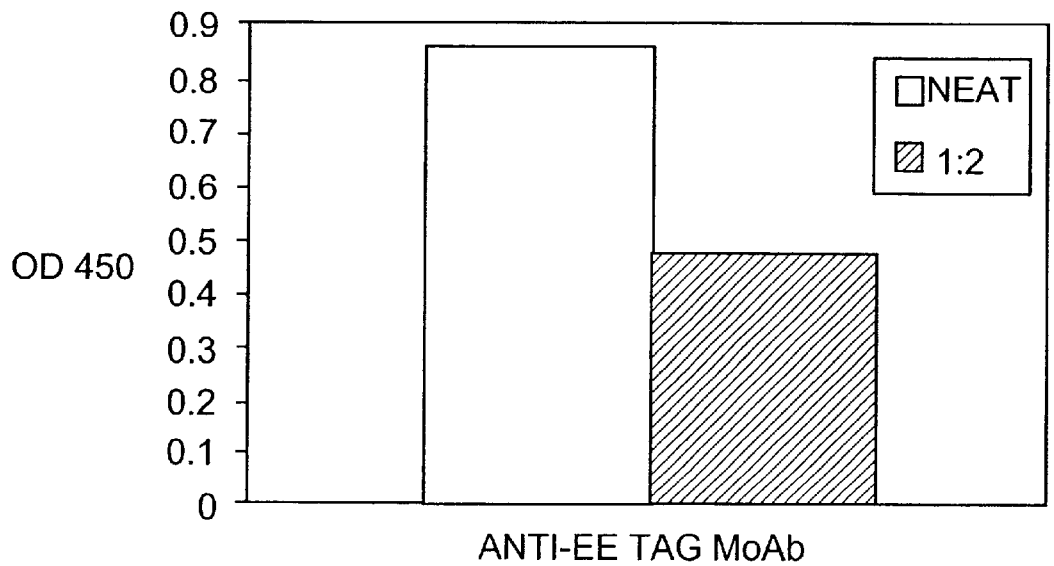
FIGS. 9A–9B are graphs showing results of ELISA assays used to detect BISP/149 fusion protein. Antibodies used were (9A) αEE (capture Ab) and $\alpha V_\alpha 2$ (B20.1, probe Ab), (9B) αVβ11 (RR3-15, capture Ab). RR3-15 is a monoclonal antibody specific for the αVβ11 chain. B20.1 is an monoclonal antibody specific for the αVα2 chain. Probe Ab is on the x-axis in FIG. 9B.
Figure 9B:
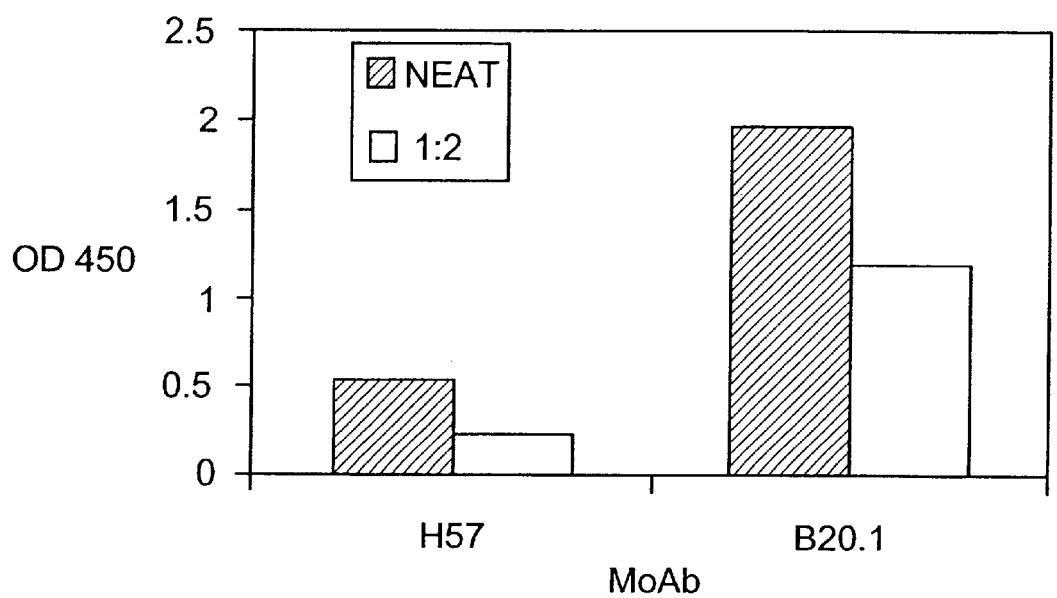
Figure 10A:
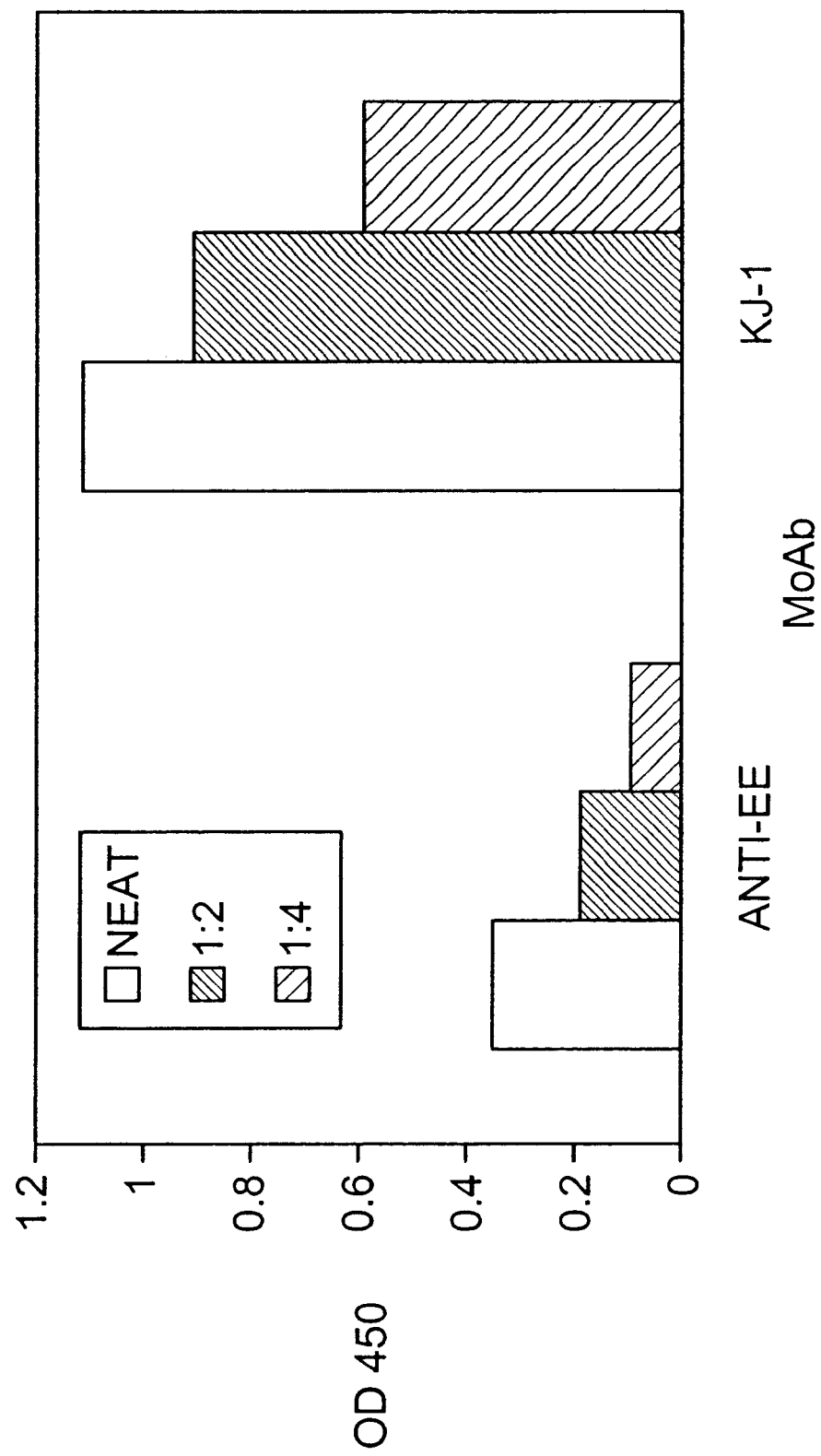
FIGS. 10A–10B are graphs showing results of ELISA assays used to detect BISP/DO11.10 fusion protein. Antibodies used were (10A) F23.1 (probe Ab) or (10B) H57–597 (probe Ab). Capture Ab is on the x-axis in FIGS. 9A and 9B.
Figure 10B:
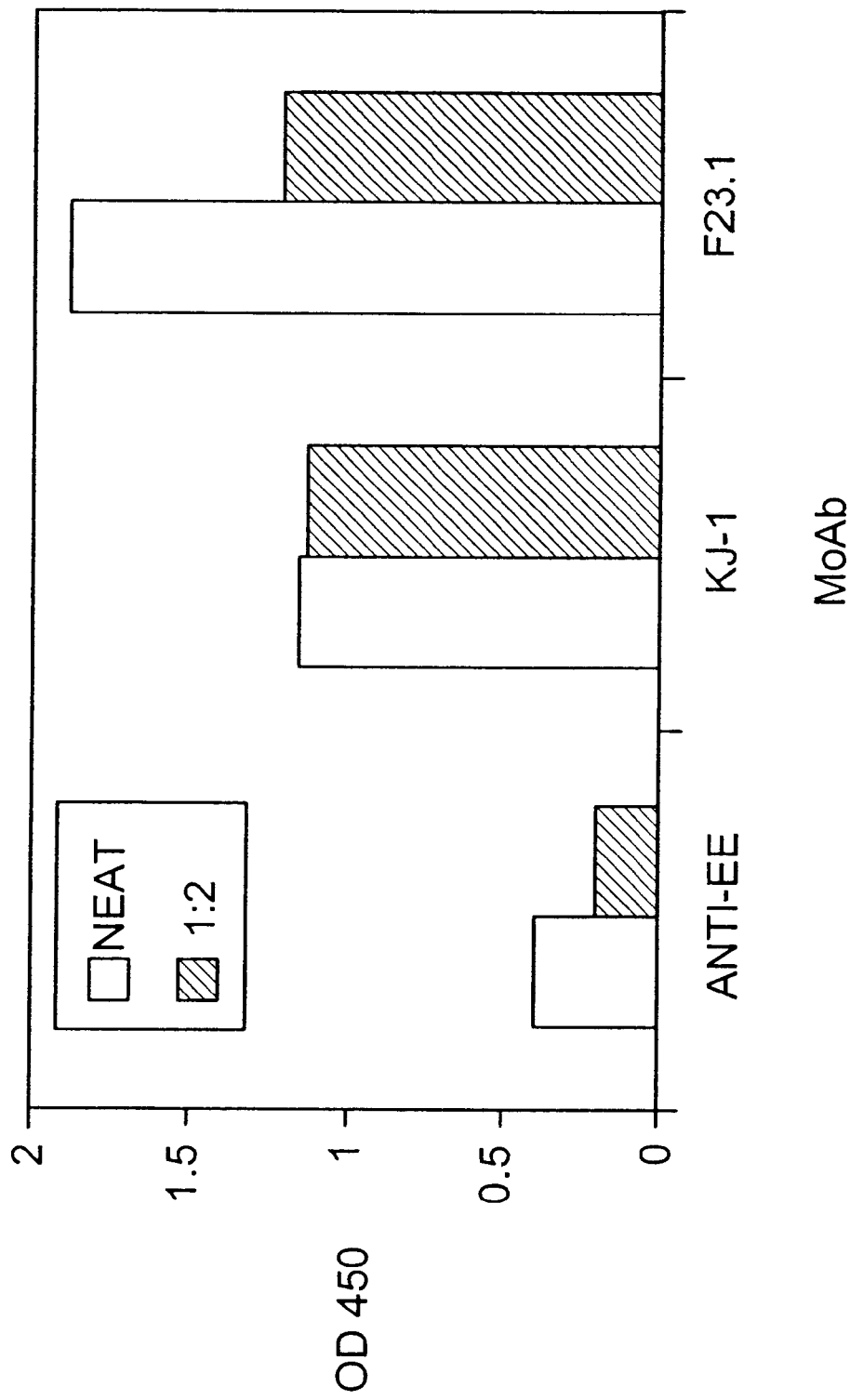

Transfectants were screened for expression of soluble bispecific sc molecules in an ELISA assay format. EE-tagged molecules were detected using an anti-EE tag antibody passively coated overnight onto a 96 well plate. On assay day, the plates were blocked with 10% FBS/PBS for one hour. The wells were washed and supernatant from the transfectants was added to the plate. After incubating and washing, biotinylated anti-C beta mAb H57-597 (cell line was purchased from ATCC) was added to the plate, followed by washing and incubation with streptavidin-HRP (Sigma). Positive wells were identified by the addition of TMB substrate, quenched with 1N sulfuric acid, and read at an absorbance of 450 nM. A small number of positive clones were selected for expansion and limiting dilution cloning was carried out to establish stably transfected cell lines (FIGS. 9A–9B).

Transfectants were also screened for the expression of bispecific sc molecules in an ELISA assay format using rnAbs which specifically recognize the scTCR, followed by detection with biotinylated anti-C beta mAb and streptavidin-HRP. For the p149 scTCR bispecific sc molecule, a conformational mAb to the V alpha domain (B20.1, Pharmagen) was used as the coating antibody. The DO11.10 bispecific sc molecules could be detected using the anti-idiotypic, anti-DO11.10 TCR mAb KJ-I (FIGS. 9A–B, 10A–B). Positive clones were detected as described above, expanded and primary cloned to establish stably transfected cell lines. It has been found that the scBISP molecules are expressed at high levels in mammalian cells (1 to 2 mg/l).

The following information will be helpful in understanding FIGS. 9A–B, 10A–B:

FIG. 9A

| Dilution | OD450 |
|---|---|
| 1:2 | 0.4755 |
| neat | 0.8545 |

FIG. 9B

| | OD450 | |
|---|---|---|
| Dilution | H57 | B20.1 |
| 1:2 | 0.206 | 1.21 |
| neat | 0.511 | 1.975 |

FIG. 10A

| | OD450 | |
|---|---|---|
| Dilution | Anti-EE | KJ-1 |
| 1:4 | 0.0825 | 0.5935 |
| 1:2 | 0.186 | 0.9095 |
| neat | 0.3435 | 1.1195 |

FIG. 10B

| | OD450 | | |
|---|---|---|---|
| Dilution | Anti-EE | KJ-1 | F23.1 |
| 1:2 | 0.185 | 1.143 | 1.227 |
| neat | 0.381 | 1.1655 | 1.898 |

EXAMPLE 12

Expression of Chimeric Bispecific Molecules

The 145-2CI 1 hybridoma cell line was transfected with either p149 scTCR/IgG fusion DNA or DO11.10 scTCR/IgG fusion DNA using the same method as described above for the bispecific sc molecule transfection.

Transfectants were screened for expression of soluble chimeric bispecific molecules in an ELISA assay format. 96 well plates were passively coated with goat anti-mouse IgG2b (Caltech). Incubation and washing steps were performed as described above. Goat anti-hamster IgG-HRP (Jackson Immuno.) was used to probe the wells (FIG. 11). Positive colonies were identified, expanded and primary cloned to establish stably transfected cell lines.

The following information will be helpful in understanding FIG. 11:

| | OD450 | |
|---|---|---|
| Construct | neat | 1:2 |
| BISP/149 | 0.6305 | 0.2985 |
| BISP/DO1 | 0.964 | 0.6983 |

EXAMPLE 13

Purification of Bispecific sc Protein

Bispecific sc proteins were purified from transfectant supernatant using standard affinity chromatography methods. For EE-tagged proteins, an anti-EE tag CNBr-coupled agarose column was used to enrich for full-length sc molecules. Supernatant was passed over the column bed one or more times. After washing with PBS, the bound protein was eluted off the column by the addition of high pH sodium bicarbonate/carbonate buffer and neutralized by the addition of a 1 to 10 dilution of 2 M Tris, pH8.0. The purified protein was buffer exchanged into PBS using a 30 kD MW cut-off concentration unit. The final protein concentration was determined by an OD280 reading. Western blot analysis (probed with anti-EE tag antibody) (FIG. 12) and coomassie-blue staining of the purified protein (FIG. 13) show enrichment for the full-length bispecific sc molecule.

EXAMPLE 14

Bispecific sc Molecule Stimulation of T Hybridoma Cells

Figure 13:
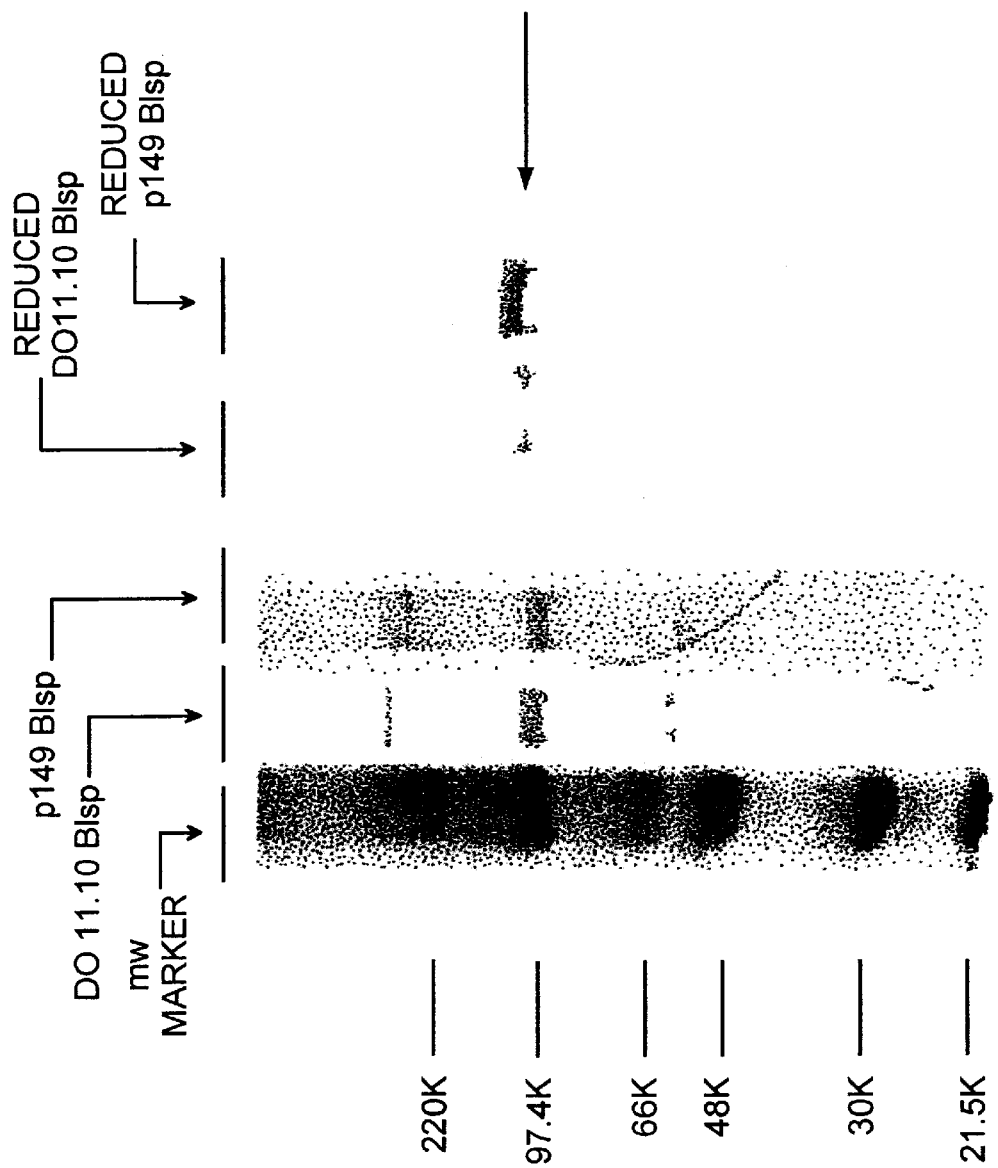
FIG. 13 is a representation of an SDS gel stained with Coomassie-blue. The gel shows expression of BISP/DO11.10 and BISP/p149 bispecific hybrid molecules. Also shown are reduced forms of the proteins (arrow).

T hybridoma cell stimulation assays were performed to assess whether the bispecific sc molecules displayed biological activity. We developed a working model system using the murine T cell hybridoma 2B4 (Matsui, et al., *PNAS USA*. (1994) 91, 12862) The 2B4 T cell hybridoma has an/β TCR consisting of V11.0 and Vβ3.0 and recognizes amino acid residues 88–104 of pigeon cytochrome C presented in the context of MHC class II molecule IE$^k$ Several different immobilized Abs specific for either the DO11.10 or 149 TCR were tested for cross-reactivity to 2B4 TCR, but turned out to be unreactive towards the 2B4 TCR. If an immobilized Ab demonstrated cross-reactivity for the 2B4 TCR, we would expect to observe stimulation of the T hybridoma cells and secretion of L-2 into the culture supernatant. The Abs evaluated included two specific for 149 TCR, the anti-V2 and anti-Vβ11, and two specific for the DO1 1.10 TCR, the anti-Vβ8.0 (F23.1) and the anti-idiotypic mAb (KJ-1). Also, we evaluated immobilized IA$^d$/OVA (the cognate MHC/peptide for the DO11.10 TCR), but did not observe any stimulation. We then immobilized these molecules and evaluated the activity of the DO11.10 and 149 bispecific sc molecules. To test the DO11.10-2C11 bisp. sc molecule, we coated wells with either KJ-1 or F23. 1. After incubation overnight with $10^5$ 2B4 cells using different amounts of bispecific, we assayed supernatant for the presence of IL-2 which is a good indicator of cell stimulation. As shown in FIG. 13, immobilized KJ-1 effectively activated the hybridoma cells. To evaluate whether a similar response could occur when using immobilized IA$^d$/OVA, we next incubated the 2B4 cells with bispecific molecules overnight in the presence of plate-bound IA$^d$/OVA. The presence of IL-2 in the supernatant was not detected in the IL-2 ELISA assay (FIG. 14) suggesting the TCR on the bispecific was not engaging the MHC/peptide ligand in a manner sufficient for cell stimulation. We proposed based on these findings and several others that it may be essential to improve the avidity of the bispecific sc molecules through dimerization using an antibody specific for the TCR but would not interfere with the bispecific binding to MHC/peptide. In our example, we chose the MR5-2 mAb (PharMingen)which has specificity for an epitope on Vβ8.2. After assaying under these modified conditions, we observed a signal in the wells containing immobilized IA$^d$/OVA but did not detect a signal in blank wells. Furthermore, in wells coated with KJ-1 mAb, the effect of cross-linking of the bispecific sc molecule generated a higher IL-2 output suggesting dimerization of the bispecific sc molecule leads to perhaps a stronger and/or different signaling and stimulation (FIG. 15).

Figure 14:
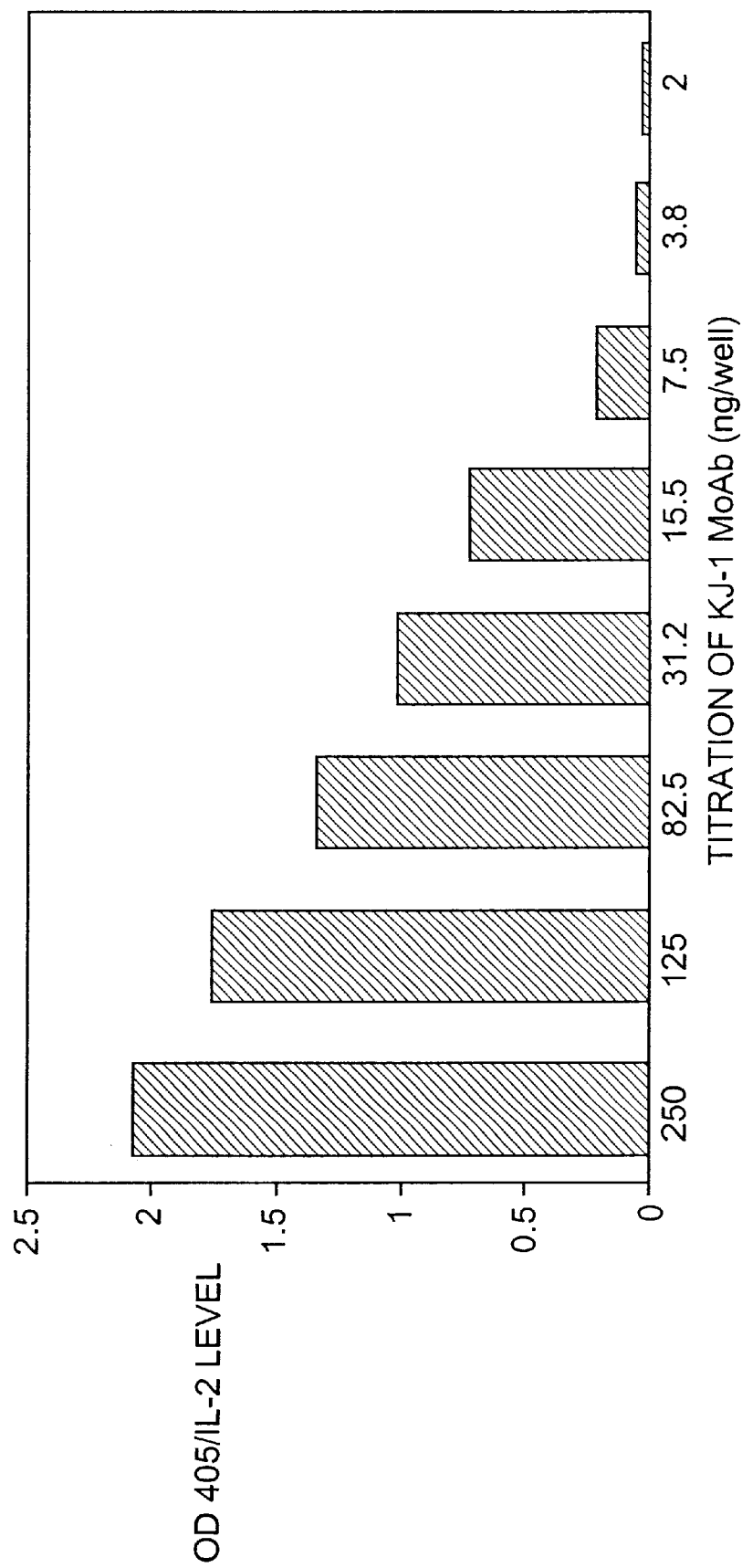
FIG. 14 is a graph showing IL-2 levels expressed by T-hybridoma cells as a function KJ-1 monoclonal antibody.
Figure 15:
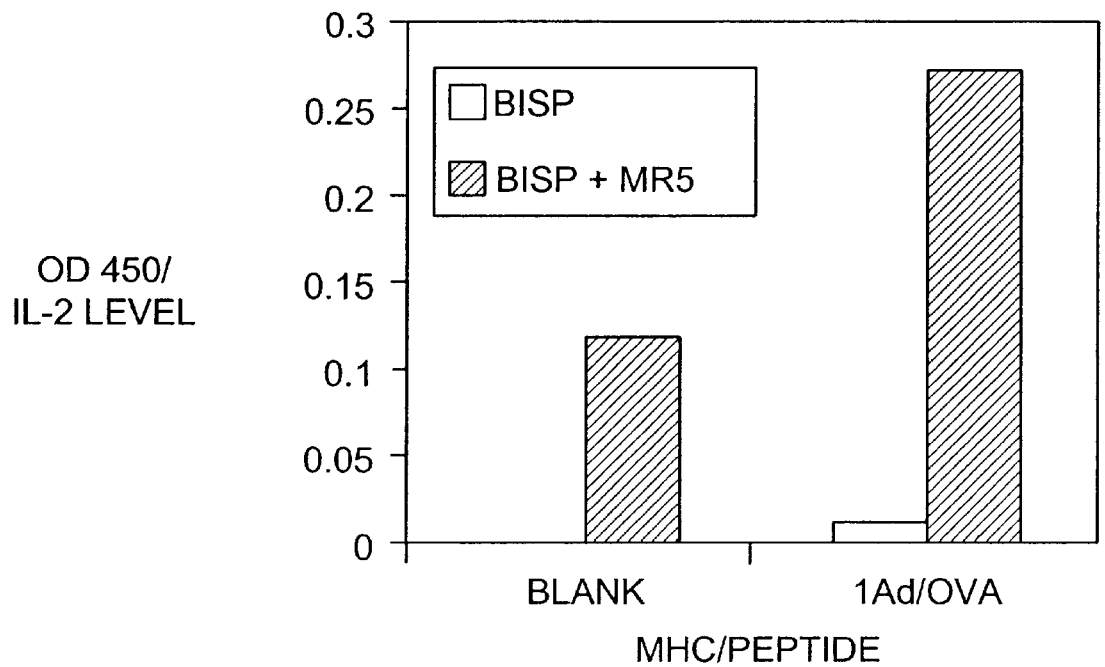
FIG. 15 is a graph showing IL-2 expressed by T-hybridoma cells as a function BISP or BPSP plus MR-5 antibody addition.

The following information will be helpful in understanding FIGS. 14 and 15:

FIG. 14

| BISP ng/well | OD450 |
|---|---|
| 2 | 0.013 |
| 3.9 | 0.036 |
| 7.8 | 0.196 |
| 15.6 | 0.72 |
| 31.2 | 1.01 |
| 62.5 | 1.3375 |
| 125 | 1.746 |
| 250 | 2.066 |

FIG. 15

| Construct | BISP | BISP + MR5 |
|---|---|---|
| Blank | 0 | 0.12 |
| IAd/OVA | 0.01 | 0.271 |

Figure 16:
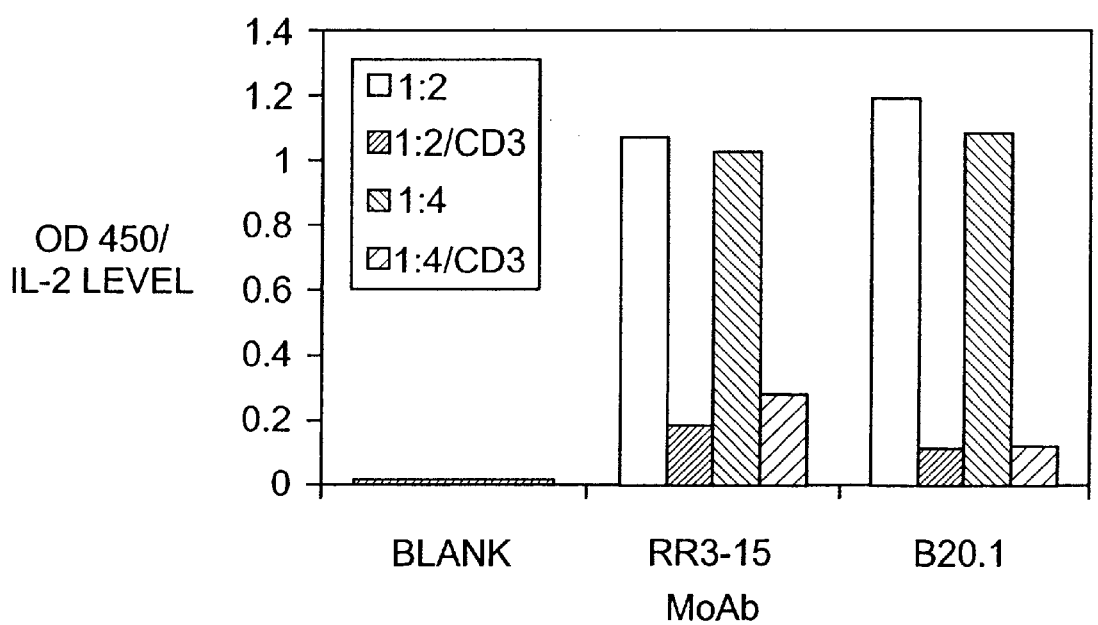
FIG. 16 is a graph showing IL-2 expression of T-hybridoma cells as a function of monoclonal antibody addition.

To evaluate the 149-2C 11 -EE-tag bispecific sc molecule, we coated wells with either anti-V 2.0 or anti-Vβ11.0 mAb. Blank wells were used as naive controls. The findings generated in these experiments were similar to those reported for the DO 11.10-2C 11 bispecific sc molecules and showed that only in the presence of immobilized Ab specific for the 149 TCR did we observe IL-2 production (FIG. 16). Furthermore, in this example, we demonstrated that the cross-linking by the bispecific to stimulate the T hybridomas could be effectively blocked using soluble anti-CD3 F(ab)'$_2$ 145-2C 11. These findings argue favorably for functional bispecific sc molecules and show the anti-CD3 portion of the bispecific acts by binding directly to the CD3 molecule on T cells (FIG. 16).

The following information will be helpful in understanding FIG. 16:

| | OD450 | | | |
|---|---|---|---|---|
| Construct | 1:2 | 1:4 | 1:2/CD3 | 1:4/CD3 |
| Blank | 0.01 | 0.01 | 0.01 | 0.01 |
| RR3-15 | 1.07 | 1.03 | 0.185 | 0.282 |
| B20.1 | 1.2 | 1.08 | 0.112 | 0.118 |

EXAMPLE 15

Flow Cytometric Analysis for Direct Cell Binding Studies

To demonstrate functionality of the scSc-Fv portion of the bispecific sc molecule, 2B4 T hybridoma cells were used in binding studies with the purified protein. 2B4 cells display CD3 on their surface and correctly folded 145-2C11 sc-Fv should recognize CD3ϵ. For each test sample, $10^6$ 2B4 cells were washed with cold DPBS and resuspended in 40 ul of 1% FBS/DPBS (resuspension and washing buffer) with or without the addition of purified bispecific sc protein. After incubation on ice, the cells were spun down gently and resuspended with 0.5 ug of biotinylated antibody (pBISP/ 149 was incubated with an antibody to the Va2 domain (B20. 1); pBISP/DO11.10 was incubated with an antibody to the Vβ8 domain (F23.1).) Samples were incubated on ice, spun down, and resuspended with streptavidin-cychrome (Becton Dickenson). After washing two times, the cells were resuspended again and then acquired/analyzed on a FACScan instrument (Becton Dickenson) using CellQuest software (Becton Dickenson).

Incubation of 2B4 cells with either the pBISP/149 or pBISP/DO11.10 purified protein resulted in significant shifts in cell staining. As more bispecific sc protein was added, the shift in fluorescence was more pronounced, demonstrating the ability of the scSc-F'v to bind to the CD3 on the cell surface (FIGS. 17–18).

Figure 19:
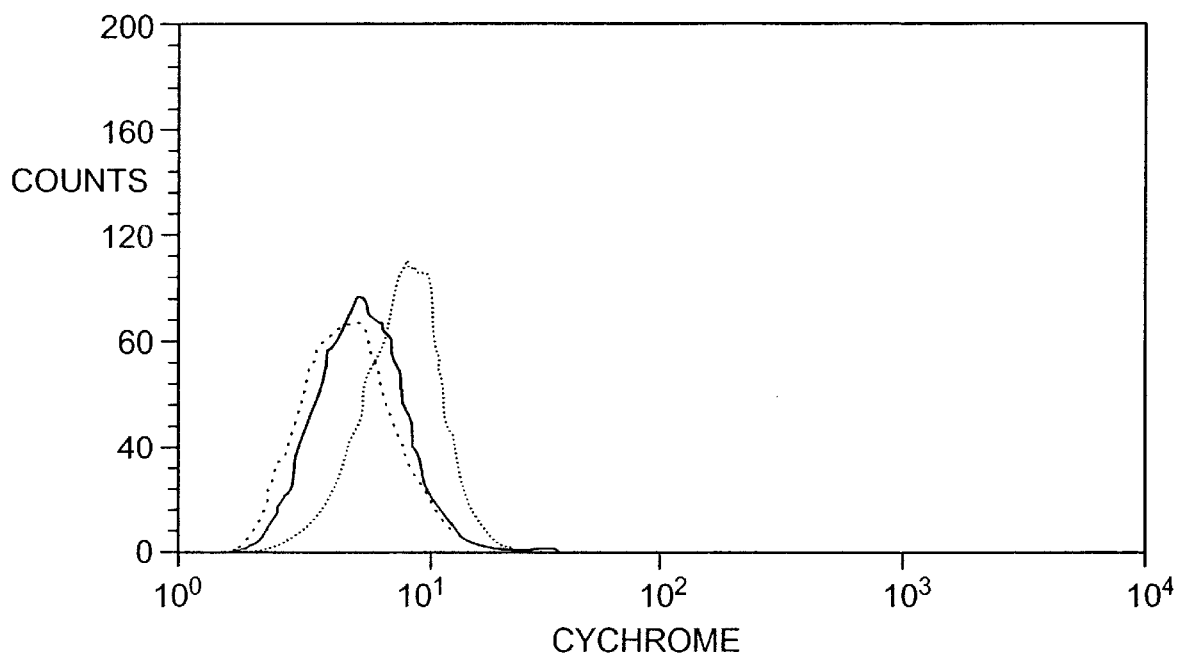
FIG. 19 is a graph showing flow cytometry binding studies between soluble α-CD3 and pBISP/149 purified protein.

The CD3 binding is specific and can be blocked by the addition of soluble anti-CD3 which competes with the bispecific sc molecules for binding sites on the 2B4 cell surface (FIG. 19).

Figure 17:
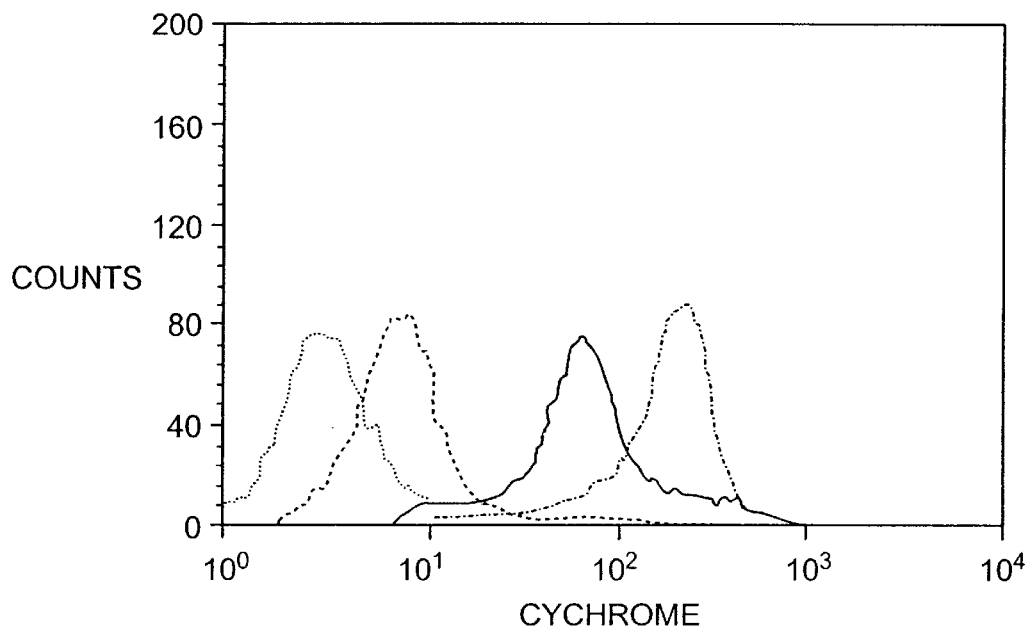
FIG. 17 is a graph showing by flow cytometry binding of pBisp149 cells to 2B4 T cells.
Figure 18:
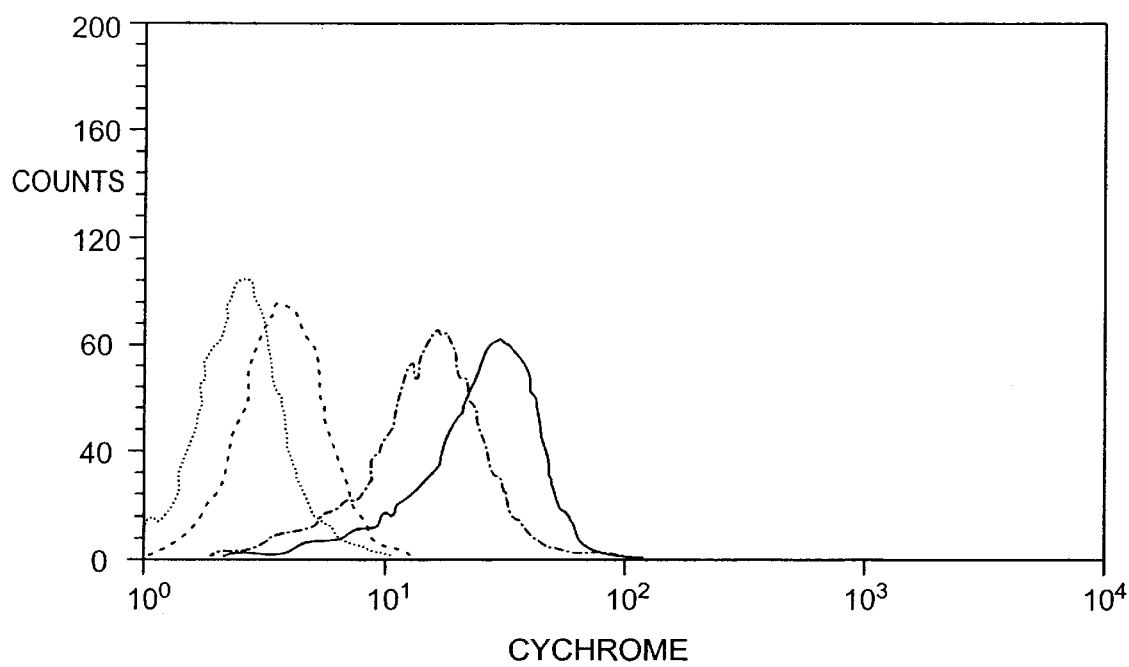
FIG. 18 is a graph showing by flow cytometry binding of the pBISP/DO11.10 purified protein between 2B4 cells T-cells.

FIGS. 17–19 are more fully understood in light of the following Tables I, II and III below.

TABLE 1

[FIG. 17]

| Key | Name | Parameter | Gate |
|---|---|---|---|
| — | 062498.001 | FL3-H | No Gate |
| — | 062498.002 | FL3-H | No Gate |
| — | 062498.003 | FL3-H | No Gate |
| — | 062498.004 | FL3-H | No Gate |

File: 062498.001 [No BISP] Sample ID: 2B4 ANTI-VA2-B-SA-CY Gate: No Gate

| Marker | Events | % Gated | % Total | Mean | Median | Peak Ch |
|---|---|---|---|---|---|---|
| All | 10000 | 100.00 | 100.00 | 7.78 | 3.19 | 1 |

File: 062498.002 [1X BISP] Sample ID: 2B4 1UL149 BISP ANTI VA2-B-SA-CY Gate: No Gate

| Marker | Events | % Gated | % Total | Mean | Median | Peak Ch |
|---|---|---|---|---|---|---|
| All | 10000 | 100.00 | 100.00 | 10.96 | 7.10 | 8 |

File: 062498.003 [10X BISP] Sample ID: 2B4 10UL 149BISP ANTI-VA2-B-SA-CY Gate: No Gate

| Marker | Events | % Gated | % Total | Mean | Median | Peak Ch |
|---|---|---|---|---|---|---|
| All | 10000 | 100.00 | 100.00 | 88.96 | 62.08 | 55 |

File: 062498.004 [25X BISP] Sample ID: 2B4 25UL 149BISP ANTI-VA2-B-SA-CY

| Marker | Events | % Gated | % Total | Mean | Median | Peak Ch |
|---|---|---|---|---|---|---|
| All | 10000 | 100.00 | 100.00 | 186.06 | 177.83 | 215 |

TABLE 2

[FIG. 18]

| Key | Name | Parameter | Gate |
|---|---|---|---|
| — | 062498.009 | FL3-H | No Gate |
| — | 062498.010 | FL3-H | No Gate |
| — | 062498.011 | FL3-H | No Gate |
| — | 062498.012 | FL3-H | No Gate |

File: 062498.009 [No BISP] Sample ID: 2B4 ANTI-VB8.2-B-SA-CY Gate: No Gate

| Marker | Events | % Gated | % Total | Mean | Median | Peak Ch |
|---|---|---|---|---|---|---|
| All | 10000 | 100.00 | 100.00 | 8.08 | 2.48 | 1 |

File: 062498.010 [1X BISP]Sample ID: 2B4 1UL DO11BISP ANTI-VB8.2-B SA-CY Gate: No Gate

| Marker | Events | % Gated | % Total | Mean | Median | Peak Ch |
|---|---|---|---|---|---|---|
| All | 10000 | 100.00 | 100.00 | 7.51 | 3.65 | 3 |

File: 062498.011[5XBISP] Sample ID: 2B4 5UL DO11BISP ANTI-VB8.2-B SA-CY Gate: No Gate

| Marker | Events | % Gated | % Total | Mean | Median | Peak Ch |
|---|---|---|---|---|---|---|
| All | 10000 | 100.00 | 100.00 | 19.31 | 14.46 | 15 |

File: 062498.012 [10XBISP]Sample ID: 2B4 10UL DO11BISP ANTI-VB8.2-B SA-CY Gate: No Gate

| Marker | Events | % Gated | % Total | Mean | Median | Peak Ch |
|---|---|---|---|---|---|---|
| All | 10000 | 100.00 | 100.00 | 28.29 | 24.56 | 27 |

TABLE 3

[FIG. 19]

| Key | Name | Parameter | Gate |
|---|---|---|---|
| ----- | 051398.003 | FL3-H | G1 |
| ------ | 051398.002 | FL3-H | G1 |
| ——— | 051398.005 | FL3-H | G1 |
| ——— | 051398.006 | FL3-H | G1 |

File: 051398.003 [No BISP/No αC3] Sample ID: 2B4 VA2 CYCH PI Gate: G1 Gated events: 9853 Total Events: 11724

| Events | % Gated | % Total | Mean | Median | Peak Ch |
|---|---|---|---|---|---|
| 9853 | 100.00 | 84.04 | 5.20 | 4.66 | 4 |

File: 051398.002 [BISP, No αCD3]Sample ID: 2B4 BISP VA2 CYCH PI Gate: G1 Gated events: 9907 Total Events: 11420

| Events | % Gated | % Total | Mean | Median | Peak Ch |
|---|---|---|---|---|---|
| 9907 | 100.00 | 86.75 | 8.21 | 7.84 | 9 |

File: 051398.005 [No BISP, No αCD3] Sample ID: 2B4 ANTI-CD3 VA2 CYCH PI Gate: G1 Gated events: 9905 Total Events: 11715

| Events | % Gated | % Total | Mean | Median | Peak Ch |
|---|---|---|---|---|---|
| 9905 | 100.00 | 84.65 | 5.60 | 5.14 | 4 |

File: 051398.006 [BISP, No αCD3] Sample ID: 2B4 ANTI-CD3 BISP VA2 CYCH PI Gate: G1 Gated events: 9933 Total Events: 11218

| Events | % Gated | % Total | Mean | Median | Peak Ch |
|---|---|---|---|---|---|
| 9933 | 100.00 | 88.55 | 5.43 | 5.00 | 5 |

EXAMPLE 16

T Cell Proliferation Assay

Figure 20:
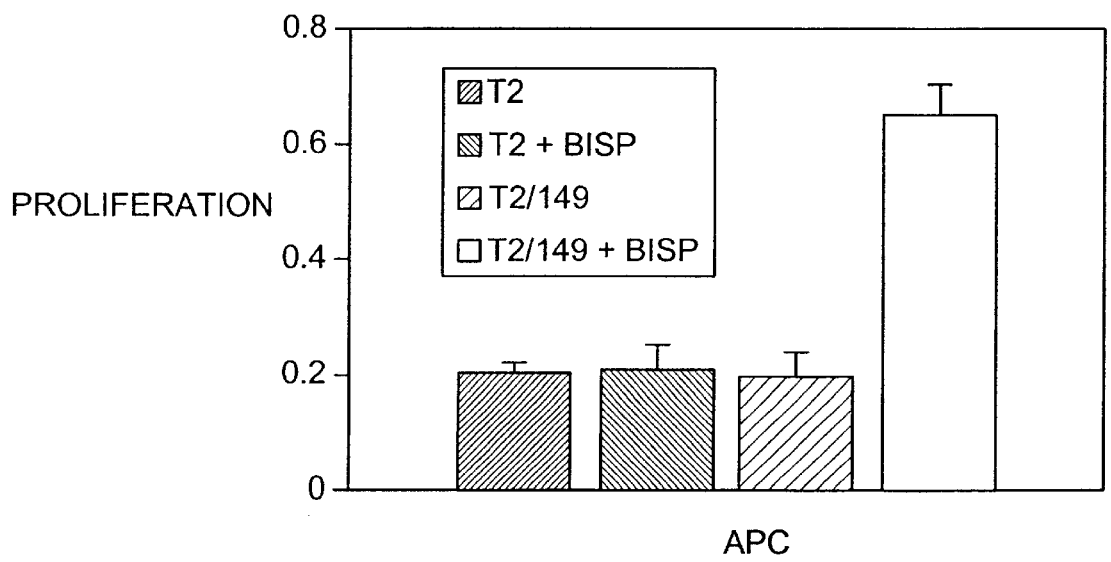
FIG. 20 is a graph showing results of a T-cell proliferation assay. BALB/c splenocytes were pre-stimulated with rIL-2 and incubated in the absence or presence of 10 μg/well of enriched scBisp 149 molecule with unpulsed target cells (T2) or p149 peptide pulsed T2 cells.

A T-cell assay was performed to determine whether the scBisp 149 molecule could mediate specific T cell activation. A proliferation assay was carried out using long-term cultured T cells, cultured in the presence of unpulsed or 149 peptide pulsed T2 (29) target cells that had been fixed in 1% paraformaldehyde prior to being used in the assay. Conditions were chosen to test whether the scBisp 149 molecule could activate T cells to proliferate when incubated with unpulsed or p149 peptide pulsed T2 target cells. The assay was carried out as follows. Briefly, spleens isolated from BALB/c mice were used to prepare splenocyte suspensions. RBCs were lysed using Gey's solution and the recovered splenocytes were then cultured for 10–15 days at $1.25\times10^6$ cells/mL in IMAM media supplemented with 10% Fetal Bovine Serum (FBI) containing 50 U/mL of murine rIL-2. Media was changed every 3 days and non-adherent cells were recovered, counted and resuspended at $1.25\times10^6$ cells/ml. Before using the cells in the proliferation assay, live cells were isolated on a Ficoll-Hypaque density gradient. The cultures were incubated for 3 days and T cell proliferation was measured using the colorimetric proliferation reagent WST-1 (Boehringer Manheim) according to the manufacturer's instructions. As shown in FIG. 20, only T cells incubated in the presence of the bispecific and the 149 peptide loaded T2 cells demonstrated significant proliferation, whereas the cultures incubated in the absence of either the 149 peptide or the scBishp 149 molecule did not exhibit proliferation. These data were significant because they illustrate "proof of principle" that scTCR used in a hybrid scBisp molecule format can mediate T cell responses to target cells presenting HLA-A2 and the specific peptide.

Spleenocytes were prepared from spleens isolated from Balb/c mice. Briefly, RBCs were removed by lysing using Gey's solution and the recovered spleenocytes were then cultured for 10–15 days at $1.25\times10^6$ cells/ml containing 50 U/ml of murine rIL-2. Media was changed every 3 days and non-adherent cells were recovered, counted and resuspended at $1.25\times10^6$ cells/ml. Before using the cells in the proliferation assay, we isolated the live cells (primarily T cells) on a Ficoll-Hypaque density gradient. In this example, we tested whether the 149-2C11 sc molecule could effectively recognize and bind to cognate MHC/peptide on presenting cells and facilitate cross-linking and activation of T cells. The proliferation assay was carried out using long-term cultured T cells, cultured in the presence of unpulsed or 149 peptide pulsed T2 target cells that were than fixed in 1% paraformaldehyde prior to being used in the assay. The cultures were incubated for 3 days and T cell proliferation was measured using the colorimetric proliferation reagent WST-1 (Borhringer Manheim) according to the manufacturer's instructions. After a 1 hour incubation at 37° C. 100 μl of supernatant was transferred to a flat bottom plate for reading at dual wavelength (450–620 nary). As shown in FIG. 19, T cells incubated in the presence of the bispecific and the 149 peptide loaded T2 cells demonstrated significant proliferation, whereas the cultures incubated in the absence of p149 peptide or bispecific did not exhibit any significant proliferation. These data support the T-hybridoma stimulation results described above and suggest the 149-2CII bispecific sc molecule is biologically active.

EXAMPLE 17

Profiling Cytokine Production

Another important parameter to evaluate is the ability of the bispecific sc molecule to mediate cytokine responses. Cytokine production can be detected by an ELISA assay specific for the cytokine of interest. 96 well plates are passively coated with anti-cytokine "A" overnight. On assay day, the wells are blocked with 10% FBS/PBS for one hour before adding supernatant from the proliferation-type experiment. Wells are probed with biotinylated anti-cytokine "A" followed by incubation with streptavidin-HRP. Positive wells are detected by the addition of ABTS substrate and read at an absorbance of 405 nM Cytokine production can also be looked at intracellularly using a saponin perrneabilization protocol. The cells are fixed with formaldehyde and then stained for the cytokine of interest in the presence of 0.5% saponin. Samples can then be analyzed using flow cytometry.

EXAMPLE 18

Measuring in vitro Cytotoxic Activity

One of the most important parameters to measure will be whether the bispecific sc molecule can mediate target or tumor cell killing. These assays will be carried out using a standard $Cr^{51}$ release CTL killing assay. The assay will be run as follows: Target cells (i.e. tumors) are first labeled with the isotope $Cr^{51}$. The $Cr^{51}$ is taken up by the tumor cells and is released into the culture supernatant upon cell lysis by the specifically activated cytotoxic T cells. The free or released $Cr^{51}$ is then counted and the specific cell lysis determined. We will use this type of an assay to evaluate the 149-2C11 sc molecule's ability to mediate target cell lysis. In our assay, we will use tumor cell lines (i.e. MDA-238, BT549, and MCF-7available from ATCC) known to express surface HLA-A2 and produce increased levels of wild-type p53. Controls will include A2 negative tumor lines (Ramos) and A2 positive but p53 negative cell lines (Saos-2).

EXAMPLE 19

Generation of Bispecific Molecules Through Chemical Cross-linking to Dendrimers To construct the bispecific molecule using a chemical cross-linking approach, the 2C11 mAb and the DO11.10 scTCR was used. Instead of directly cross-linking the two molecules, dendrimers were used as a scaffold to attach the molecules. Dendrimers are positively charged polyamines that are uniformly synthesized. Because the size and shape of each dendrimer derived during synthesis is exactly the same, the addition of proteins to the dendrimer results in the formation of homogenous molecules. The dendrimer also is inert and soluble under physiological conditions. Full-length 2C11 mAb was pepsin digested to produce F(ab)'$_2$ fragments which were isolated by gel filtration. The F(ab')$_2$ peak was pooled and buffered exchanged and Fab' molecules were produced by incubating the F(ab')$_2$ preparation under mild reducing conditions followed by purification on a sizing column. The isolated Fab' molecules were then directly coupled through free sulfhydryl groups to sulfo-succinimdyl (4-iodoacetyl) amino benzoate (sulfo-SIAB) derivatized dendrimers at a ratio of one Fab' to one SIAB derivatized dendrimer. Reactive-aldehyde groups were generated on terminal carbohydrate residues of the DO11.10 scTCR molecule for coupling to free amine groups on dendrimers. The scTCR was coupled to the 2C11 Fab' dendrimer at a 1:1 ratio to yield a bispecific molecule. The bispecific molecule was evaluated for its ability to activate T hybridoma cells in a stimulation assay. A working model system was developed using the murine T cell hybridoma 2B4. See Davis, M. M. et al. Ciba Fund. Synp. (1997). The 2B4 T cell hybridoma has an/β TCR consisting of V11.0 and Vβ3.0 and recognizes amino acid residues 88–104 of pigeon cytochrome C presented in the context of MHC class II molecule IE$^k$. When the bispecific/dendrimer was added to wells containing 2B4 T cells high levels of IL-2 were reported indicating stimulation had occurred. Further analysis revealed that the strong positive charge on the dendrimer complex caused non-specific binding to the T cell surface resulting in stimulation.

EXAMPLE 20

Mouse Models: Evaluation of the Bispecific Molecule's Activity in vivo

Three different established murine models have been established in order to evaluate the potential tumor suppression activity of the bispecific molecules. The first model includes using a normal mouse strain (i.e. Balb/c mouse) and injecting into this mouse pS3/HLA-A2 transformed EL-4 cells. These tumor cells proliferate quickly and within a few days kill the mouse. The following treatment protocol will be initially used. To evaluate our bispecific molecule, mice will be pre-treated with 0.5 mg of bispecific 149-2C11 sc molecule on day 0. The following day the mice will receive a second dose of the bispecific sc molecule along with the p53/A2 positive transfected EL-4 cells. The main parameter to measure in this model will be whether mice that receive the bispecific molecule survive for a longer period of time than control mice (ones that did not receive the bispecific molecule). Because the EL-4 tumor lines displays such rapid growth, we may be required to modify the treatment regimen for us to observe any increased survival time with the bispecific sc molecule.

The second model will use SCID mice implanted with murine tumors transfected to express HLA-A2 and human wild-type p53. This model usually runs for two to three weeks. Briefly, after implanting tumors, we can measure the growth of the tumor and then introduce into these mice purified murine CD8+ T cells and inject different amounts of the bispecific molecule. In some cases, we will need to pre-activate the T cells and this will be carried out by incubating T cells in vitro in the presence of rIL-2. We will then evaluate the affect on tumor growth and the change in survival time to determine whether the bispecific sc molecule has anti-tumor activity in vivo.

The third model and most relevant will evaluate the ability of the bispecific sc molecule to mediate tumor killing in in vivo of human tumors. SCID mice will be implanted with human breast carcinoma lines (i.e. MDA-238, BT549, MCf-7) and allowed to grow for 4 to 6 weeks. Then purified T cells and subset populations pre-activated in in vivo with rIL-2, will be introduced into the mice. The potential anti-tumor activity will be assessed by measuring tumor reduction and increased survival time. These studies will be used to determine whether a "humanized" version of the bispecific molecule should be constructed.

EXAMPLE 21

"Humanized" Bispecific sc Molecule

Because the antibody used in our current bispecific sc molecule is specific for murine CD3ε, we will have to modify it for use in treating human neoplasms. Furthermore, if we use hybridoma technology, we will most likely isolate murine mAbs specific to human TCRs or CD3 that will have to undergo "humanization". The humanization will be earned out doing CDR grafting. This usually has the negative affect of decreasing the binding avidity of the Ab. The TCR can be "humanized" primarily through swapping out the C beta constant domain with the human C beta constant region.

EXAMPLE 22

Display of sc-TCR Fusion Proteins on Bacteriophage

As disclosed in the pending U.S. application Ser. No. 08/813,781, it is possible to display a variety of sc-TCR constructs on the surface of fd bacteriophage. Briefly, the pending application discloses methods of expressing a desired three domain sc-TCR as a fusion with the major coat protein, pVIII, of filamentous phage. The rationale for this is to increase the valency of the scTCR on the surface of the phage which should result in an increase in the avidity of scTCR/pVIII for the MHC/peptide complex. As disclosed in the pending U.S. application Ser. No. 08/813,781, the sc-TCR fusion proteins on the bacteriophage display a functional TCR.

A. Characterization of displayed sc-TCR fusion protein
1. Western Blot Data

Many studies have been published showing scFv/pVIII fusion proteins expressed on the surface of phage. See Castagnoli et al., *J. Mol. Biol.*, (1991), 222: 301 and Huset et al., *J. Immunol.*, (1992) 149:2914. The pending U.S. application Ser. No. 08/813,781 discloses methods of making and using specific recombinant bacteriophages that display sc-TCR fusion proteins. Here, Western blot analysis was used to confirm display of the scTCR/pVIII molecule on the capsid coat of the phage. Briefly, bacteriophage were purified by means of a standard polyethylene glycol (PEG) precipitation procedure, and subsequently an aliquot of the purified phage was run on an SDS-PAGE gel. The scTCR/pVIII fusion was detected in the recombinant phage (but not in control phage expressing scTCR without the EE-tag) by probing the membranes with a mAb against the EE-tag sequence. Although several smaller bands representing breakdown products of the scTCR fusion were observed, the presence of a 50 kD protein band indicated a full length α/β scTCR had been incorporated into the phage capsid.

2. ELISA Data

As disclosed in the pending U.S. application Ser. No. 08/813,781, ELISA assays can be used to characterize recombinant bacteriophage that include a desired sc-TCR fusion protein. The conformational integrity of the V⊖8.2 chain was evaluated using two conformational dependent mAbs, MR5-2 and F23. 1; and the precise folding of the Vα13. 1, JαDO, Vβ8.2, Dβ1, and Jβ1.1 domains which form the CDR3 binding pocket of the receptor was assessed using the anti-idiotype mAb KJ1. Background signal was considered as phage binding to wells coated with either BSA or mAb anti-Vβ17 and was subtracted from the total signal observed. The four antibodies reacted specifically with the phage TCR indicating the scTCR/pVIII fusion was presented on the phage in the proper orientation.

B. Phage Panning

Panning of antibody and peptide libraries is firmly established as a method to reliably screen for specific binding molecules, Greenwood, supra. Methods for panning bacteriophage that display sc-TCR fusion proteins have been disclosed in the pending U.S. application Ser. No. 08/813, 781. Briefly, the methods include standard antibody, cell panning, and panning with sc-MHC/ peptide complexes disclosed in published PCT Application Ser. No. US 95/09816 as well as the pending U.S. application Ser. Nos. 08/382,454 and 08/596,387. Results from these enrichment studies correlate well with other published antibody panning findings. See, Winter et al., *Annu. Rev. Immunol.*, (1994), 12.

C. Blocking Assay

To characterize the MHC/peptide binding specificity of the TCR bearing phage, a competitive blocking assay. The competitive blocking assay has been disclosed in the pending U.S. application Ser. No. 08/943,086. Briefly, the objective of this example was to determine whether TCR carrying phage could compete with the native TCR on DO11.10 hybridoma T cells for binding to MHC/peptide complexes in a cell based assay. The results demonstrate the DO11.10 receptor on phage was functional and was able to discriminate between different peptide sequences.

To eliminate the possibility that the TCR carrying phage had perhaps affected the IL-2 production of the DO11.10 cells in a non-specific manner, wells were coated with mAb anti-CD3 epsilon to stimulate the hybridomas through the T cell receptor complex CD3 molecule to produce IL-2. Results from these experiments indicate that the phage did not have a non-specific inhibitory effect on the T hybridoma cells. Thus, the scTCRs are displayed on the surface of bacteriophage as functional molecules which are able to interact with specific MHC/peptide targets.

EXAMPLE 23

Cloning and Expression of the F23. 1 scFv

A preferred component of the polyspecific binding molecules disclosed herein is a an scFv with specificity for a particular sub-population of T cell receptors. As discussed a wide spectrum of different sc-Fv molecules can be used in accord with the present invention.

A more specific polyspecific binding molecule is a bispecific molecule which includes a single-chain form of the murine mAb F23.1. It is possible to clone and express such a sc-Fv by standard techniques. The native F23.1 antibody has been well characterized (1) and has been shown to activate Vβ8.2 bearing T cells by cross-linking the TCR on its surface, Hiller et al., *Biochem. J.*, (1991) 278: 573. The sc-Fv can be cloned and expressed by the following general steps.

1. cDNA Synthesis and Cloning of the Heavy and Light Chain Genes of F23.1

First strand cDNA synthesis can be accomplished with mRNA isolated from 107 F23.1 cells. Using primer JS300 (GAAX$_1$TAX$_2$CCCTTGACCAGGC wherein X$_1$=A,G and X$_2$=A, C, G; SEQ ID NO. 11), we synthesized heavy chain cDNA. This primer encodes for the first two amino acids of the heavy chain CH1 domain. The light chain cDNA was synthesized essentially the same way except we used primer OKA57 (GCACCTCCAGATGTTAACTGCTC; SEQ ID NO. 12) which is specific for the 3' end of framework four of the kappa chain.

Double stranded DNA was made by amplifying the cDNA as follows. Heavy chain was amplified by using primer set PMC18 (front) (CCCGGGCCACCATGGX$_1$ATGX$_2$AGCTGX$_3$GTX$_4$ATX$_5$CTC, wherein X$_1$=A,G; X$_2$=C,G; X$_3$=G,T; X$_4$=A,C; X$_5$=C,G; SEQ ID NO. 14 and JS300 and the light chain was amplified using primer set PMC14 (front) (CCCGGGCCACCATGGAGX$_1$CACAX$_2$X3CTCAGGTC, wherein X$_1$ and X$_3$ A,T, C or G are and X$_2$ is G,T; SEQ ID NO. 44) and OKA57. The amplified PCR products were then cloned into pGEM T-easy vector (Promega) and submitted for nucleotide sequence determination. A subsequent step will be to clone the heavy and light chains into a single-chain format for expression of scFv fragments.

EXAMPLE 24

Cloning and Expression of the F23.1 Antibody as a Single-chain Molecule

It is possible to clone a single-chain version of the F23.1 antibody which has been shown to recognize a conformational determinant on murine T cells bearing Vβ8.2 TCRs. In general, the Vβ8.2 family of TCRs is expressed at a frequency of 20% on T cells in most strains of mice, Staertz, U., *J. Immunol.*, (1995) 134, 3994. After the antibody gene has been cloned it will be possible to express the scFv molecule in *E. coli* for characterization.

The full length heavy and light chains (i.e. V/CH; V/CL) representing the F23.1 antibody have been cloned separately into vector pGEMT-easy (Promega) and the VH and VL genes have been confirmed by sequencing. The F23.1 antibody gene will be cloned into a single-chain molecule by splicing together the genes encoding the VH and VL domains. For example, one approach is to clone the scFv into the expression vector pEN2, for production of scFv fragments in *E. coli*. The pEN2 vector has been disclosed e.g., in U.S. Pat. No. 5,763,284.

The cloning protocol can be performed by using a two-step PCR amplification process. In the first round, the VH and VL genes will be separately amplified by using a specific primer set that anneals to the "front" and "back" of the VH and VL genes. In future experiments, T cells will be targeted to tumors, using as the antibody portion, antibodies reactive to CD3, CD4, and to particular TCRs. However, this particular antibody is preferred, e.g., because it can activate T cells, and more specifically activate CTLs. To make the scFv construct, a second step amplification will be carried out using overlapping PCR methodology to "splice" together the VH and VL genes. The two chains are linked using a 16 amino acid linker (G4SG4APG4S) containing the restriction site for the 8 base cutter AcsI. In those instances where overlapping PCR must be undertaken, two primers can be used as follows: JSS32(T)

(GGTGGCGGCGCGCCGGGAGGCGGCGGTTC; SEQ ID NO. 14) which overlaps within the linker sequence on the 5' end of the light chain and the bottom primer JSS33(B)

(GCCTCCCGGCGCGCCGCCACCACCGCTGCCA CCGCCACC; SEQ ID NO. 15) which overlaps within the linker region and runs into the 3' end of the heavy chain. The overlap PCR product is digested with SfiI and SpeI and then isolated by running the sample on a 1% agarose gel and excising the scFv band.

The scFv gene is then cloned into the expression vector pEN2 as a SfiI to SpeI fragment and induction of the protein is controlled by the phoA promoter. It is believed that approximately 50% of the scFv molecules can be expressed in E. coli as soluble and functional protein. If a particular host cell or culturing condition produce insoluble protein, the sc-Fv can be refolded according to standard techniques to obtain soluble protein.

EXAMPLE 25

Construction of scFv/pIII Fusions for Expression on Bacteriophage

As discussed, it is possible to express a variety of sc-Fv fusion proteins on the surface of a bacteriophage as one component of the phage capsid. For example, it is possible to make a bispecific bacteriophage endowed with binding affinity for an epitope on a desired T cell receptor and on a target tumor cell.

More specifically, to make an example of the bispecific phage, the F23.1 antibody molecule will be cloned as a scFv/geneIII fusion. As discussed in the pending U.S. application Ser. No. 08/813,781, the geneIII protein is a 406 amino acid protein that is expressed as five copies on the surface of phage. An specific fd tet bacteriophage has been modified by adding convenient SpeI and NotI sites for cloning scFv genes as pIII fusions. By amplifying the F23.1 scFv gene from the pEN2 vector described above in Example 23, the gene will be cloned as an SpeI-NotI fragment into the N-terminal region of the wild-type pIII protein. Because induction of the scFv/pIII fusion is under the control of the tac promoter, expression will occur after the addition of 1 mM of IPTG. Generally, it has been reported that one copy of the scFv is displayed per phage as a gene III fusion. Therefore, the phage represent an attractive system to use for displaying single copies of the antibody molecule. This will help to minimize non-specific interactions and will allow the phage to closely mimic the ideal concept of displaying monovalent scFv molecules. See FIGS. 2D–2E for examples of specific sc-TCR fusion constructs.

1. Modifications to the scFv Construct by Adding Specific Tags

Several alternate ways will be used to make scFv molecules containing carboxyl terminal region tags. DNA encoding for the sequence of each tag will be fused to the 3' end of the light chain gene. The inclusion of a carboxyl terminal tag will result in detection of the molecule. Examples of tags include the KT3, TPPPEPET; (SEQ ID NO. 9,); 6×His, GMAHHHHHH; (SEQ ID NO. 8,) avidin; ARKCSLTGKWTNDLGSNMT; (SEQ ID NO. 6) fos, BirA, LXLIFEAQKIEWR (SEQ ID NO. 5) or jun. The molecule KT3EE (EEEEYMPME, SEQ ID NO. 7) may also be used in some instances. See Hiller et al., (1991), *Biochem, J.*, 278, 573; Patel et al., 1994), *Proc. Natl. Acad. Sci. USA*, (1994), 91, 7360; Kruif et al., *J. Biol. Chem.*, 271: 7630 and Schatz, P., Bio/Technology, (1993) 11, 1138.

EXAMPLE 26

Purification and Analyses of scFv F23.1 for Binding to Native and Single-chain TCR Metal-chelating chromatography has become a widely used procedure in the purification of recombinant proteins. This technology can be used to purify the scFv molecule. A 6×His tag has been engineered into the design of the scFv molecule to allow simple purification on a Ni2+NTA column. Preparation of the soluble fraction is accomplished by suspending E. coli cell paste in extraction buffer and cells are then lysed in a French press. The sample will then be applied to a Ni2+NTA column under conditions that allow for binding of 6×His tagged proteins and bound protein will be eluted using imidazole, pH 7.4. Samples will be analyzed for purity by SDS-PAGE and coomassie blue staining of the gel. Western blot analysis will be used to evaluate the integrity of the scFv by probing membranes with an antibody specific for a KT3 tag.

If desired, additional purification of the sc-Fv may be performed as follows. For example, an affinity column can be made by first covalently coupling the anti-EE tag mAb to protein-A sepharose beads. The anti-EE tag coated beads will then be used to capture the purified DO11.10 scTCR which will then be cross-linked to the mAb. The column can be used to purify the scFv (F23.1) antibody because it has specificity for the Vβ8.2 domain. This two-step purification scheme will yield a homogeneous scFv preparation.

To assess whether the purified scFv F23.1 is functional, plasmon surface resonance studies can be used to measure the binding constant associations of the scFv to scTCR (DO11.10) protein biotinylated and coupled to a streptavidin coated chip. As a control, the binding constant association of the native F23.1 antibody can be determined for comparison with the recombinant F23.1 antibody. See the pending U.S. application Ser. No. 08/813,781 for disclosure relating to performing this assay.

In addition to comparing the binding profiles between the native and recombinant F23.1 antibodies for the scTCR, it is possible to investigate the ability of these antibodies to bind to the native TCR on DO11.10 T cells. Flow cytometric analysis will be employed to detect binding of biotin labeled antibodies to the receptors on the cells. It is anticipated that the data from these experiments will predict the ability of the scFv fragment to activate T cells through binding of the Vβ8.2 bearing receptors. Disclosure relating to performing flow cytometric analysis can be found in the pending U.S. application Ser. Nos. 08/813,781 and 08/943,086.

EXAMPLE 27

Expression of the F23.1 scFv as a GeneIII Fusion on the Surface of Bacteriophage As discussed, the F23.1 sc-Fv can be expressed as a pIII fusion for display on the surface of bacteriophage. This approach represents a unique way to rapidly characterize the scFv molecule before making the effort to express and purify the antibody from E. coli. To accomplish many of the characterization studies described, sufficient numbers of phage can be obtained from 2-to 5 liters of an overnight culture. Moreover, as an alternative to purying the sc-Fv molecules as described in Example 6 (instead of using an elaborate affinity purification system as we have described for purifying scFv molecules from E. coli lysate), the purification of the bacteriophage can be easily accomplished by two rounds of polyethylene glycol (PEG) precipitation. If it is necessary to further purify the phage, enrichment on a CsCl gradient can be used. After cloning, the phage expressing the scFv can be produced, purified and available for testing within a shorter period of time compared to expression and purification of soluble scFv molecules. Cell binding assays can be used to test whether phage are expressing scFv/pIII fusions. This will be carried out by incubating phage with DO11.10 T cells and assaying for bound phage using a biotin labeled antibody specific for phage. More specific disclosure relating to performing the cell binding assays can be found in the pending U.S. application Ser. No. 08/813,781. Detection of antibody labeled phage will be analyzed by adding a streptavidin-phycoerythrin (PE) conjugate. scFv molecules expressed as pIII fusions normally retain conformational activity and in many instances perform better than the recombinant Fv fragment. One goal is to confirm that a functional scFv fragment is displayed only on the tip of the phage.

EXAMPLE 28

Ability of Recombinant Bacteriophage to Activate T Cells

The F23.1 sc-Fv molecule preferably exhibits an ability to stimulate DO11.10 T cell hybridomas or to activate a population of non-enriched murine T cells. All experiments will use the native F23.1 antibody as a positive control, especially since reports have shown it can activate T cells. See Staerz, supra. In the first experiment, bacteriophage expressing the scFv/fusion will be adsorbed directly to the plastic well or immobilized by capturing with an antibody to the phage. Another approach will use the phage in suspension. Briefly, 105 DO11.10 T hybridoma cells will be added to wells containing phage as described above. After an overnight incubation, plates will be centrifuged to pellet cells and the supernatant isolated and assayed for IL-2 using an anti-IL-2 ELISA.

The second experiment will use T cells isolated from Balb/c mice. Two parameters will be measured to evaluate activation. The first parameter will be to assay IL-2 levels after incubating 106 naive cells in the presence of the antibody phage. The second method will be to stain naive cells for activation markers identified on T cells after incubation with the phage. It is possible to assay a number of surface markers that are expressed or up-regulated after activation. Parallel studies can be performed using the purified scFv instead of the phage. However, in this case it is preferred that the molecule will be immobilized with an mAb having specificity for the KT3 tag located at the carboxyl terminal region of the scFv molecule. From these two experiments, it is possible to evaluate the effectiveness of using scFv phage to stimulate or activate T cells.

EXAMPLE 29

Engineering Bispecific Hybrid Molecules (i.e. Bispecific Bacteriophage) and Characterization of its Tumor Killing Properties in vitro One objective of the present invention is to illustrate that the present polyspecific binding molecules and particularly the sc-TCR/sc-Fv bispecific molecules can kill tumor cells in vitro. The bispecific molecules can be made in a number of ways in accord with the invention including the following specific methods.

One approach to making bispecific molecules will be to utilize bacteriophage as a vehicle for displaying simultaneously both the scTCR and the scFv. Bispecific phage will be made by infecting K91 E. coli cells previously transformed with the pSUN26 phagemid vector, and then with scFv/pIII expressing phage. After PEG purification of the bispecific phage, the phage can be characterized to ensure both scTCR and scFv fusions are expressed on the surface. This will be done by ELISA assay in which wells will be coated at lug/well of purified scTCR (DO11.10) bearing the V 8.2 epitope. Phage that express a functional scFv F23.1 should bind to the DO11.10 scTCR. Streptavidin-HRP will be used to detect the p-149 scTCR displayed on the surface of phage. Anti-V 2.3 or anti-V 11.0 mAb (PharMingen) will be used followed by streptavidin-HRP.

EXAMPLE 30

Strategies for Linking scTCR and scFv Molecules with Joining Molecules

As discussed, the present polyspecific binding molecules can be joined by one or a combination of different joining molecules. Several specific joining molecules include immunoglobulin heavy chains and the molecules disclosed above that are capable of forming specific binding complexes.

For example, one specific type of joining molecule is the biotin binding motif of avidin. This joining molecule has been genetically encoded into the design of the p-149 scFv molecule. Therefore, scFv molecules will be expressed with a sequence of amino acids derived from avidin which contains a biotin binding motif (See, Hiller et al., *Biochem.*, (1991), 278, 573–585. The scTCR will be expressed containing the carboxyl terminal biotinylation sequence, BirA, see Schatz, P., *Bio/Technology*, 11, 1138–1143 (1993), as described in aim 2, that can bind free biotin in vivo or in vitro in the presence of biotin ligase, Schatz, P. supra, an enzyme capable of adding a single biotin molecule to the BirA site. Monovalent bispecific molecules can be efficiently formed using this approach. An attraction for using this approach is the strong interaction between avidin and biotin (10–15 M) (see, Green, N., *Methods Enzymol.*, (1990) 184, 85–133 and the high probability of forming heterodimers (scTCR:scFv) compared to homodimer formation (scTCR:scTCR or scFv:scFv).

Use of additional joining molecules are contemplated. For example, another approach can be used in which it is possible to link a desired sc-TCR and sc-Fv together by using the fos/jun leucine zipper, see for example, Patel et al., *Proc. Natl. Acad. Sci. USA*, (1994) 91, 7360–7364 and Segal et al., *Annals. New York Academy of Sciences*, (1991) 636, 288–294. Again, each molecule would be made separately. For example, the scFv will have a carboxyl terminal fos sequence and the scTCR will be engineered to have a carboxyl terminal jun sequence. A single cysteine residue will flank either side of the fos and jun moieties to facilitate the formation of disulfide bonds to enhance the stability of the interaction. Also like the avidin/biotin approach, this technology has the advantage of producing heterodimers at a very high frequency compared to homodimer formation, Patel et al., supra.

The invention has been described with reference to preferred embodiments thereof, however, it will be appreciated that those skilled in the art, upon consideration of this disclosure, may make modifications and improvements within the spirit and scope of the invention. All documents referenced herein are incorporated by reference.

What is claimed is:

1. A soluble single-chain polyspecific binding protein comprising at least one single-chain T-cell receptor (sc-TCR) or fragment thereof covalently linked through a first peptide linker sequence to at least one single-chain antibody (sc-Ab) or fragment thereof, wherein the sc-TCR fragment specifically binds to a major histocompatibility (MHC) or human-leukocyte-associated antigen (HLA) complexed with peptide with at least about 70% affinity when compared to the specific binding of the full-length V-α and V-β chain and further wherein the sc-Ab fragment specifically binds to the specific antigen with at least about 70% affinity when compared to the specific binding of the full-length immunoglobin chain.

2. The binding protein of claim 1, wherein the sc-TCR comprises a V-α chain covalently linked to a V-β chain by a second peptide linker sequence.

3. The binding protein of claim 2, wherein the C-terminus of the V-α chain is covalently linked by the second peptide linker sequence to the N-terminus of V-β chain.

4. The binding protein of claim 2, wherein the C-terminus of the V-β chain is covalently linked by the second peptide linker sequence to the N-terminus of the V-α chain.

5. The binding protein of claim 2 further comprising a C-β chain covalently linked between the C-terminus of the V-β chain and the N-terminus of the first peptide linker sequence, wherein the C-β chain is between about 50 to about 126 amino acids in length.

6. The binding protein of claim 2 further comprising a C-α chain covalently linked between the C-terminus of the V-α chain and the N-terminus of the second peptide linker sequence, wherein the C-α chain is between about 5 to about 25 amino acids in length.

7. The binding protein of claim 5 further comprising a C-α chain covalently linked between the C-terminus of the V-β chain and the N-terminus of the second peptide linker sequence, wherein the C-α chain is between about 5 to about 25 amino acids in length.

8. The binding protein of claim 6 or 7, wherein the C-α chain fragment is between about 5 and 25 amino acids in length.

9. The binding protein of claim 5, wherein the C-β chain fragment is between about 50 and 126 amino acids in length.

10. The binding protein of claim 2, wherein the first and second peptide linker sequences are each independently between about 2 and 25 amino acids in length.

11. The binding protein of claim 2, wherein the single-chain antibody comprises a first and a second immunoglobulin variable chain covalently linked together by a third polypeptide linker sequence.

12. The binding protein of claim 11, wherein the first variable chain is a light chain ($V_L$) and the second variable chain is a heavy chain ($V_H$).

13. The binding protein of claim 12, wherein the C-terminus of the $V_L$ chain is covalently linked by the third peptide linker sequence to the N-terminus of $V_H$ chain.

14. The binding protein of claim 12, wherein the C-terminus of the $V_H$ chain is covalently linked by the third peptide linker sequence to the N-terminus of the $V_L$ chain.

15. The binding protein of claim 12, wherein the third peptide linker sequence is between about 2 and 25 amino acids in length.

16. The binding protein of claim 12, wherein the C-terminus of the sc-TCR V-β chain is covalently linked to the third polypeptide linker sequence which sequence is linked to the N-terminus of the $V_H$ or $V_L$ chain.

17. The binding protein of claim 16, wherein the C-terminus of the sc-TCR V-β chain is covalently linked to a C-β chain which chain is covalently linked to the third polypeptide linker sequence which sequence is linked to the N-terminus of the $V_H$ or $V_L$ chain.

18. The binding protein of claim 17, wherein the sc-TCR comprises a V-α chain covalently linked to a C-α chain or fragment, wherein the C-α chain is covalently linked between the C-terminus of the V-α chain and the N-terminus of the second peptide linker sequence, wherein the C-α chain is between about 5 to about 25 amino acids in length.

19. A soluble single-chain polyspecific binding protein comprising covalently linked in sequence: 1) a sc-TCR or fragment thereof, 2) a first polypeptide linker sequence, and 3) a single-chain antibody or fragment thereof, wherein the sc-TCR fragment specifically binds to a major histocompatibility (MHC) or human-leukocyte-associated antigen (HLA) complexed with at least about 70% affinity when compared to the specific binding of the full-length V-α and V-β chain and further wherein the sc-Ab fragment specifically binds to the specific antigen with at least about 70% affinity when compared to the specific binding of the full-length immunoglobin chain.

20. The binding protein of claim 19, wherein the sc-TCR further comprises covalently linked in sequence: 4) a V-α chain, 5) a second peptide linker sequence, 6) a V-5 chain, and 7) a C-β chain, wherein the C-β chain is between about 50 to about 126 amino acids in length.

21. The binding protein of claim 19, wherein the sc-TCR further comprises covalently linked in sequence: 4) a V-β chain, 5) a second peptide linker sequence, 6) a V-α chain, and 7) a C-β chain, wherein the C-β chain is between about 50 to about 126 amino acids in length.

22. The binding protein of claim 20 further comprising a C-α chain thereof covalently linked between the V-α chain and the first polypeptide linker sequence, wherein the C-α chain is between about 5 to about 25 amino acids in length.

23. The binding protein of claim 19, wherein the single-chain antibody further comprises covalently linked in sequence: 4) a $V_H$ chain, 5) a third polypeptide linker sequence, and 6) a $V_L$ chain.

24. The binding protein of claim 19, wherein the single-chain antibody further comprises covalently linked in sequence: 4) a $V_L$ chain, 5) a third polypeptide linker sequence, and 6) a $V_H$ chain.

25. The binding protein of claim 19 further comprising at least one protein tag covalently linked thereto.

26. The polyspecific binding protein of claim 1, wherein at least the sc-TCR of the protein has been humanized.

27. The binding molecule of claim 26, wherein sc-TCR and single-chain antibody regions have been humanized.

28. The soluble fusion protein of claim 25, wherein the protein tag is a detectably labeled molecule suitable for diagnostic or imaging studies.

29. The single-chain polyspecific binding protein of claim 1, wherein the single-chain T-cell receptor (sc-TCR) is a p149 sc-TCR.

30. A soluble single-chain polyspecific binding protein comprising at least one single-chain T-cell receptor (sc-TCR) or fragment thereof comprising a V-α and a V-β chain in which the V-β chain is covalently linked to a C-β chain having between about 50 to about 126 amino acids, the C-β chain being further linked through a first peptide linker sequence to at least one single-chain antibody (sc-Ab) or fragment thereof, wherein the sc-TCR fragment specifically binds to a major histocompatibility (MHC) or human-leukocyte-associated antigen (HLA) complexed with peptide with at least about 70% affinity when compared to the specific binding of the full-length V-α and V-β chain and further wherein the sc-Ab fragment specifically binds to the specific antigen with least about 70% affinity when compared to the specific binding of the full-length immunoglobin chain.

31. A soluble single-chain polyspecific binding protein comprising at least one single-chain T-cell receptor (sc-TCR) or fragment thereof covalently linked through a first peptide linker sequence to at least one single-chain antibody (sc-Ab) or fragment thereof, wherein the sc-TCR is encoded by DNA without sequence encoding a transmembrane domain, wherein the sc-TCR fragment specifically binds to a major histocompatibility (MHC) or human-leukocyte-associated antigen (HLA) complexed with peptide with at least about 70% affinity when compared to the specific binding of the full-length V-α and V-β chain and further wherein the sc-Ab fragment specifically binds to the specific antigen with at least about 70% affinity when compared to the specific binding of the full-length immunoglobin chain.

* * * * *

UNITED STATES PATENT AND TRADEMARK OFFICE
CERTIFICATE OF CORRECTION

PATENT NO. : 6,534,633 B1
DATED : March 18, 2003
INVENTOR(S) : J. Weidanz et al.

It is certified that error appears in the above-identified patent and that said Letters Patent is hereby corrected as shown below:

Column 78,
Line 17, "6) a V-5 chain," should be -- 6) a V-$\beta$ chain, --.

Signed and Sealed this

Fifth Day of August, 2003

JAMES E. ROGAN
*Director of the United States Patent and Trademark Office*

SEQUENCE LISTING

<160> NUMBER OF SEQ ID NOS: 44

<210> SEQ ID NO 1
<211> LENGTH: 20
<212> TYPE: PRT
<213> ORGANISM: Homo sapiens

<400> SEQUENCE: 1

Gly Gly Gly Gly Ser Gly Gly Gly Ser Gly Gly Gly Ser Gly
 1               5                  10                 15

Gly Gly Gly Ser
            20

<210> SEQ ID NO 2
<211> LENGTH: 15
<212> TYPE: PRT
<213> ORGANISM: Homo sapiens

<400> SEQUENCE: 2

Gly Gly Gly Gly Ser Gly Gly Gly Ser Gly Gly Gly Gly Ser
 1               5                  10                 15

<210> SEQ ID NO 3
<211> LENGTH: 12
<212> TYPE: PRT
<213> ORGANISM: Homo sapiens

<400> SEQUENCE: 3

Gly Gly Gly Gly Ser Ala Pro Gly Gly Gly Ser
 1               5                  10

<210> SEQ ID NO 4
<211> LENGTH: 23
<212> TYPE: PRT
<213> ORGANISM: Homo sapiens

<400> SEQUENCE: 4

Val Asn Ala Lys Thr Thr Ala Pro Ser Val Tyr Pro Leu Glu Pro Val
 1               5                  10                 15

Ser Gly Ser Ser Gly Ser Gly
            20

<210> SEQ ID NO 5
<211> LENGTH: 13
<212> TYPE: PRT
<213> ORGANISM: Homo sapiens
<220> FEATURE:
<223> OTHER INFORMATION: Xaa = any amino acid

<400> SEQUENCE: 5

Leu Xaa Leu Ile Phe Glu Ala Gln Lys Ile Glu Trp Arg
 1               5                  10

<210> SEQ ID NO 6
<211> LENGTH: 19
<212> TYPE: PRT
<213> ORGANISM: Homo sapiens

<400> SEQUENCE: 6

Ala Arg Lys Cys Ser Leu Thr Gly Lys Trp Thr Asn Asp Leu Gly Ser
 1               5                  10                 15

Asn Met Thr

<210> SEQ ID NO 7
<211> LENGTH: 9
<212> TYPE: PRT
<213> ORGANISM: Homo sapiens

<400> SEQUENCE: 7

Glu Glu Glu Glu Tyr Met Pro Met Glu
 1               5

<210> SEQ ID NO 8
<211> LENGTH: 9
<212> TYPE: PRT
<213> ORGANISM: Homo sapiens

<400> SEQUENCE: 8

Gly Met Ala His His His His His His
 1               5

<210> SEQ ID NO 9
<211> LENGTH: 8
<212> TYPE: PRT
<213> ORGANISM: Homo sapiens

<400> SEQUENCE: 9

Thr Pro Pro Pro Glu Pro Glu Thr
 1               5

<210> SEQ ID NO 10
<211> LENGTH: 9
<212> TYPE: PRT
<213> ORGANISM: Homo sapiens

<400> SEQUENCE: 10

Ser Thr Pro Pro Pro Gly Thr Arg Val
 1               5

<210> SEQ ID NO 11
<211> LENGTH: 20
<212> TYPE: DNA
<213> ORGANISM: Homo sapiens

<400> SEQUENCE: 11
gaartavccc ttgaccaggc                                          20

<210> SEQ ID NO 12
<211> LENGTH: 23
<212> TYPE: DNA
<213> ORGANISM: Homo sapiens

<400> SEQUENCE: 12
gcacctccag atgttaactg ctc                                      23

<210> SEQ ID NO 13
<211> LENGTH: 35
<212> TYPE: DNA
<213> ORGANISM: Homo sapiens

<400> SEQUENCE: 13
cccgggccac catggratgs agctgkgtma tsctc                         35

<210> SEQ ID NO 14
<211> LENGTH: 29
<212> TYPE: DNA

```
<213> ORGANISM: Homo sapiens

<400> SEQUENCE: 14
ggtggcggcg cgccgggagg cggcggttc                                    29

<210> SEQ ID NO 15
<211> LENGTH: 39
<212> TYPE: DNA
<213> ORGANISM: Homo sapiens

<400> SEQUENCE: 15
gcctcccggc gcgccgccac caccgctgcc accgccacc                         39

<210> SEQ ID NO 16
<211> LENGTH: 32
<212> TYPE: DNA
<213> ORGANISM: Homo sapiens

<400> SEQUENCE: 16
gaggtgaccg gtgagcaggt ggagcagctt cc                                32

<210> SEQ ID NO 17
<211> LENGTH: 44
<212> TYPE: DNA
<213> ORGANISM: Homo sapiens

<400> SEQUENCE: 17
gaggtggagg cccagccggc catggcccag caggtgagac aaag                   44

<210> SEQ ID NO 18
<211> LENGTH: 36
<212> TYPE: DNA
<213> ORGANISM: Homo sapiens

<400> SEQUENCE: 18
gaggtggagc tcgagcaatg ctggtgtcat ccaaac                            36

<210> SEQ ID NO 19
<211> LENGTH: 30
<212> TYPE: DNA
<213> ORGANISM: Homo sapiens

<400> SEQUENCE: 19
gaggtggaga ctagtagctt ctgggttctg                                   30

<210> SEQ ID NO 20
<211> LENGTH: 33
<212> TYPE: DNA
<213> ORGANISM: Homo sapiens

<400> SEQUENCE: 20
gaggtggagc ccggggtctg ctcggcccca ggc                               33

<210> SEQ ID NO 21
<211> LENGTH: 32
<212> TYPE: DNA
<213> ORGANISM: Homo sapiens

<400> SEQUENCE: 21
gaggtgaccg gtcagcaggt gagacaaagt cc                                32

<210> SEQ ID NO 22
<211> LENGTH: 68
```

```
<212> TYPE: DNA
<213> ORGANISM: Homo sapiens

<400> SEQUENCE: 22
gtggagatcg ataagtgtac ttacgttttc attatcgcga tccggagtta acgtctgctc    60
ggccccag                                                             68

<210> SEQ ID NO 23
<211> LENGTH: 46
<212> TYPE: DNA
<213> ORGANISM: Homo sapiens

<400> SEQUENCE: 23
aacgcaaaga caaccgcccc ttcagtatat ccactagcgc ccgttt                   46

<210> SEQ ID NO 24
<211> LENGTH: 47
<212> TYPE: DNA
<213> ORGANISM: Homo sapiens

<400> SEQUENCE: 24
ccggaaacgg gcgctagtgg atatactgaa ggggcggttg tcgcgtt                  47

<210> SEQ ID NO 25
<211> LENGTH: 54
<212> TYPE: DNA
<213> ORGANISM: Homo sapiens

<400> SEQUENCE: 25
cgagaggaag aagagtacat gccgatggaa taatgaaaac gtaagtacac ttat          54

<210> SEQ ID NO 26
<211> LENGTH: 54
<212> TYPE: DNA
<213> ORGANISM: Homo sapiens

<400> SEQUENCE: 26
cgataagtgt acttacgtmc attattccat cggcatgtac tcttcttcct ctcg          54

<210> SEQ ID NO 27
<211> LENGTH: 21
<212> TYPE: DNA
<213> ORGANISM: Homo sapiens

<400> SEQUENCE: 27
cgaaaacgta agtacactta t                                              21

<210> SEQ ID NO 28
<211> LENGTH: 23
<212> TYPE: DNA
<213> ORGANISM: Homo sapiens

<400> SEQUENCE: 28
cgataagtgt acttacgttt tcg                                            23

<210> SEQ ID NO 29
<211> LENGTH: 39
<212> TYPE: DNA
<213> ORGANISM: Homo sapiens

<400> SEQUENCE: 29
gaggtggccc agccggccat ggccgacatc cagatgacc                           39
```

```
<210> SEQ ID NO 30
<211> LENGTH: 31
<212> TYPE: DNA
<213> ORGANISM: Homo sapiens

<400> SEQUENCE: 30
gaggtgacta gttttgattt ccagcttggt g                            31

<210> SEQ ID NO 31
<211> LENGTH: 51
<212> TYPE: DNA
<213> ORGANISM: Homo sapiens

<400> SEQUENCE: 31
ctagtggagg tggcggatca ggaggcggag gttctggcgg aggtgggagt c      51

<210> SEQ ID NO 32
<211> LENGTH: 51
<212> TYPE: DNA
<213> ORGANISM: Homo sapiens

<400> SEQUENCE: 32
tcgagactcc cacctccgcc agaacctccg cctcctgatc cgccacctcc a      51

<210> SEQ ID NO 33
<211> LENGTH: 28
<212> TYPE: DNA
<213> ORGANISM: Homo sapiens

<400> SEQUENCE: 33
gaggtgctcg aggaggtgca gctggtgg                               28

<210> SEQ ID NO 34
<211> LENGTH: 27
<212> TYPE: DNA
<213> ORGANISM: Homo sapiens

<400> SEQUENCE: 34
gaggtgtccg gagacatcca gatgacc                                27

<210> SEQ ID NO 35
<211> LENGTH: 28
<212> TYPE: DNA
<213> ORGANISM: Homo sapiens

<400> SEQUENCE: 35
gaggtgtcgc gatgaggaga cggtgacc                               28

<210> SEQ ID NO 36
<211> LENGTH: 43
<212> TYPE: DNA
<213> ORGANISM: Homo sapiens

<400> SEQUENCE: 36
gaggtggaat tctcattacc cgggtgagga cacggtgacc atg              43

<210> SEQ ID NO 37
<211> LENGTH: 28
<212> TYPE: DNA
<213> ORGANISM: Homo sapiens

<400> SEQUENCE: 37
gtggaggaat tcgtctgctc ggccccag                               28
```

```
<210> SEQ ID NO 38
<211> LENGTH: 52
<212> TYPE: DNA
<213> ORGANISM: Homo sapiens

<400> SEQUENCE: 38
gaggtgtcgc gacagctacc ggtgtccact ccgagcaggt ggagcagctt cc        52

<210> SEQ ID NO 39
<211> LENGTH: 52
<212> TYPE: DNA
<213> ORGANISM: Homo sapiens

<400> SEQUENCE: 39
gaggtgtcgc gacagctacc ggtgtccact cccagcaggt gagacaaagt cc        52

<210> SEQ ID NO 40
<211> LENGTH: 32
<212> TYPE: DNA
<213> ORGANISM: Homo sapiens

<400> SEQUENCE: 40
caagcagcct caggaactct ggaaatacgc tc                              32

<210> SEQ ID NO 41
<211> LENGTH: 32
<212> TYPE: DNA
<213> ORGANISM: Homo sapiens

<400> SEQUENCE: 41
gagcgtattt ccagagttcc tgaggctgct tg                              32

<210> SEQ ID NO 42
<211> LENGTH: 19
<212> TYPE: DNA
<213> ORGANISM: Homo sapiens

<400> SEQUENCE: 42
aacggtggag ggggctcat                                             19

<210> SEQ ID NO 43
<211> LENGTH: 23
<212> TYPE: DNA
<213> ORGANISM: Homo sapiens

<400> SEQUENCE: 43
ccggatgagc ccctccacc gtt                                         23

<210> SEQ ID NO 44
<211> LENGTH: 32
<212> TYPE: DNA
<213> ORGANISM: Homo sapiens
<220> FEATURE:
<223> OTHER INFORMATION: n = a, t, c, or g

<400> SEQUENCE: 44
cccgggccac catggagnca caknctcagg tc                              32
```